United States Patent
Furusako et al.

(10) Patent No.: US 7,264,967 B2
(45) Date of Patent: Sep. 4, 2007

(54) ANTI-CD14 MONOCLONAL ANTIBODY HAVING EFFECT OF INHIBITING CD14/TLR BINDING

(75) Inventors: Shoji Furusako, Tokyo (JP); Kamon Shirakawa, Tokyo (JP); Sadao Mori, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 273 days.

(21) Appl. No.: 10/432,236

(22) PCT Filed: Sep. 28, 2001

(86) PCT No.: PCT/JP01/08563

§ 371 (c)(1),
(2), (4) Date: May 22, 2003

(87) PCT Pub. No.: WO02/42333

PCT Pub. Date: May 30, 2002

(65) Prior Publication Data

US 2004/0091478 A1    May 13, 2004

(30) Foreign Application Priority Data

Nov. 22, 2000    (JP) .............................. 2000-356719

(51) Int. Cl.
*C12N 5/06* (2006.01)
(52) U.S. Cl. ................ 435/332; 530/387.1; 530/387.3; 530/388.1; 424/143.1
(58) Field of Classification Search ................ 435/332; 530/387.1, 387.3, 388.1; 424/143.1
See application file for complete search history.

(56) References Cited

U.S. PATENT DOCUMENTS

| | | |
|---|---|---|
| 5,730,980 A | 3/1998 | Ulevitch et al. |
| 2004/0092712 A1 * | 5/2004 | Furusako et al. ........... 530/350 |

FOREIGN PATENT DOCUMENTS

| | | | |
|---|---|---|---|
| EP | 0 911 400 A1 | | 4/1999 |
| JP | 8-510909 A | | 11/1996 |
| JP | 10-505839 A | | 6/1998 |
| WO | WO9101639 A1 | * | 2/1991 |
| WO | WO94/28025 | * | 12/1994 |
| WO | WO94/28025 A | | 12/1994 |
| WO | WO95/31562 | * | 11/1995 |
| WO | WO96/08272 A1 | | 3/1996 |
| WO | WO96/20957 | * | 7/1996 |
| WO | WO98/39438 A1 | | 9/1998 |

OTHER PUBLICATIONS

Paul W. ed. Fundamental Immunology, 3rd edition, 1993, p. 242.*
Rudikoff et al. Proc. Natl. Acad. Sci. USA 79:1979-1983 (1982).*
Skerra A. Journal of Molecular Recognition 13:167-187 (2000).*
Iwaki D. et al. Biochemical and Biophysical Research Communications 328: 173-176, 2005.*
Ulevitch R. Crit. Care Med. 29(7): S8-S12, 2001.*
Akashi, Sachiko, et al. Biochemical and Biophysical Research Communications. vol. 268, No. 1, pp. 172-177, Feb. 2000.
Hashimoto, Masahito, et al. Biochemical and Biophysical Research Communications. vol. 273, No. 1, pp. 164-169, Jun. 2000.
Tapping, Richard I. The Journal of Immunology. vol. 165, pp. 5780-5787, Nov. 15, 2000.
Schroder, Nicolas W. J. The Journal of Immunology, vol. 165, pp. 2683-2693, Sep. 2000.
M. O. Labeta et al., Eur. J. Immunol. 1993, 23:2144-2151.
S. D. Wright et al., Science, 1990, vol. 249, pp. 1431-1433.
T. S.-C. Juan et al., J. Biol. Chem., vol. 270, No. 3, pp. 1382-1387, Jan. 20, 1995.
T. S.-C. Juan et al., J. Biol. Chem., vol. 270, No. 29, pp. 17237-17242, Jul. 21, 1995.
T. S.-C. Juan et al., J. Biol. Chem., vol. 270, No. 10, pp. 5219-5224, Mar. 10, 1995.
F. L. Rock et al., Proc. Natl. Acad. Sci. USA, vol. 95, pp. 588-593, Jan. 1998.
O. Takeuchi et al., Immunity, vol. 11, pp. 443-451, Oct. 1999.
R.-B. Yang et al., Nature, vol. 395, pp. 284-288, Sep. 17, 1998.
W. C. Van Voorhis et al., J. Exp. Med., vol. 158, pp. 126-145, Jul 1983.
Bazil et al., Eur. J. Immunol., vol. 16, pp. 1583-1589, 1986.
Regine Landmann et al.; Microbes and Infection; vol. 2, No. 3; Mar. 2000; pp. 295-304; XP002277719.

* cited by examiner

*Primary Examiner*—Stephen L. Rawlings
*Assistant Examiner*—Brad Duffy
(74) *Attorney, Agent, or Firm*—Birch, Stewart, Kolasch & Birch, LLP

(57) ABSTRACT

The present invention provides an antibody which specifically recognizes an epitope containing a part of a domain based on a finding that the domain ranging from the 269- to 315-positions of human CD14 represented by SEQ ID NO:1 is a site capable of interacting with another protein, an antibodies provided. This antibody can inhibit the interaction between human CD14 and another protein and thus suppress cell activation. And also, the present invention provides hybridomas producing the above antibody or its fragment; a peptide containing the amino acids in the domain as specified above; a method of constructing an antibody with the use of this peptide as an immunogen; and a method of screening a medicament for sepsis involving the step of bringing a test substance into contact with CD14 and TLR.

15 Claims, 13 Drawing Sheets

FIG. 12

| PEPTIDE | INHIBITORY ACTIVITY |
|---------|---------------------|
| A | + |
| B | + |
| C | − |
| D | − |
| E (CONTROL) | |

```
283      301    307        315 318          329 331            343
LDLSCNRLNRAPQPDELPEVDNLTLDGNPFLVPGTALPHEGSMNSGVVPACARSTLSVGVSGTL
  ─────────────                ───────────
        A              B             C              D
```

FIG. 13

| sCD14 DELETION TAILORED MUTANT | | | BINDING ACTIVITY | | |
|---|---|---|---|---|---|
| TYPE | POSITION OF DELETION | FEATURE | F1024-1-3 | 3C10 | MEM-18 |
| 1-356 | — | — | + | + | + |
| 1-328 | C-TERMINUS | — | + | + | + |
| 1-315 | C-TERMINUS | — | + | + | + |
| 1-307 | C-TERMINUS | — | (+) | + | + |
| 1-285 | C-TERMINUS | — | — | + | + |
| 1-246 | C-TERMINUS | — | — | + | + |
| 1-183 | C-TERMINUS | — | — | + | + |
| 1-152 | C-TERMINUS | — | — | + | + |
| 1-307 | Δ7-11 | 3C10 BINDING REGION | + | — | + |
| 1-307 | Δ57-64 | MEM-18 BINDING REGION | + | + | — |
| 1-307 | Δ180-234 | — | + | + | + |
| 1-307 | Δ235-282 | — | + | + | + |
| 1-307 | Δ180-282 | — | + | + | + |

FIG. 14

| sCD14 AMINO ACID SUBSTITUTION TAILORED MUTANT | | BINDING ACTIVITY | | |
|---|---|---|---|---|
| TYPE | POSITION OF SUBSTITUTION | F1024-1-3 | 3C10 | MEM-18 |
| 1-307 | — | + | + | + |
| 1-307 | D284A | + | + | + |
| 1-307 | S286A | + | + | + |
| 1-307 | S286K | + | + | + |
| 1-307 | C287A | + | + | + |
| 1-307 | R289A | + | + | + |
| 1-307 | P294A | — | + | + |

FIG. 15

L CHAIN
1                LV-CDR1              LV-FR2         LV-CDR2    LV-FR3
LV-FR1
YIVMTQTPTSISISVGERVTMNCKASQNVGSNVDWYQQKTGQSPKLLIYKASNRYTGVPDRFTGSGSGTDFTFTISNMQA
81     LV-CDR3      LV-FR4
VDLAVYYCMQSNTNPPWTFGGGTKLELKRADAAPTVSIFPPSMEQLTSGGATVVCFVNNFYPRDISVKWKIDGSEQRDGV
161
LDSVTDQDSKDSTYSMSSTLSLTKVEYERHNLYTCEVVHKTSSSPSSRASTGIEC

H CHAIN
1                         HV-CDR1    HV-FR2              HV-CDR2              HV-FR3
HV-FR1
EVKLLESGGGLVQPSQTLSISCKASGYTFTDYAMNWVKQAPGDGLKWMGWINTGTGKPTYADDFKQRFVFSLETSASTAY
81         HV-CDR3           HV-FR4
LQINNLNIEDTATYFCTRSTFYYSSYIYGWYFDFWGPGTMVTVSSAETTAPSVYPLAPGTALKSNSMVTLGCLVKGYFPE
161
PVTVTWNSGALSSGVHTFPAVLQSGLYTLTSSVTVPSSTWPSQTVTCNVAHPASSTKVDKKIVPRNC (AMINO ACIDS SEQUENCES OF CDR ARE UNDERLINED)

FIG. 16

| SEQ ID NO: | REGION | AMINO ACIDS SEQUENCE |
|---|---|---|
| 3 | LV-CDR1 | QNVGSNVDWY |
| 4 | LV-CDR2 | KASNRY |
| 5 | LV-CDR3 | MQSNTNPPW |
| 6 | HV-CDR1 | DYAMN |
| 7 | HV-CDR2 | WINTQTGKPTYADDF |
| 8 | HV-CDR3 | TYFCTRSTFYYSSYIYGW |

FIG. 17

L CHAIN

LVCDR1
TACATTGTTATGACCCAGACCCCCACATCCATTTCCATATCAGTAGGAGAGAGGGTCACCATGAACTGCAAGGCCAGTCAGAATGTGGCT

LV-CDR2
TCTAATGTAGACTGGTACCAACAGAAAACAGGGCAGTCTCCTAAACTGCTTATCTACTCAAGGCCATCCAACCGTACACTGGCGTCCCTGAT

LV-CDR3
CGNTTCACAGGCAGTGGATCTGGAACAGATTTCACTTTCACCATCAGCAACATGCAGGCTGTGGACCTGGCTGTTTATTACTGTATGCAG
TCTAACACCAATCCTCCGTGGACGTTCGGTGGAGGCACCAAGCTGGAATTGAAACGGGCTGCTGACCAACTCTATCCATCTTCCA
CCATCCATGGAACAGTTAACATCTGGAGGTGCCACAGTGGTGTCCTGGACAGTGTTACTGGACAGGACAGCAAAGACAGCACGTACGCAGCACCCTC
ATTGATGGCAGTGAACAACGAGATGGTGTGTCATATGAAAGGCATAAGAAAGGCATACGGGCATCATCACGTCACGTCACGTCACGTGTTCAAGAGCTTCA
TCCTTGACCAAGGTTGAATATGAAAGGCATAACGCTCTATAACCTCTATACCTGTGAGGTTGTTCATAAGACATCATCCTCACGTCGTCAAGAGCTTCA
ACAGGAATTGAGTGT

H CHAIN

GAGGTGAAACTGTGGAGAATCTGGAGGAGGCTTGGTACAGCCGTCACAGACCCTGTCTCTATCTCCCTGCAAGGCTTCTGGGTATACCTTCACA

HVCDR1
GACTATGCAATGAACTGGGTGAAACAGGCTCCAGGAGAGGCTTGAAGTGGATTGGCTGGATTAATACCCACAGTGGAAGAACATGAAACTGGAAAGCCAAACATAT
GCGGGATGATTTCAAACAAGCGGTTGTCTTCTTCTTGGAAACTTCTGCCAGCACTGCAGATCAACTGCAGATCAACAACCTCAATATTGAGGAC

HVCDR3
ACAGCTACATATTTTCTGTACAGATCCACTTTTTACTATAGCAGCTATATCACGGGCGTAGTACTTTGACTTCTGGGCCCAGGAACCATG
GTCACCGTCTCCTCAGCTGAAACAACAACAGCCCCATCTGTCTATCCACTGGCTCCTCTGGAACTGCTCTCAAAAGTAACTCCATGGTGACCCTG
GGATGCCTGGTCAAGGGCTATTTCCCTGAGCCAGTGACCCTGACCTGGAACTCTGGACCCTGTGCAGCCCTGTGCACACCTTCCCAGCT
GTCCTGCAGTCTGGGCTCTACACTCCAGCTCAGTGACTGTACCCTCCAGCACCTGGCCCAGCCAGACCGTCACCTGCAACGTGTCCCACCCC
CACCCCGGCCAGCAGCACCAAGGTGGACAAGAAATTGTGCCCAGAAACTGT (NUCLEOTIDE SEQUENCES ENCODING FOR CDR ARE UNDERLINED)

FIG. 18

| REGION | AMINO ACIDS SEQUENCE |
|---|---|
| LV-CDR1 | CAGAATGTGGGTTCTAATGTAGACTGGTAC |
| LV-CDR2 | AAGGCATCCAACCGGTAC |
| LV-CDR3 | ATGCAGTCTAACACCAATCCTCCGTGG |
| HV-CDR1 | GACTATGCAATGAAC |
| HV-CDR2 | TGGATCAACACCCAAACTGGAAAGCCAACATATGCGGATGATTTC |
| HV-CDR3 | ACATATTTCTGTACAAGATCCACTTTTACTATAGCAGCTATATCTACGGGTGG |

US 7,264,967 B2

ANTI-CD14 MONOCLONAL ANTIBODY HAVING EFFECT OF INHIBITING CD14/TLR BINDING

This application is the national phase under 35 U.S.C. §371 of PCT International Application No. PCT/JP01/08563 which has an International filing date of Sep. 28, 2001, which designated the United States of America.

TECHNICAL FIELD

The present invention relates to an anti-CD14 antibody and fragment thereof, a hybridoma producing the antibody or fragments thereof, a peptides, a method of preparing the antibody and a pharmaceutical composition for treating sepsis.

More specifically the present invention relates to an anti-CD14 antibody specifically recognizing an epitope including 8 amino acids or more than 8 amino acids which present at least the region at positions 269 to 315 amino acids in the amino acids sequence of the human CD14 peptide, to the antibody which is an inhibitor for the binding between CD14 and Toll Like Receptor (hereinafter, referred to as "TLR"), to an anti-CD14 monoclonal antibody having an amino acid sequences of selected from SEQ: ID Nos: 3, 4, 5, 6 and 7 as their CDR, a humanized antibody or a chimeric antibody, to each peptide having the above described amino acid sequences, and to a pharmaceutical composition for sepsis.

BACKGROUND ART

CD14 is a glycoprotein composed of 356 amino acids and anchored thereto through glycosylphosphatidylinositol (GPI) on membranes of macrophages, monocytes, Kupffer cells, neutrophiles, and partly B cells.

Human CD14 includes besides membrane-bound type CD14 (hereinafter, also referred to as "mCD14"), soluble type CD14 (hereinafter, also referred to as "sCD14" or "soluble CD14"). Furthermore, it has been reported that in blood there are a plurality of sCD14s having different molecular weights (Labeta MO: Eur. J. Immunol., 23:2144, 1993).

Human CD14 is known as an LPS receptor for endotoxins of gram-negative bacilli (Wright et al.: Science, 249:1431, 1990), which receives LPS from LBP (LPS binding protein) in blood to form a complex.

Macrophage and the like that express mCD14 are activated by a complex of LPS and sCD14 to induce production of inflammatory cytokines (Hailmann E, et al.: J. Immunol., 156:4384, 1996).

In vascular endothelial cells and vascular smooth muscle cells that do not express mCD14, production of inflammatory cytokines is induced by a complex of sCD14 and LPS (hereinafter, also referred to as "sCD14/LPS") (Loppnow H, et al.: Infection & Immunity, 63:1020, 1995).

In addition, it reacts with bacterial cell components not only of gram-negative bacteria but also of gram-positive bacteria and with mycobacteria, and it has functions as a receptor for such as lipoteichoic acid (LTA) and peptide glycans (PepG), and reaction with above induces production of inflammatory cytokines of cells (Cleveland MG, et al.: Infect immunity, 64:1906, 1996).

Production of cytokines in cells through CD14 such as LPS or LTA exerts harmful effects on a living body and causes sepsis. Generally, in an early stage of sepsis, such symptoms as chill, hidrosis, fever, and hyposthenia are observed, and subsequently serious clinical symptoms that involve a shock are caused such as hypotension, neutropenia, disseminated intravascular coagulation syndrome, adult respiration distress syndrome, respiratory insufficiency, and multiple organ insufficiency.

As for the function of human CD14 to transduce the signal of LPS to cells, a part of the functioning region has been elucidated. The positions from 1 to 152 of the N-terminal are a region essential for expressing the function of CD14 (Juan TS, et al.: J. Biol. Chem., 270:1382, 1995) and the positions from 7 to 14 and the positions from 57 to 64 are portions essential for binding to LPS (Juan T S: J. Biol. Chem., 270, 29:17237 (1995) and Juan T S: J. Biol. Chem., 270, 10:5219 (1995)).

However, nothing has been elucidated on the function that regions from 153 to C-terminal of human CD14.

In addition, the participation of Toll like receptor (TLR) in the signal transduction of CD14/LPS to cells has been studied in recent years. To date TLR family genes composed of human TLR1, TLR2, TLR3, TLR4, TLR5 (Fernand R: Proc. Natl. Acad. Sci. USA, 95:588, 1998) and TLR6 (Takeuchi 0: Gene, 231:59, 1999) have been cloned.

Based on studies on TLR2- or TLR4-deficient mice, a possibility that TLR4 is required for signal transduction of cell components of gram-negative bacteria into cells and TLR2 is required for signal transduction of cell components of gram-positive bacteria into cells has been reported (Takeuchi O, et al.: Immunity, 11:443, 1999). Further, it has been reported that TLR2 participates in signal transduction of LPS into cells, TLR2 directly reacts with LPS on cell surfaces, and the reaction is enhanced in the presence of CD14 (Ruey-Bing Y: Nature, 395:284, 1998).

However, in the mutual action between CD14 and TLR, it has not been clarified if CD14 directly binds to TLR or a complex of TLR with accessory molecule, which is a low molecular substance whose function has not yet clarified. Further, the binding region of TLR and CD14 is quite unknown.

As the human anti-CD14 antibody that controls signal transduction of LPS through human CD14, there have been known 3C10 antibody that binds to 7th to 14th amino acids of human CD14 (Steinman: J. Exp. Med., 158: 126 (1983) and Juan T S: J. Biol. Chem., 270:29, 17237 (1995)), and MEM-18 antibody that binds to 57th to 64th amino acids of CD14 (Bazil: Eur. J. Immunol., 16:1583 (1986) and Juan T S: J. Biol. Chem., 270, 10, 5219 (1995)) are known and their application to medicaments for treating sepsis is disclosed.

Furthermore, 28C5 antibody and 23G4 antibody that inhibits binding of LPS and suppresses release of cytokines as well as 18E12 antibody that inhibits binding of LPS only partly and suppresses release cytokines have been disclosed (JP 8-510909 A).

Also, anti-CD14 antibody that is against the action of gram-positive bacteria and mycobacteria has been disclosed (JP 10-505839 A).

However, when used as a medicament for treating sepsis, an antibody that recognizes the binding region of LPS or an antibody that suppresses the binding of LPS is not expected to have an effect of suppressing signal transduction of already formed LPS/CD14. Further, it is not expected to have an effect of suppressing signal transduction by cell components of gram-positive bacteria, mycoplasma or the like, since the binding of LPS to CD14 is specifically inhibited. Further, the 18E12 antibody is not clarified with respect to the recognition site of CD14 and the mechanism of suppressing release of cytokines is also unclear.

As described above, participation of TLR in signal transduction of CD14/LPS into cells has been known. However, it is not certain as to whether or not the substance that inhibits this participation controls the signal transduction and no such inhibitory substance has been known.

DISCLOSURE OF THE INVENTION

An object of the present invention is to provide an anti-CD14 antibody which can control the signal transduction into cells even though CD14/LPC has already been formed, a biological active fragment thereof, an antibody having a specific amino acid sequence as its CDR, a hybridoma producing the antibody or fragments thereof, a peptides including amino acids presented in a specified region in human CD14 amino acid sequence, a method of preparing antibody using the peptides as an immunogen, and a pharmaceutical composition for sepsis.

The inventors of the present invention have made extensive studies in order to overcome the conventional problems as described above and provide an anti-CD14 antibody that inhibits the activation of cells and can control the signal transduction into cells, even though CD14/LPS has already been formed. Also, they provide an anti-CD14 monoclonal antibody having a specific amino acids sequence as its CDR region, a humanized antibody, a chimeric antibody. Further they provide an antibody that inhibits the binding between CD14 and TLR.

Also, by specifying in human CD14 a recognition region that is necessary for an anti-CD14 antibody to perform that action, they provide a method of preparing an antibody by using such a specified region.

Furthermore, they provide a pharmaceutical composition for sepsis containing as an active ingredient a substance that inhibits the binding between CD14 and TLR.

That is, the present invention provides anti-CD14 antibodies as described in (1) to (11), a method of preparing a humanized anti-CD14 antibody as described in (12) and a pharmaceutical composition as described in (13) below.
(1) An anti-CD14 antibody, which specifically recognizes an epitope comprising 8 or more amino acids out of the region at positions 269 to 315 amino acids of human CD14. An antibody according to (1), which is inhibitor for the binding between CD14 and Toll Like Receptor (TLR).
(3) An antibody according to (1) or (2), which is a monoclonal antibody.
(4) A fragment of an antibody according to (3) above, which is Fab, Fab' or (Fab')₂ having a biological activity.
(5) F1024-1-3 Monoclonal antibody produced by hybridoma F1024-1-3 (Accession No. FERM BP-7511).
(6) An anti-CD14 monoclonal antibody having at least one complementary determining region (CDR) having an amino acid sequence selected from among SEQ ID NO: 3, 4, 5, 6, 7, or 8 in the sequence listing.
(7) A humanized antibody or a chimeric antibody having at least one complementary determining region (CDR) having an amino acid sequence selected from among SEQ ID NO: 3, 4, 5, 6, 7, or 8 in the sequence listing.
(8) A peptide having at least one amino acid sequence selected from among SEQ ID NO: 3, 4, 5, 6, 7, or 8 in the sequence listing.
(9) A hybridoma producing an antibody or fragment of antibody according to any one of (3) to (5) above.
(10) A peptide comprising 8 or more amino acids out of the region at positions 269 to 315 amino acids of human CD14.
(11) A method of preparing an antibody which is an agent inhibiting the binding between CD14 and TLR, comprising using a peptide according to (10) above as an immunogen.
(12) A method of preparing a humanized anti-CD14 antibody comprising a steps of:
introducing a DNA encoding for a CDR having an amino acids sequence selected among SEQ ID NOs: 3, 4, 5, 6, 7 and 8 into a vector having a gene from human antibody and
producing a humanized anti-CD14 antibody using a host cell transformed by the vector.
(13) A pharmaceutical composition for sepsis comprising the antibody according to any one of (1) to (7), or the peptide according to (8) described above as an effective ingredient.

The present invention further provides monoclonal anti-CD14 antibodies as described in (14) to (17) below.
(14) A monoclonal antibody according to (3) described above as a rat monoclonal antibody.
(15) A monoclonal antibody according to (3) described above as a human monoclonal antibody.
(16) A monoclonal antibody being cross reactive with a rabbit, a dog or a monkey according to (3), (13) or (14) described above.
(17) A monoclonal antibody according to (3), (15) or (16) described above as a human monoclonal antibody.

Figure 1:
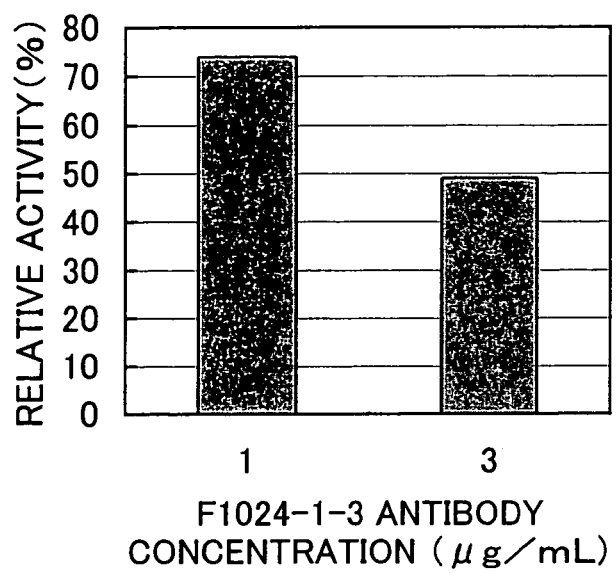
FIG. 1 is a graph illustrating measurement results obtained with respect to F1024-1-3 antibody which inhibited the activation of NF-κB by LPS/CD14 through Toll4 in the screening of a medicament for sepsis with a human anti-CD14 antibody.

Note that the inhibitory activity is calculated as described below.

(IL-8 Production amount when adding no antibody or recombinant−IL-8 Production amount when adding antibody or recombinant)/IL-8 Production amount when adding no antibody or recombinant×100

FIG. 12 is a graph illustrating the inhibitory activity of the binding F1024-1-3 antibody to CD14(1-356).

FIG. 13 is a graph illustrating binding activity of F1024-1-3 antibody to various kinds of CD14 deletion mutants.

FIG. 14 is a graph illustrating binding activity of F1024-1-3 antibody to various kinds of CD14 amino acid substitution mutants.

FIG. 15 is a diagram illustrating the determined amino acids sequence of heavy (SEQ ID NO: 94) and light (SEQ ID NO: 93) chain of variable region of F1024-1-3 antibody.

FIG. 16 is a diagram illustrating the CDR sequence of heavy and light chain of F1024-1-3 antibody.

FIG. 17 is a diagram illustrating one example of DNA encoding for the determined amino acid sequence of heavy (SEQ ID NO: 92) and light (SEQ ID NO: 91) chain of variable region of F1024-1-3 antibody.

FIG. 18 (SEQ ID NOS: 85-90) is a diagram illustrating one example of DNA encoding for the CDR sequence of heavy and light chain of F1024-1-3 antibody.

BEST MODE FOR CARRYING OUT THE INVENTION

Hereinafter, the present invention will be described in more detail.

A first embodiment of the present invention relates to an anti-CD14 antibody that specifically recognizes an epitope including 8 amino acids or more than 8 amino acids of the region from the positions 269 to 315 of human CD14.

The amino acid sequence described in SEQ ID NO:1 is an amino acid sequence of human CD14. The protein composed of 356 amino acids described in SEQ ID NO:1 equals to a full-length of human CD14.

The term "epitope" used herein means an antigenic determinant, which indicates a structure site that specifically binds to an antibody.

The region that an antibody recognizes is not limited to one that recognizes amino acid residues continuously arranged in a primary sequence and some antibodies have an epitope that recognizes the three-dimensional structure of a protein (Protein Engineering of Antibodies, pages 1 to 4, ed. by Keizaburo Miki et al.: "Kodansha Scientific" 1991).

For example, amino acid residues discontinuously arranged exist in a position sufficiently close to be recognized by an antibody in a manner of the three-dimensional structure, resulting in that there are some cases where an antibody that recognizes amino acid residues discontinuously arranged in a primary sequence employs the amino acid residues discontinuously arranged as an epitope.

For example, the epitope includes consecutive amino acids in a part of the region. However, it also includes amino acids that are discontinuously arranged in that region as described above. That is, the "part of the region that exists from the positions 269 to 315 of human CD14" includes a set of amino acids that are arranged continuously or discontinuously and also a set of amino acids which includes two or more interspersed of continuous or discontinuous amino acids as far as they exist in the region from the positions 269 to 315. An anti-CD14 antibody wherein specifically recognizes an epitope including 8 or more consecutive amino acids is preferred.

Also, the antibody of the present invention includes an antibody that recognizes an epitope including the region other than the positions 269 to 315. For example, it includes an antibody that specifically recognizes an epitope formed by 8 or more amino acid residues in the region from the positions 269 to 315 of human CD14 and several amino acid residues in a region other than that from the positions 269 to 315 of human CD14.

The antibody of the present invention specifically recognizes an epitope including 8 or more amino acids out of the region at positions 269 to 315 of human CD14 and binds to human CD14. Human CD14 may be either sCD14 or mCD14. Also, there is included an antibody that specifically recognizes an epitope including 8 or more amino acids out of the 269th to 315th of either one of the CD14s. For example, sCD14 exists in blood while mCD14 exists in macrophages.

The fact that an epitope including 8 or more amino acids out of the region at positions 269 to 315 of human CD14 is specifically recognized, can be judged by binding to a soluble polypeptide having amino acids at positions 1 to 315 from the N-terminal of human CD14 (sCD14(1-315)) but not binding to sCD14(1-268) in the same manner as, for example, Example 11 which will be described hereinbelow.

The antibody of the present invention has a function of inhibiting the binding of CD14 with TLR by specifically recognizing the epitope including 8 or more amino acids out of the region at positions 269 to 315 of human CD14.

CD14 binds to bacterial cell components and the CD14/bacterial cell components complex binds to TLR, thus signal transduction of cells to activate the cells. When cells are activated through the signal transduction mechanism, inflammatory cytokines are released from the cells to cause cytotoxicity, inflammation such as sepsis.

The antibody of the present invention suppresses activation of cells with the bacterial cell components by having the function of inhibiting the binding of CD14 with TLR, thus suppressing cytotoxicity and inflammation such as sepsis.

Explaining the "binding of CD14 with TLR" in detail, it means binding between a CD14/bacterial cell components complex, which is obtained by binding CD14 to bacterial cell components, and TLR. The bacterial cell components include LPS, LTA, peptide glycan (PGN), lipoarabinomannan or the like, mycoplasma, and the like. For example, LPS/CD14, which is a complex of LPS and CD14, transduces signal to cells by associating with TLR, in particular TLR2 or TLR4. When a signal is transduced into cells by TLR, activation of cells occurs through activation of NF-κB via MyD88, IRAK and NIK and the like. The antibody of the present invention inhibits binding of LPS/CD14 with TLR in this process.

"Having a function of inhibiting the binding of CD14 with TLR" is not particularly limited as far as the function of inhibiting the binding of CD14 with TLR is provided. This can be measured and judged by means of systems described in, for example, Examples 2 and 4, which will be described hereinbelow.

Also, as for the antibody of the present invention, it is preferred that an antibody suppresses activation of cells of TLR expressing cells by 30% or more is preferred.

In a more specific assay system, it is preferred that an antibody has a concentration of antibody of 10 µg/mL or less and suppresses the activation of NF-κB or IL-8 production of TLR expressing cells in the presence of 1 µg/mL of LPS and 0.5 µg/mL of exogenous CD14 by 30% or more. More preferably, the antibody is one that suppresses by 40% or more. Further preferably, the antibody is one that suppresses by 50% or more. Preferably in particular, the antibody is one that suppresses by 70% or more.

Further, as for the antibody of the present invention, it is preferred that an antibody suppresses production of cytokines in endothelial cells through exogenous LPS/CD14 to 60% or less. More specifically, it is preferred an antibody has an antibody concentration of 1 µg/mL or more and suppresses the IL-6 production of endothelial cells in the presence of 10 ng/mL of LPS and 300 ng/mL of exogenous CD14 to 60% or less. More preferably, the antibody is one that suppresses to 40% or less.

The binding of CD14 with TLR includes direct binding, binding through other factors, and binding activated by other factors. In blood or in vitro, there is included a case where the binding is performed in the presence of serum derived from an animal. For example, there is included a case where the binding is performed at the time when the structure of TLR4 or of a dimer of TLR4 is stabilized in the presence of MD2. The antibody of the present invention may have a function of inhibiting any one of such bindings. For example, there is included an anti-CD14 antibody that has a function of inhibiting the binding of CD14 with TLR in blood or in vitro in the presence of serum derived from an animal.

The reason that the antibody of the present invention has a function of inhibiting the binding of CD14 with TLR consists in that the region is a region that is associated with binding of CD14 with TLR. AS a result, an antibody that specifically recognizes an epitope including a part of the region at positions 269 to 315 of human CD14 has a function of inhibiting the binding of CD14 with TLR by changing the function of that region.

As for the region associated with the binding of CD14 with TLR, it is preferred that an antibody that recognizes an epitope region that functions as a region that is associated with binding of CD14 with TLR is completely included by the region from the positions 269 to 315 of human CD14. A more preferred epitope region is the region from the positions 285 to 315 of human CD14, and also, preferably it is the region from the positions 269 to 307 of human CD14 from the standpoint of having epitopes similar to that of F1024-1-3 antibody in the examples.

The antibody of the present invention is more preferably an antibody that specifically recognizes consecutive amino acids as an epitope.

The antibody of the present innovation is preferably an antibody that specifically recognizes an epitope including 8 or more amino acids out of the region from the positions 285 to 315 of human CD14 from the standpoint of having an epitope similar to the antibody of F1024-1-3 of Example. The antibody recognizes an epitope that resides from the positions 285 to 315 of a three-dimensional structure that can be generated by the fact that the amino acid at 294th position of CD14 is Pro.

Unlike other amino acids, Pro has an N atom bound to its α-carbon atom, which is incorporated into the cyclic structure to form an >NH group and therefore the polypeptide is restricted in its primary structure due to a Pro skeleton thereof, thus giving an influence on the three-dimensional structure of the protein. That is, Pro has no NH group and therefore it cannot form hydrogen bonds, thus failing to form an α-helix ("Protein Biotechnology," ed. by F. Frank, Baifukan). Although the antibody does not bind to CD14 which was carried out point mutation of Pro at position 294 of CD14, this is because three-dimensional structure of CD14 changed. That is, the antibody recognizes an epitope that resides from the positions 285 to 315 of the three-dimensional structure that can be generated by the fact that the amino acid at position 294 is Pro.

Further, the antibody of the present invention is an anti-human CD14 antibody. However, the present invention also includes antibodies against regions of CD14 of mammalians other than humans that are identical with the region concerned as far as it is an antibody that exhibits effects identical with those of the anti-human CD14 antibody described hereinbelow.

The amino acid sequence described in SEQ ID NO:2 is an amino acid sequence from the positions 269 to 315 of human CD14.

An antibody prepared by using a peptide that includes a part or whole region of the amino acid sequence described in SEQ ID NO:2 and has consecutive 8 or more amino acids as an immunogen is included in the antibody of the present invention. Preferably, it is an antibody prepared by using a peptide that includes a part or whole amino acid sequence of the region from the positions 285 to 307 of human CD14 and has consecutive 8 or more amino acids as an immunogen. Further, in consideration of the fact that a peptide assumes a three-dimensional structure, an antigen prepared by using a peptide having consecutive 10 or more amino acids, more preferably consecutive 15 or more amino acids as an immunogen is preferred.

The antibody of the present invention has a function of inhibiting the binding of CD14 with TLR by specifically binding to CD14. CD14 may be either sCD14 or mCD14. Also, the antibody of the present invention includes antibodies having a function of inhibiting the binding between either one of CD14s and TLR. As the examples, there can be referred to antibodies having a function of inhibiting the binding between sCD14 and TLR that exists in blood or antibodies having a function of inhibiting the binding between mCD14 and TLR that exists on macrophage and the like.

The antibody of the present invention may be either a polyclonal antibody or monoclonal antibody. To clarify the function of the antibody or exhibit it clearly, a monoclonal antibody is preferred.

The species of animal from which the antibody of the present invention is derived is not particularly limited. In consideration of ease of preparing antibodies, rat is preferred. In a case where it is used as a constituent of a pharmaceutical composition, the antibody of the present invention is preferably a human antibody. The human antibody also includes human antibodies prepared by immunizing human antibody producing mice. Additionally, the antibody of the present invention includes humanized antibodies, phage antibodies, chimeric antibodies or the like. The humanized antibody is an antibody that includes a constant region and a framework region derived from a human, and a complementarity determining region derived from a nonhuman. The phage antibody is an antibody prepared by fusing an antibody to the coat protein of filamentous phage to present the antibody on the surface of the phage particle, in which single chain Fv (scfv) form or Fab form is mainly used. The chimera antibody is an antibody that includes a variable region of monoclonal antibody from a nonhuman mammal, for example, mouse and a constant region from a human antibody.

The antibody of the present invention is not particularly limited to the molecular species thereof. Even when antibodies are classified into any class, subclass or isotype, they may be applied. Further, the present invention also includes biologically active antibody fragments, such as Fab, Fab', and (Fab')$_2$.

The antibody of the present invention can be prepared by using known technologies. For example, the monoclonal antibodies can be prepared by the following method.

The antibody of this invention can be prepared from the clones selected by using screening method of the fifth embodiment of this invention described below from the hybridomas produced by fusing the myeloma cells and the immunized cells of the mammal which is immunized with a protein having the whole amino acid sequence shown in SEQ No:1 or a peptide including consecutive 8 or more amino acids of the region from positions 269 to 315 as an immunogen. Also, the antibody of the present invention may be prepared by selecting a clone that binds to sCD14(1-315) whereas not binds to sCD14(1-268). Preferably a peptide composed of consecutive 8 or more amino acids in the region from the positions 285 to 307 is used as an immunogen. A peptide composed of preferably consecutive 10 or more amino acids, more preferably consecutive 15 or more amino acids is used as an immunogen.

The mammal to be immunized is not particularly limited. However, it is preferred that it is selected in consideration of compatibility with myeloma cells used in cell fusion and mice, rats, hamsters or the like preferred. As the myeloma cell, various known cells can be used. They include myeloma cells such as P3, P3U1, SP2/O, NS-1, YB2/0 and Y3-Ag1, 2, 3 and so on.

The immunization may be performed by a known method. For example, it is performed by administering an antigen intraperitoneally, subcutaneously, intravenously or into a footpad. In a case of administering the antigen, an adjuvant may be used and it is preferred that the antigen is administered in plural times. In a case of administering the antigen, an adjuvant may be used in combination and it is preferred that the antigen is administered in plural times. The immunized cells are preferably spleen cells or cells originated from Lymph nodes, in which they are extracted at the time when several days passed after the final administration of antigen for example, 3 days.

The fusion between the immunized cells and myeloma cells can be performed by a known method such as the method of Milstein (Methods in Enzymol., Vol. 73, page 3). Examples of the known method includes a method of using polyethylene glycol (PEG) as a fusing agent, or an electrofusion method.

The mixing ratio between immunized cells and myeloma cells is not particularly limited as far as they can be fused each other. It is preferred to use myeloma cells in from an amount 1/10 time that of the immunized cell to in an equivalent amount that of.

In a method in which cell fusion is performed by using PEG (average molecular weight 1,000 to 4,000), the concentration of PEG is not particularly limited, however it is preferred to perform the cell fusion at a concentration of 50%. Further, an auxiliary such as dimethyl sulfoxide (DMSO) may be added as a fusion accelerator.

The fusion is started by adding a PEG solution warmed to 37° C. to mixed cells and terminated by addition of the medium after reaction for 1 to 5 minutes.

The hybridomas formed by this fusion are cultured in a selection medium containing hypoxanthine, thymidine, and aminopterine (HAT medium) for 1 to 7 days, to thereby separate from non-fused cells. The obtained hybridomas are further selected by the antibodies they produce. The selected hybridoma is monoclonized by a known limiting dilution method to establish it as a monoclonal antibody producing hybridoma.

As for the method of detecting the activity of antibody that is produced by the hybridoma, a known method may be used. Examples thereof include an ELISA method, a coagulation reaction method, and a radioimmunoassay method.

The established hybridoma is cultured by a known method and from its supernatant monoclonal antibody can be obtained. Also, the hybridoma may be administered to a mammal having compatibility therewith to proliferate it and a monoclonal antibody may be obtained from the ascites of the mammal.

The purification of antibody can be performed by using known purification means such as a salting out method, a gel permeation method, ion exchange chromatography, or affinity chromatography.

Furthermore, the human antibody may be prepared by using the method developed by Ishida et al. (PNAS, 97:722, 2000). That is, first a trans-chromosome (Tc) mouse is prepared as follows. According to the method of Ishida et al., human No. 2 chromosome fragment (Ig light chain κ) and No. 14 chromosome fragment (Ig heavy chain) are introduced into murine ES cells with a microcell fusion method, and chimera mice having respective chromosome fragments are prepared by the method of Joyner et al. ("Gene Targeting," Experimental Methods Series, Medical Science International). Then, the prepared two kinds of chimera mice are mated, to thereby prepare a chimera mouse having both human No. 2 chromosome fragment (Ig light chain κ) and No. 14 chromosome fragment (Ig heavy chain). In order to have the productivity of endogenous murine antibody originated from a mouse lost, a double KO mouse with endogenous Ig heavy chain and κ chain being knocked out is prepared by the method of Capecchi et al. (Mol. Cell. Biol. 12:2919-2923, 1992), and mated with a chimera mouse having introduced therein a human chromosome fragment, to thereby prepare a transchromosome mouse including human No. 2 chromosome fragment (Ig light chain κ) and No. 14 chromosome fragment (Ig heavy chain) with endogenous Ig heavy chain and κ chain being knocked out. The prepared Tc mouse produces human originated antibodies in blood, which include an antibody having murine γ chain as a part thereof. However no murine Ig(κ) is detected therein. Even after several generations, the obtained Tc mouse retains the chromosome and its off springs can be used for preparing an anti-CD14 human monoclonal antibody as described hereinbelow.

50 μg of purified CD14 antigen after being mixed with Titer Max Gold (Cytrex Co.) is subcutaneously administered to a Tc mouse and an additional administration is performed after 3 weeks in the same manner. An increase in antibody titer is determined by reacting diluted antiserum with a plate having immobilized an antigen thereto, then detecting bound human antibody in the serum with anti-human IgG antibody. Cell fusion is performed 3 days after administering 50 μg of an antigen to the abdominal cavity of the mouse whose antibody titer has increased. Specifically, harvested spleen cells are mixed with murine myeloma cells (SP2/O-Ag14) and then fused with PEG4000 (Merck), followed by selecting hybridomas in HAT medium containing G418 (1 mg/mL). The appeared hybridomas are screened by using anti-human IgG K antibody, anti-IgG antibody, anti-IgG2 antibody, anti-IgG3 antibody or anti-IgG4 antibody as a secondary antibody, to thereby select a hybridoma that produces human antibodies binding to CD14. Furthermore, by the screening method according to the Example 2 which will be described later, the human CD14 antibody of the present invention can be obtained.

Further, the humanized antibody obtained by a CDR graft method can be prepared by using the known method described in Nature, 321:522, 1986. The antibody obtained by a phage presenting method can be prepared by using the known method described in Annu Rev. Immunol, 12:433, 1994. The chimera antibody ca be prepared by using the known method described in Nature, 312:643, 1984.

And more, the methods for preparing the humanized antibody and the chimeric antibody will be described herein below in detail.

Fab, Fab', (Fab')$_2$ and the like, which are fragments of the antibody of the present invention, can be prepared by a known method (Eiji Ishikawa, Ultra-High Sensitive Enzyme Immunoassay, Japan Scientific Societies Press (JSSP)).

Polypeptides can be prepared by purifying soluble type CD14 in human serum with a known method. Also, a method of using a generally used peptide synthesizer (Peptide Synthesizer 432A Type, Perkin-Elmer Japan Co., Ltd.), or the like, a genetic engineering technique ("New Cell Engineering Experiments Protocols," Ed. Department of Carcinostatic Research, The Institute of Medical Science, The University of Tokyo, Shujunsha) and the like may be used.

For example, a peptide having consecutive 8 or more amino acids that reside in the region from the positions 269 to 315 can be synthesized by an Fmoc method with using 432A Type peptide synthesizer. After deprotection with TFA and cleavage from the resin, it is purified by using C18 HPLC column (Capcell-pak, Shiseido Co., Ltd.), to thereby prepare the target peptide.

One preferred example of the antibody of the present invention is F1024-1-3 antibody produced by hybridoma F1024-1-3 obtained by cell fusion between immunized cells, which is prepared by immunizing a rat with CD14 protein purified from human serum as an antigen, and myeloma cells. The hybridoma F1024-1-3 has been deposited at International Patent Organism Depository (IPOD), National Institute of Advanced Industrial Science and Technology, Japan at Central 6, 1-1, Higashi 1-chome, Tsukuba-shi, Ibaraki-ken, Japan (Hereinafter, referred to as "National Institute of Bioscience and Human-Technology") on Sep. 29, 2000) (Accession No. P-18061) and transferred from the original deposit to an international deposit (Accession No. FERM BP-7511) on Mar. 16, 2001).

Furthermore, CDRs of F1024-1-3 antibody, VL-CDR1, VL-CDR2, VL-CDR3, HL-CDR1, HL-CDR2 and HL-CDR3, are represented as SEQ ID NO: 3, 4, 5, 6, 7, and 8 in FIG. 16, respectively. The monoclonal antibodies of the present invention include an anti-CD14 monoclonal antibody having at least one of the CDRs that have an amino acid sequence described in SEQ ID NO: 3, 4, 5, 6, 7, or 8. Preferably, it is an anti-CD14 monoclonal antibody having one of the amino acid sequences described in SEQ ID NO: 3 to 5 to which one or more of VL-CDR1 to CDR3 correspond, and having one of the amino acid sequences described in SEQ ID NO: 6 to 8 to which one or more of HL-CDR1 to CDR3 correspond. More preferably, it is an anti-CD14 monoclonal antibody having an amino acid sequence in which VL-CDR1 to HL-CDR3 respectively have the respective amino acid sequences described in SEQ ID NO: 3 to 8.

The subtypes of the anti-CD14 monoclonal antibody are not limited. They include not only IgG of the subtype of F1024-1-3 antibody but also IgA, IgD, IgE, and IgM thereof. They retain the sequences of hyper variable regions (CDR) of the F1024-1-3 antibody, and they can be prepared by a genetic engineering technique by which a heavy chain of the antibody is substituted from κ chain to λ chain or by which a light chain is substituted from γ chain to a chain, δ chain, ε chain, or μ chain.

In the present invention, an anti-CD14 chimeric antibody or an anti-CD14 humanized antibody having at least one of the CDRs that have an amino acid sequence described in SEQ ID NO: 3, 4, 5, 6, 7, or 8. Preferably, it is an anti-CD14 chimeric antibody or an anti-CD14 humanized antibody having one of an amino acid sequence described in SEQ ID NO: 3 to 5 to which one or more of VL-CDR1 to CDR3 correspond, and also having one of amino acid sequence described in SEQ ID NO: 6 to 8 to which one or more of HL-CDR1 to CDR3 correspond. More preferably, it is an anti-CD14 chimeric antibody or an anti-CD14 humanized antibody in which VL-CDR1 to HL-CDR3 respectively have the amino acid sequences described in SEQ ID NO: 3 to 8.

Furthermore, a peptide having at least one of the amino acid described in SEQ ID NO: 3 to 8 is also included in the present invention. Preferably, it is a peptide composed of an amino acid sequence described in one of SEQ ID NO: 3 to 8. In addition, preferably, it is also a peptide containing amino acid sequences of SEQ ID NO: 3 to SEQ ID NO: 8 in this order from the N terminal to the C terminal. In addition, an appropriate linker may be placed among six amino acid sequences thereof.

The above-mentioned monoclonal antibody, humanized antibody, and chimeric antibody, the CD14/TLR-binding inhibiting function of the peptide can be determined by a screening of Example 2 described later.

A specific method for preparing a chimeric antibody or a humanized antibody will be described. Human constant region and reorganized variable region DNAs can be isolated from various human cells, preferably immortalized B cells in accordance with known manipulating techniques. By similar techniques, nonhuman antibody sequences can be isolated from nonhuman materials. For the DNA sequences, cells for the materials and host cells for expression and secretion can be obtained from various materials, such as American Type Culture Collection (Catalog of Cell Lines and Hybridoma, 5th Ed., (1985), Rockville, Md., the content of which is incorporated hereinto by reference).

In addition to these antibody chain in "naturally occurring form", other "substantially identical" modified antibody heavy chains and light chains may be easily designed and manufactured using various kinds of recombinant DNA technologies well-known by persons skilled in the art. For instance, the chain can be varied from a natural sequence at its primary structure level by substitution, addition, deletion, or the like of several amino acids at the terminal or midpoint of the chain. Alternatively, a polypeptide fragment only having a primary antibody structure portion such as one having one or more antibody activities (e.g., binding activity) may be manufactured. In particular, as with many genes, attention has been given to the fact that an antibody gene also contains separated functional regions and each region has a different biological activity. In general, a modification to a gene that encodes a desired epitope binding component can be easily attained by various kinds of well-known technologies such as site-directed mutagenesis (see Gillam and Smith, Gene 8:81-97 (1979) and Roberts et al., Nature 328: 731-734 (1987), the contents of which are incorporated hereinto by reference).

In a more preferable embodiment of the present invention, an epitope binding component is encoded by a "chimera" or a "humanized" antibody gene (Co and Queen, Nature, vol. 351, page 501, 1991).

The chimeric antibody is an antibody in which a light chain gene and a heavy chain gene are composed of antibody gene segments belonging to different species, typically obtained by genetic engineering. For instance, a variable (V) segment of a gene from a mouse monoclonal antibody may be coupled to a human constant (C) segment such as $\gamma_1$ and $\gamma_4$. Therefore, even though other mammal species may be used, a typical therapeutic chimeric antibody is a hybrid protein composed of V or an antigen-binding domain from a mouse antibody and C or an effecter domain from a human antibody.

As defined by Kabat et al., (Sequences of proteins of immunological interest, 5th ed., U.S. Department of Health and Human Services, 1991), the term "a framework region" refers to portions of antibody's light chain and heavy chain variable region comparatively being preserved (i.e., except of CDR) in various antibodies in a single species. In the present specification, the term "a human framework region" refers to a framework region substantially identical (about 85% or more) to a framework region of a naturally-occurring human antibody or a common sequence of such several kinds of antibodies.

The term "a humanized antibody" refers to an antibody containing at least one CDR from a human framework or a nonhuman antibody, where any constant region existed therein is substantially identical to the constant region of the human antibody. That is, at least about 85 to 90%, preferably at least 95% are identical. Therefore, it is likely that all portions of the humanized antibody except of CDR, are substantially identical to the corresponding portions of one or more sequences of a natural human antibody. For instance, the humanized antibody does not contain a chimeric mouse variable region/a human constant region antibody.

More specifically, in the present invention, these antibodies are humanized antibodies that contain at least one, preferably all (four) of one chain, more preferably all (four for each chain) of framework regions (FRs) from a plurality of, preferably from one human recipient (acceptor) antibody, and also contain one or more, or preferably all (three for each chain) of complementarity determining regions (CDRS) from an F1024-1-3 antibody. The antibody may have two pairs of light chain/heavy chain complexes. At least one chain, especially a heavy chain contains one or more, preferably all (three) of a complementarity-determining region of a donor (rat) antibody functionally coupled to a human framework region segment. For instance, the complementarity-determining region of the donor (rat) is implanted into the human framework region in the absence or presence of a naturally-associated additional donor (rat) amino acid residue. As a more clear example, each of the humanized antibodies of the present invention contains one of the amino acid sequences of SEQ ID NO: 3, 4, 5, 6, 7, or 8 in the sequence table, or at least one, preferably all (three for each chain) of CDRs composed of these amino acid sequences. Desirably, the positions of each CDR and framework in the humanized antibody may correspond to their positions in the original donor antibody.

In general, it is preffered that the humanized antibody of the present invention has a homology between the framework of a heavy chain variable region of the humanized antibody and the framework of a heavy chain variable region of the donor antibody in the range of from 65% or more to 95% or less, preferably from 70% or more to 90% or less (i.e., the percentage of sequence identity). On the standard scale, a heavy chain and a light chain from the same human antibody may be selected to provide a framework sequence, so that the possibility of incompatibility in the assembly of the two chains can be decreased. Alternatively, they may be derived from two or more different human antibodies.

Regarding the human framework region, a sequence having a high homology is selected by making a comparison between an amino acid sequence of a framework or of a variable region of a nonhuman antibody from which CDR is obtained and a corresponding sequence in the human antibody sequence collection and is used. The homology to the framework amino acid sequence is preferably 60% or more, more preferably 65% or more. In addition, the amino acid sequence of the heavy chain variable region of the recipient antibody is included in five, more preferably three sequences in the typical collection of the human antibody heavy chain variable region sequence that is most homologous to the amino acid sequence of the heavy chain variable region of the donor antibody. The humanized antibody can be designed as follows.

(1) When an amino acid falls into the following categories (a) to (c), a framework amino acid of a human antibody (recipient antibody) to be used is substituted with an amino acid derived from a nonhuman antibody (donor antibody) which supplies CDR.

(a) the amino acid in the human framework region of the recipient antibody is very rare in its position in a human antibody and the corresponding amino acid in the donor antibody is typical in its position in the human antibody;

(b) the amino acid is close to or adjacent to one of CDRs on the primary sequence; or (C) the amino acid has an atom within about 5, preferably 4, more preferably 3 Angstroms from CDR in a three-dimensional model of the donor or humanized antibody (Co et al., Proc, Natl. Acad. Sci. USA 88, 2869, 1991).

(2) When the amino acid in the human framework region of the recipient antibody and the corresponding amino acid in the donor antibody are very rare in their positions in a human antibody, the position in the human framework is substituted with a typical amino acid.

Regarding the detailed description of the manufacture of humanized antibody, Queen et al., Proc, Natl. Acad. Sci. USA 86: 10029 (1989), WO90/07861 and WO92/11018, Co et al., Proc, Natl. Acad. Sci. USA, 88, 2869 (1991), Co and Queen Nature, vol. 351, page 501, 1991, and Co et al., J. Immunol. 148: 1149 (1992) (the contents of which are incorporated hereinto by reference) may be referred to.

Generally, it is desirable that all or most of the substitutions of amino acids meet the criteria described above. However, it is ambiguous whether the individual amino acids meet the above-mentioned criteria, and also various kinds of antibodies may be produced instead in which one of them may or may not have its specific substitution. Therefore, CDR and FR may be optimized by computer modeling.

After a human antibody V region having a high homology has been found, the CDR sequence of the F1024-1-3 antibody is inserted into the framework portion thereof, followed by simulating its three-dimensional structure by computer molecular modeling. As a program to be used at this time, ABMOD or ENCAD (Biochemistry, 29: 10032, 1990)

may be used. The simulation of such a three-dimensional structure allows optimization in which an amino acid of FR in the proximity of CDR is substituted with another amino acid such that the arrangement of amino acids in the CDR region is allowed to optimally have its binding activity to CD14.

Furthermore, for the optimization of CDR and FR, it is possible to apply a method in which a part of the amino acid sequence of FR of the F1024-1-3 antibody is directly used and implanted into a human antibody V region. The FR region of the F1024-1-3 antibody is shown in FIG. 15. Parts of the sequences of CDR and FR of the F1024-1-3 antibody are implanted into the human antibody V region, and a three-dimensional structure thereof is simulated by computer modeling. As a program to be used at this time, Modeler and QUANTA/CHARMm (Molecular Simulations, Inc.) are used. 3 to 4 positions in the light chain and 7 to 8 positions in the heavy chain are replaced with amino acids derived from rats to allow the FR to be closely analogous to the structure of a rat antibody. In some cases, the arrangement of amino acids in the CDR region may easily optimize the binding activity to CD14.

Furthermore, as far as the binding activity of the anti-CD14 antibody is retained, 1 or not less than 2 amino acids among those in the CDR region may be subjected to deletion, substitution, insertion, or addition. In this case, for example, it is understood that the substitution between amino acids classified as homologous, such as Gly and Ala, Val, Leu and Ile, Asn and Gln, Cys and Met, or Lys and Arg, etc. allows the binding activity of the anti-CD14 antibody to be retained easily. In addition, amino acids located on some positions in the framework region directly interact to antigens. For example, they can be brought into a non-covalent contact with each other. These positions also become objects of the substitution described above. In particular, however, amino acids at the positions 26 to 30 in the heavy chain may be included in a hyper variable loop depending on a three-dimensional structure (Chothia and Lesk, J. Mol. Biol., 196: 901-917 (1987)). In such a sense, it can be implanted similarly to CDR.

Based on the obtained amino acid sequences, humanized antibodies are prepared. For instance, the gene sequence of a humanized antibody is determined using the determined amino acid sequences described above, and a gene that encodes a humanized monoclonal antibody is prepared. Specifically, DNA that encodes CDR is removed from the gene of the human V region, while DNA that encodes CDR derived from rat is inserted therein. Furthermore, depending on an amino acid to be replaced based on molecular modeling, the corresponding DNA sequence is modified by site-directed mutagenesis using PCR, or the like to prepare a recombinant human V region gene. This is cloned into a vector containing a C region of a light chain and a heavy chain of a human antibody to obtain an expression vector. By changing the sequence derived from human used at this time, sub classes of antibodies of human IgG1, IgG3, or the like can be obtained. The expression vector allows gene transfer and expression in mouse myeloma cell Sp2-O-ag14 (ATCC CRL1581) and hamster ovary cell CHO.

Compared with rat antibodies and in some cases compared with chimeric antibodies, the humanized antibody has at least three potential advantages in use for the medical treatment of human.

(1) An effecter portion is human, so that it may be provided with a more satisfactory interaction with other portions in a human immune system (e.g., more effective destruction of the target cells by complement-dependent cytotoxicity (CDC) or antibody-dependent cellular cytotoxicity (ADCC)).

(2) The human immune system does not recognize the framework or C region of the humanized antibody as a foreign substance. Therefore, the immune response to such antibodies being implanted is lower than that of the mouse antibodies, all of which are foreign substances or the chimeric antibodies, part of which are foreign substances.

(3) It is reported that the half-life of the inserted mouse antibody for the circulation in the human body is much shorter than the half-life of a normal antibody (Show, D. et al., J. Immunol. 138: 4534-4538 (1987)). Presumably, the implanted humanized antibody will have a half life more close to the half life of a naturally-occurring human antibody., so that it can be given at a smaller dosage or more little frequency of dosage.

The antibody of the present invention has a function of inhibiting the binding between CD14 and TLR by specifically binding with human CD14. That is, it is a binding inhibitor for CD14 and TLR. This indicates that it has a function of suppressing human CD14-mediated cell activation, so that it can be used in the therapy or prevention of diseases associated with bacterial infection. For example, it is useful in the therapy or prevention of symptoms accompanying an increase in concentration of inflammatory cytokines, in particular blood TNF, associated with diseases such as sepsis. More specifically, it is useful in the therapy or prevention of fever, hypotension, leukocytopenia, thrombocytepenia, a shock, and multiple organ insufficiency. Further, the causative agent of cell activities that the antibody of the present invention suppresses is not limited to LPS alone. The antibody of the present invention also suppresses the cell activation mediated by CD14 that has formed a complex with, for example, LTA, PGN, mycoplasma or the like. That is, in diseases caused by these substances, the antibody of the present invention is useful in the therapy or prevention thereof as described above.

Since the antibody of the present invention has a function of specifically recognizing an epitope comprising a part of the region from the positions 269 to 315 of human CD14, it is useful as a tool for qualitative or quantitative determination of human CD14. For example, there is a measurement method in which an analyte and the antibody of the present invention are contacted to form an antigen-antibody complex, and then the complex is detected or quantitated. Examples of analyte include serum, urine, body fluid, supernatant of culture and the like. As for the detection or quantitation method of the antigen-antibody complex, an ELISA method, a RIA method or the like may be exemplified.

A second embodiment of the present invention relates to a hybridoma that produces the monoclonal antibody of the present invention. The hybridoma of the present invention can be prepared by the method described in the first embodiment of the present invention.

One preferred example of the hybridoma of the present invention is Hybridoma F1024-1-3 (Accession No. FERM BP-7511) that produces F1024-1-3 antibody, which is a preferred example of the antibody of the present invention.

A third embodiment of the present invention relates to a peptide comprising consecutive 8 or more amino acids out of the region from the positions 269 to 315 of human CD14 described in SEQ ID NO:1. Preferably, it is a peptide comprising consecutive 8 or more amino acids out of the region from the positions 285 to 307 of human CD14. Also, preferably, it is a peptide comprising consecutive 10 or more, particularly preferably consecutive 15 or more amino acids.

The peptide of the present invention can be prepared by the method described in the first embodiment of the present invention.

A fourth embodiment of the present invention relates to a method of preparing an antibody characterized by using the peptide according to the third embodiment of the present invention as an-immunogen. Preferred examples of the peptide used as an immunogen include the preferred examples of the peptide according to the third embodiment of the present invention.

The particulars of the method of the present invention are the same as those described in the first embodiment of the present invention.

It can be confirmed by using, for example, the method described in Example 2 that the antibody prepared is a binding inhibitor for inhibiting the binding between CD14 and TLR. a method of preparing a humanized anti-CD14 antibody.

A fifth embodiment of the present invention relates to a method of preparing a humanized anti-CD14 antibody comprising a steps of; introducing a DNA encoding for a CDR having an amino acids sequence selected among SEQ ID NOs: 3, 4, 5, 6, 7 and 8 into a vector having a gene from human antibody and producing a humanized anti-CD14 antibody using a host cell transformed by the vector.

A method of preparing a humanized anti-CD14 antibody of the present invention characterized in that introducing a DNA having a nucleotides sequence encoding for a CDR having an amino acids sequence selected among SEQ ID NOs: 3, 4, 5, 6, 7 and 8 into a vector having a gene from human antibody and producing a humanized anti-CD14 antibody using a host cell transformed by the vector.

Preferably the present method comprises introducing a DNA having a nucleotides sequence encoding for a CDR having an amino acids sequence selected among SEQ ID NOs: 3, 4, 5, 6, 7 and 8 into a vector having a gene from human antibody and producing a humanized anti-CD14 antibody using a host cell transformed by the vector.

The particulars of the method of the present invention are the same as those described in the first embodiment of the present invention.

Furthermore, it is preferable, in order to put present invention into practice, to design a model of a molecule in which a CDR having an amino acids sequence selected among SEQ ID NOs: 3, 4, 5, 6, 7 and 8 is inserted into the variable region of the human antibody, and simulate on computer the three-dimensional structure of CDR and framework region (FR) and optimize the amino acids sequence of CDR and FR, then to determine the amino acids sequence of the humanized anti-CD14 antibody.

It is recommended to introduce DNA that encodes a CDR having an amino acids sequence selected among SEQ ID NOs: 3, 4, 5, 6, 7 and 8, and all or part of FR that is modified through optimization, into thus determined vector having a gene from human antibody that encodes stationary region of at least heavy chain or light chain of amino acid sequence of humanized anti-CD14 antibody.

The term "a part of FR" includes not only a part of FR of continuous amino acids sequence but also of non-continuous amino acids sequence substituted for optimization. Thus, the method of producing humanized anti-CD14 antibody by designing and optimizing amino acids sequence will be included in present invention so long as optimization is made by a model of a molecule transplanted with CDR having an amino acids sequence selected among SEQ ID NOs: 3, 4, 5, 6, 7 and 8 into the variable region of humanized anti-CD14 antibody.

Preferably, a model of a molecule transplanted with CDR having an amino acids sequence selected among SEQ ID NOs: 3, 4, 5, 6, 7 and 8 into the variable region of humanized anti-CD14 antibody should be adopted.

Further, the present invention is also characterized in that a host cell is producing humanized anti-CD14 antibody. Preferable example of a base sequence that encodes a CDR having an amino acids sequence selected among SEQ ID NOs: 3, 4, 5, 6, 7 and 8 is shown on FIG. 18. An example of a nucleotides sequence that encodes heavy chain and light chain including FR is shown on FIG. 17.

The produced humanized antibody can be confirmed as an inhibitor between CD14 and TLR by using the method described in Example 2.

A sixth embodiment of the present invention relates to a method of screening a medicament for treating sepsis comprising the step of contacting CD14, TLR and a test substance.

The "method of screening a medicament for treating sepsis" is a method for studying to see whether or not a test substance is a medicament for treating sepsis or a candidate substance of a medicament for treating sepsis. Also, it is a method of selecting a medicament for treating sepsis or a candidate substance of a medicament for treating sepsis from a plurality of test substances.

The screening method of the present invention comprises the step of contacting CD14, TLR and a test substance.

The CD14 source used in the screening method of the present invention includes CD14 expressed in cells, sCD14 existing in blood or sCD14 prepared by a genetic engineering technique. The CD14 expressed in cells may be expressed in cells by a genetic engineering technique. Further, sCD14 may be a modified one as far as it contains at least the region from the positions 269 to 315 of human CD14. It is preferably full length CD14 in consideration of maintenance of three-dimensional structure of CD14.

The TLR source used in the screening method of the present invention includes cells that express TLR, TLR or the like prepared by a genetic engineering technique. TLR expressed in cells may be expressed in cells by a genetic engineering technique. Alternatively, the CD14 source and TLR source may exist in the same cell.

In addition, it is preferred that in the step of contacting the cells expressing TLR prepared by a genetic engineering technique with CD14 and a test substance, a CD14 activating substance is added simultaneously. This is because the CD14 activated by the CD14 activating substance readily binds to TLR.

The CD14 activating substance is not particularly limited as far as it binds to CD14 to form a complex and has a function of activating CD14. For example, it includes bacterial cell components such as LPS or LTA, mycoplasma, and the like.

The step of contacting CD14, TLR and a test substance is not particularly limited as far as the step allows them to be contacted. It includes, for example, directly contacting in a solution, fixing CD14 or TLR to a plate or the like and mixing the others in a solution, followed by adding the solution to the plate, or adding in a culture medium of CD14 or the cells expressing TLR the others and so forth.

The order of contacting CD14, TLR, a test substance is and CD14 activating substance is not particularly limited.

For example, it includes an order in which these may be contacted simultaneously, an order in which the CD14 activating substance and CD14 are contacted in advance, an order in which the CD14 activating substance and CD14 are contacted with the test substance before the CD14 activating substance and CD14 are contacted with TLR.

The judgment as to whether the test substance is a medicament for treating sepsis is not particularly limited. It includes, for example, directly observing the binding between CD14 and TLR, and judging the test substance is a medicament for treating sepsis or selecting it as a medicament for treating sepsis, if the test substance inhibits the binding, or depending on the degree of inhibition of the binding. Alternatively, it includes measuring activation of CD14 or of TLR expressing cells and making such a judgment or selection.

The test substance of the screening method is not particularly limited. For example, an antibody such as anti-CD14 antibody and the like, a polypeptide such as CD14 mutant polypeptide and the like, low molecular compounds are listed in the examples of the test substance.

By the screening method of the present invention, medicaments for treating sepsis can be selected conveniently. That is, the screening method of the present invention is useful as a method of conveniently screening active ingredients for pharmaceutical compositions for sepsis.

A seventh embodiment of the present invention relates to a pharmaceutical composition for sepsis containing a binding inhibitor for CD14 and TLR as an active ingredient.

The binding inhibitor for CD14 and TLR contained in the pharmaceutical composition of the present invention is not particularly limited as far as it is an agent that inhibits directly binding of CD14 to TLR or an agent that inhibits CD14 from forming a complex or the like by binding to TLR through a third substance. The mechanism of inhibition is not limited either.

It is preferred that the binding inhibitor for CD14 and TLR contained in the pharmaceutical composition of the present invention is the inhibitor having the ability of inhibition at which activation of TLR expressing cells is suppressed by 30% or more. More specifically, in an assay system, when a concentration of 3 µg/mL or more of the antibody in the presence of 1 µg/mL of LPS and 0.5 µg/mL of exogenous CD14, the inhibitor having the ability of inhibition at which activation of TLR expressing cells is suppressed the activation of NF-κB of TLR expressing cells by 30% or more is preferable. More preferably, the inhibitor having the ability of inhibition at which the activation is suppressed by 40% or more. Preferably, the seventh embodiment is a pharmaceutical composition for sepsis comprising an antibody of the present invention or fragment thereof as the binding inhibitor for CD14 and TLR as an effective component.

It is preferred that the binding inhibitor for CD14 and TLR contained in the pharmaceutical composition of the present invention or the product obtained from the screening method of the present invention has a titer at which activation of TLR expressing cells is suppressed by 30% or more. More specifically, in an assay system, the inhibitor has a titer at which activation of NF-κB production of TLR expressing cells in the presence of 1 µg/mL of LPS and 0.5 µg/mL of exogenous CD14 is suppressed by preferably 30% or more. More preferably, it has a titer at which the activation is suppressed by 40% or more.

In the route of sepsis that is caused by cell activation through human CD14, the binding inhibitor for CD14 and TLR inhibits the binding of CD14 with TLR, thereby inhibiting signal transduction that is performed from CD14 to TLR. As a result, it blocks the signal transduction subsequent to TLR, to thereby suppress cell activation, thus exhibiting therapeutic effect for sepsis.

That is, the pharmaceutical composition of the present invention is useful for the therapy and the prevention of diseases associated with bacterial infection. For example, it is useful for sepsis, articular rheumatism, AIDS, autoimmune diseases, hemolytic anemia, tumors, atopic diseases, allergic diseases, sarcoidosis, malaria, psoriasis, fever, hypotension, leukocyto failure, thrombocytopenia, a shock, and multiple organ insufficiency. In particular, it is useful in the therapy and the prevention of symptoms that are caused due to an increase in inflammatory cytokines accompanying these diseases, in particular in blood TNF level. Among these diseases, it is useful in the therapy and the prevention for sepsis of gram-negative bacteria infection with participation of LPS, gram-positive bacteria infection with participation of LTA, peptide glycan or mycoplasma infection. That is, it is useful not only for exhibiting therapeutic effects at the time when symptoms of these diseases have appeared or are in progress but also for exhibiting preventive effects for those patients who contain LPS, LTA, mycoplasma or the like at high levels in blood or those persons infected with bacteria who are suspected to bring into such a circumstance.

Further, as far as it contains the binding inhibitor for CD14 and TLR as an active ingredient, various additives that are pharmaceutically acceptable may be included. For example, carriers, excipients, stabilizers, lubricants, colorants, disintegrants, antiseptics, isotonic agents, agents which have a stabilizing effect, dispersants, antioxidants, buffers, preservatives, suspending agents, emulsifiers, commonly used suitable solvents (sterilized water, plant oil, etc.), and further dissolution aids that are physiologically acceptable and the like may be selected appropriately.

The pharmaceutical composition of the present invention may contain antibiotics, steroids, various cytokine antibodies, anticoagulation factors or the like. These substances may exhibit additive or synergistic effects together with the antibody of the present invention as the ingredient, thereby to give a more effective pharmaceutical composition.

The dosage in the case of administering the pharmaceutical composition of the present invention is not particularly limited. For example, when the antibody of the present invention is used as the active ingredient, it is preferred that the dosage is 0.1 mg/kg or more. More preferably, the dosage is 1 to 10 mg/kg. In the case where the pharmaceutical composition of the present invention is used as a drug, it is preferred that the preparation form includes suppositories, inhalants, and in particular injections. Also, there are various administration routes applicable. However, parenteral administration is preferred. AS for parenteral administration, injections such as intravenous administration, intraarterial administration, subcutaneous administration, and intramuscular administration are generally used. Other examples include intrarectal administration, percutaneous absorption, permucous absorption and the like. The time or number of administration includes preventive administration single administration, and continuous administration or the like depending on the condition of patient.

The present invention discloses a CD14 mutant polypeptide having a function of inhibiting the binding between CD14 and TLR and being either one of [1] and [2] below:

[1] having an amino acid sequence corresponding to the amino acid sequence described in SEQ ID NO:1 with the N-terminal being any one of amino acids at positions 1 to 6 thereof and the C-terminal being any one of amino acids at positions 246 to 306 thereof;

[2] having an amino acid sequence corresponding to the amino acid sequence described in SEQ ID NO:1 with the N-terminal being any one of amino acids at positions 1 to 6 thereof and the C-terminal being any one of amino acids at positions 269 to 356 thereof, and at least any one of amino acids at positions 269 to 307 thereof being substituted by other amino acid or acids.

Hereinafter, explanation will be made mainly on the amino acid sequence of human CD14 polypeptide and the amino acid sequence of human CD14 will be sometimes termed simply as amino acid sequence of CD14. However, CD14 may be CD14 polypeptides from species other than human as far as it is CD14 of a mammalian other than human and has a portion comprising a function corresponding to the amino acids at positions 269 to 307 of human CD14 being modified similarly to exhibit equivalent effect to that of the modified product of the present invention.

"Modified CD14 polypeptide" includes a polypeptide comprising CD14 polypeptide having deleted a part thereof, a polypeptide comprising CD14 polypeptide having a part of the amino acids thereof substituted, and a polypeptide comprising CD14 polypeptide having added thereto amino acid or acids. It also includes modified polypeptides having some of these modifications in combination.

The polypeptide of the present invention has a function of inhibiting the binding between CD14 and TLR. The particulars of the function of inhibiting the binding between CD14 and TLR are as described in the first embodiment of the present invention.

Further, the polypeptide of the present invention is preferably a polypeptide that suppresses cell activation of TLR expressing cells by 30% or more.

In a more specific assay system, a polypeptide is preferred that suppresses the activation of NF-KB or production of IL-8 in TLR expressing cells in a polypeptide concentration of 10 μg/mL or lower and in the presence of 1 μg/mL of LPS and 0.5 μg/mL of exogenous CD14 by 30% or more. More preferably, it is a polypeptide that suppresses by 40% or more. Further more preferably, it is a polypeptide that suppresses by 50% or more. Particularly preferably, it is a polypeptide that suppresses by 70% or more.

Further, the CD14 mutant polypeptide of the present invention is preferably a polypeptide that by itself does not induce cytokines in endothelial cells in the presence of LPS. In a more specific assay system, it is preferred that this polypeptide does not induce IL-6 production in endothelial cells in the presence of 10 ng/mL LPS at a polypeptide concentration of 300 ng/mL or less.

The term "does not induce" means that IL-6 to be measured in the assay system concerned is below the detection limit. For example, in using a human IL-6 EIA kit (PE Biosystems Corp.) in the measurement of IL-6 production, "below the detection limit" means 50 μg/mL or less.

The CD14 mutant polypeptide of the present invention is preferably a polypeptide that suppresses production of cytokines through exogenous LPS/CD14 in endothelial cells to 60% or less.

In a more specific assay system, a polypeptide is preferred that suppresses production of IL-6 in endothelial cells in a polypeptide concentration of 300 ng/mL or more in the presence of 10 ng/mL of LPS and 300 ng/mL of exogenous CD14 to 60% or less. More preferably, it is a polypeptide that suppresses to 40% pr less.

The "LPS/CD14" means a complex of LPS and CD14 bound to each other. In consideration of the activity, among the polypeptides in [1] above, CD14 mutant polypeptides having a C-terminal that corresponds to any one of the amino acids at positions 246 to 285 of CD14 is preferred. More preferred are polypeptides that have a C-terminal corresponding to the amino acid 246 or 285 of CD14.

Also, in respect of the activity, among the polypeptides in [2] above, those polypeptides are preferred that have C-termini corresponding to any one of amino acids at positions 269 to 356 thereof and have any at least one of amino acids at positions 269 to 286 thereof substituted by other amino acid or acids, i.e., Leu, Ala, Cys or Gly. More preferred are those CD14 mutant polypeptides that have C-termini corresponding to amino acids at positions 284 to 356 thereof and have at least any one of amino acids at positions 284 to 286 thereof substituted by other amino acid or acids, i.e., Leu, Ala, Cys or Gly. Furthermore, those CD14 mutant polypeptides are preferred that have C-termini corresponding to the amino acid at position 307 thereof and at least any one of amino acids at positions 284 to 286 thereof substituted by other amino acid or acid, i.e., Leu, Ala, Cys or Gly.

From the point of view of removing bacterial cell components by the polypeptide itself, it is preferred that the polypeptide of the present invention binds to bacterial cell components. For example, binding site of CD14 of LPS is at positions 7 to 14 and 57 to 64 thereof and the sequences of the sites are maintained in the polypeptide of the present invention.

In the polypeptide of the present invention, 1 to 6 amino acids at the N-terminal may be deleted, substituted, inserted or added as far as its function is maintained. For example, a polypeptide in which Met is further added to the N-terminal thereof is also included in the polypeptide of the present invention. In addition, in the amino acid sequence in the midway, one or several amino acids may be deleted, substituted, inserted or added.

The polypeptide of the present invention may be subjected to any modification as far as it does not lose its characteristics. The modification includes modification during or after translation of polypeptide, chemical modification and the like which the protein will be possibly subjected to during its production by culturing eucaryotic cells such as animal cells or yeast cells.

A method of producing the polypeptide of the present invention is disclosed hereinafter.

In the production method of the present invention, the transformant of the present invention is cultured and amplification or induction of expression of gene is performed as necessary. Then, culture mixture is recovered and the polypeptide of the present invention is purified by a suitable combination of operations such as concentration, solubilization, dialysis, and various kinds of chromatographies.

The "culture mixture" means a transformant, a medium containing a transformant, culture supernatant, or a lysate of cells. In the production method of the present invention, when the produced polypeptide of the present invention is secreted in the supernatant of cell culture, the polypeptide can be purified from the culture supernatant. On the other hand, when the polypeptide is accumulated in the transformant, the cells are dissolved or disrupted by appropriately selecting a method suited for the host cell from a lysozyme treatment, surfactant treatment, freeze thawing, compression, ultrasonication and other methods and then the polypeptide is recovered and purified as a soluble fraction or insoluble fraction by centrifugation, filtration or the like method.

The nucleotide sequences of the DNA encoding for the polypeptides of the present invention are shown as SEQ ID: NOs 9 to 11.

The recombinant vector of the present invention can be obtained by a method in which DNA of the gene of the present invention is ligated to other DNA fragment having any optional base sequence, a method in which DNA of the gene of the present invention is introduced in any optional vector (cf., Sambrook J. et al., Molecular Cloning, a Laboratory Manual 2nd ed., Cold Spring Harbor Laboratory, New York, 1989) or the like.

Specifically, it is recommended that DNA and a vector are digested with appropriate restriction enzymes, respectively, and the obtained respective fragments are ligated with a DNA ligase. The vector may be any vector such as a plasmid vector, a phage vector, or a virus vector. A commercially available vector may also be used. Typical examples of the vector include pUC118, pBR322, pSV2-dhfr, pBluescriptII, PHIL-S1, lZapII, lgt10, pAc700, YRP17, PEF-BOS, PEFN-II and the like.

The transformant can be obtained by introducing the recombinant vector described above in a cell or microbe that serves as a host.

The transformant of the present invention may be obtained by transforming either one of procaryotic cell and eucaryotic cell. The procaryotic cell includes *Escherichia coli, Bacillus subtilis*, etc. The eucaryotic cell includes mammalian cells such as COS cell, CHO cell, Hela cell, and Namalwa Cell and in addition thereto insect cells such as Sf cell, and yeast. Among these, transformants obtained by transforming *Escherichia coli*, mammalian cells and yeast are preferred since they are easy to handle and high expression amounts can be expected.

Among the mammalian cells, it is preferred to use dhfr deficient cell line of CHO cell as a host since the copy number of the gene can be increased. On the other hand, among yeasts, it is preferred to use yeasts belonging to the genus Pichia as a host since it produces a large amount of exogenous protein by secretion or it is preferred to use *Schizosaccharomyces pombe* as a host since it has an adduct sugar chain similar to that of mammalian species.

Culture of the transformant can be performed by a generally accepted technique by referring to various books (cf., for example, "Microbe Experimentation," ed. Incorporated Association the Japanese Biochemical Society, Tokyo Kagaku Dojin Co., Ltd., 1992).

When induction of expression of a gene is performed, a suitable drug selected depending on the promoter incorporated is used. For example, in the case where a trp promoter is incorporated, 3β-indolacrylic acid may be used, while dexamethazone may be used in the case of MMTV promoter or methanol may be used in the case of AOX1 promoter.

Typical examples of amplifying a gene include a method of using methotrexate when a dhfr deficient CHO cell as a host and a vector having dhfr are used and other methods.

The transformant used in the production method is not limited as far as it is the transformant of the present invention. However, preferably it is a transformant that uses any cell selected from mammalian cells such as COS cell and CHO cell, yeast, and *E. coli* as a host.

The transformant obtained by transforming a mammalian cell such as CHO cell with a recombinant vector having a promoter of EF1a is cultured in DMEM medium containing 10% fetal calf serum. The cells are inoculated in a density of about 1 to $10 \times 10^4$ cells/mL, and cultured under the conditions of 37° C., and 5% carbon dioxide gas/95% air. Usually, after 2 to 3 days, the cells reach a confluent state and at this point in time the medium is exchanged with D-MEM not containing serum. Subsequently, by performing the culture for 2 to 3 days, a culture mixture containing the target protein can be obtained. It is preferred to amplify the gene with methotrexate as described above to increase the production amount.

It is preferred that a dhfr deficient CHO cell as a host and a vector having dhfr are used.

As for the method of purifying the peptide of the present invention from the culture mixture described above, a suitable method selected as appropriate from among methods that are usually used for purifying polypeptides is used.

EXAMPLES

Hereinafter, the present invention will be explained in more detail by examples. However, they are indicated as only examples and the present invention should not be limited thereto. In the following description, abbreviations used are based on those abbreviations commonly used in the art.

Example 1

Preparation of Anti-Human CD14 Antibody

[Preparation of Antigen to be Administered]

5 mg of purified anti-human CD14 monoclonal antibody 3C10 (purchased from ATCC and prepared and purified by ordinary methods) was bound to Hitrap NHS-Activated resin (Amersham Pharmacia) according to the manual to prepare a 3C10-bound affinity column.

As for soluble type CD14, 100 mL of human serum (purchased from Japan Biotest) was added to the prepared column and continuously washed with phosphate buffer (pH 7.4) (hereinafter, referred to as PBS).

After confirming the lowering of the absorbance at a wavelength of 280 nm, the column was eluted with 0.1 M glycine hydrochloride buffer (pH 3.0) and the eluate was concentrated by ultrafiltration using Diaflow (Grace Japan).

After dialysis with PBS, the concentration of protein was calculated with the absorbance at a wavelength of 280 nm (coefficient: 1 O.D.=1 mg/mL). As a result, about 200 μg of purified soluble type CD14 was obtained and a band of about 55 kD was confirmed by SDS-PAGE analysis.

[Preparation of Anti-CD14 Monoclonal Antibody]

To the footpad of a female Wistar rat (purchased form SLC) aged 8 weeks was administered a 1:1 mixture consisting of 100 μg of the purified soluble type CD14 and Freund's complete adjuvant (Difco). After 3 weeks, ilium lymph node was harvested and lymphocytes were aseptically collected.

The obtained lymphocytes were mixed with murine myeloma cell SP2/O-Ag14 (ATCC CRL1581) in a ratio of 5:1 and cells fusion was performed with polyethylene glycol 1500 (Sigma). After the cell fusion, the cells were suspended in 10% fetal bovine serum/RPMI1640 containing hypoxanthine, aminopterin and thymidine and spreaded in wells of a 96-well plate (Nunc).

The cells were cultured under the conditions of 5% $CO_2$ at 37° C. until a stage where growth of hybridomas was confirmed when the medium was exchanged to the same medium as above but contained no aminopterin.

After 1 week from the cell fusion, the culture supernatant was sampled and hybridomas producing antibody binding to CD14 were screened by using a plate having immobilized thereto purified soluble type CD14. That is, 1 μg/mL of purified soluble type CD14 was immobilized to a plate (Maxisorp, Nunc) and blocked with 0.1% bovine serum albumin-containing PBS. Then, the culture supernatant was added thereto and reacted at 37° C. for 1 hour and thereafter washed with 0.9% physiological saline containing 0.05% Tween-20.

To each well, a peroxidase-labeled anti-rat immunoglobulin antibody (DAKO) was added and reacted at 37° C. for 1 hour. After the washing, tetramethylbenzidine color developer solution containing 0.02% hydrogen peroxide was added. After 10 minutes' reaction, the reaction was terminated with 0.5 M sulfuric acid.

The absorbance of the plate was measured at a wavelength of 450 nm and wells having an absorbance of 0.2 or higher were selected as anti-CD14 antibody-producing hybridomas.

The selected hybridomas were cloned by a limiting dilution method (Ando, Tamie and Chiba, Takeshi: "Introduction to Monoclonal Antibody Experimental Manipulation", Kodansha). After 10 days, screening was performed in the same manner as above to obtain 17 clones of anti-CD14 antibody-producing hybridomas.

Then, after the hybridomas were cultured in RPMI1640 containing 10% fetal bovine serum, cells were collected and production of antibody was performed by culturing the collected cells in Hybridoma-SFM (Gibco) to obtain supernatant containing monoclonal antibody. After removing cells from the culture supernatant through filter paper, the culture supernatant was purified through Protein G column (Prosep-G, Millipore) to obtain 17 kinds of purified anti-human CD14 antibodies.

Example 2

Screening of Anti-Human CD14 Antibody for a Medicament for Treating Sepsis.

(1) [Preparation of a Screening System]

[1] Construction of Human TLR4 Expression Plasmid

Since human TLR4 cDNA has a coding region of about 2.5 kb (Genbank Accession No. AF17765), cloning of TLR4 cDNA was performed separately for 1.1 kb on the 5'-flanking region and for 2.3 kb on the 3'-flanking region.

As for the cloning of the 5'-terminal side, sense primer 1 (tcgaggaagagaagacacca) (SEQ ID NO: 95) and antisense primer 1 (ccatccgaaattataagaaaagtc) (SEQ ID NO: 96) were designed, then human lung cDNA (CLONTECH Co.) was used as a template to perform PCR reaction with Pyrobest DNA Polymerase (TaKaRa Co., Ltd.) by repeating the cycle of 98° C. for 10 seconds, 55° C. for 30 seconds and 72° C. for 1 minute 30 times. As for the cloning of the 3'-terminal side, similar PCR was performed by designing sense primer 2 (cccatccagagtttagccct) (SEQ ID NO: 97) and antisense primer 2 (cccaagctttggaattactcacccttagc) (SEQ ID NO: 98) and using human spleen cDNA (CLONTECH Co.) as a template. The DNA fragments thus amplified were inserted into the EcoRV site of pBluescript II SK (+) (STRATAGENE Co.) and the nucleotide sequence of the resultant TLR4 cDNA was determined.

Subsequently, using the plasmids obtained, the 5'- and 3'-terminal side fragments of TLR4 cDNA were bound together at the EcoRI site, which is located 856 bp downstream from the translation initiator codon, and incorporated into a mammal cell expression vector pcDNA 3.1 (−) (Invitrogen Co.) to prepare a human TLR4 expression plasmid pcDNAT4.

[2] Establishment of Human TLR4 Expression Transformant Cell Line

The plasmid pcDNAT4 prepared in [1] above was introduced into HEK293 cells (ATCC) as human fetal kidney derived cell line by the following method. That is, 25 μL of FuGENE6 (Roche Diagnostics Co.) was mixed with 6.3 μg of PcDNAT4 according to the attached protocol and the mixture was added to HEK293 cells grown in a 75 cm² flask in a semiconfluent manner. After being cultured for 24 hours under the conditions of 5% $CO_2$ at 37° C., the cells were peeled off and resuspended in a DMEM medium containing 1.2 mg of G418 (GIBCO-BRL Co.) and 10% inactivated FBS. Subsequently, the medium was exchanged twice a week and culture was continued for 20 days to obtain G418 resistant cell line T4-14.

(2) [Screening of Human CD14 Antibody for a Medicament for Sepsis]

T4-14 cells were suspended in a DMEM medium containing 10% inactivated FBS, inoculated in wells of a 24-well plate in a density of $1\times10^5$ cells/well and cultured for 24 hours under the conditions of 5% $CO_2$ and 37° C. Thereafter, using FuGENE6, 100 ng/well of a reporter gene pNFκB-Luc (CLONTECH Co.) was introduced, followed by further cultivation for 24 hours. LPS (*E. coli* 055:B5, Difco Co.) in a final concentration of 1 μg/mL, sCD14(1-356) in a final concentration of 0.5 μg/mL, and anti-CD14 antibody 3C10 or the anti-CD14 antibody obtained in Example 1 in a final concentration of 1 to 10 μg/mL were added and culture was continued for 6 hours. Thereafter, the cells were lysed with Passive Lysis Buffer (Promega Co.) and the luciferase activity of the lysate was measured using Luciferase Assay System (Promega) according to the attached protocol. As a result, as the antibody having activity, F1024-1-3 antibody was obtained that inhibited activation of NF-κB by about 50% in a system in which 10 μg/mL of antibody was added, as shown in FIG. 1.

Typing of isotypes of F1024-1-3 antibody by using Rat MonoAB ID/SP kit (ZYMED) revealed IgG1/κ.

Example 3

Confirmation of Cross Reactivity of F1024-1-3 Antibody.

For the purpose of usefulness of F1024-1-3 antibody in a sepsis animal model, cross reactivity of F1024-1-3 antibody with various animal-derived CD14s was studied. First, human CD14(1-356) was immobilized to wells of a plate (Maxisorp, Nunc) in an amount of 50 ng/well and blocked with 0.5% BSA/PBS.

Figure 2:
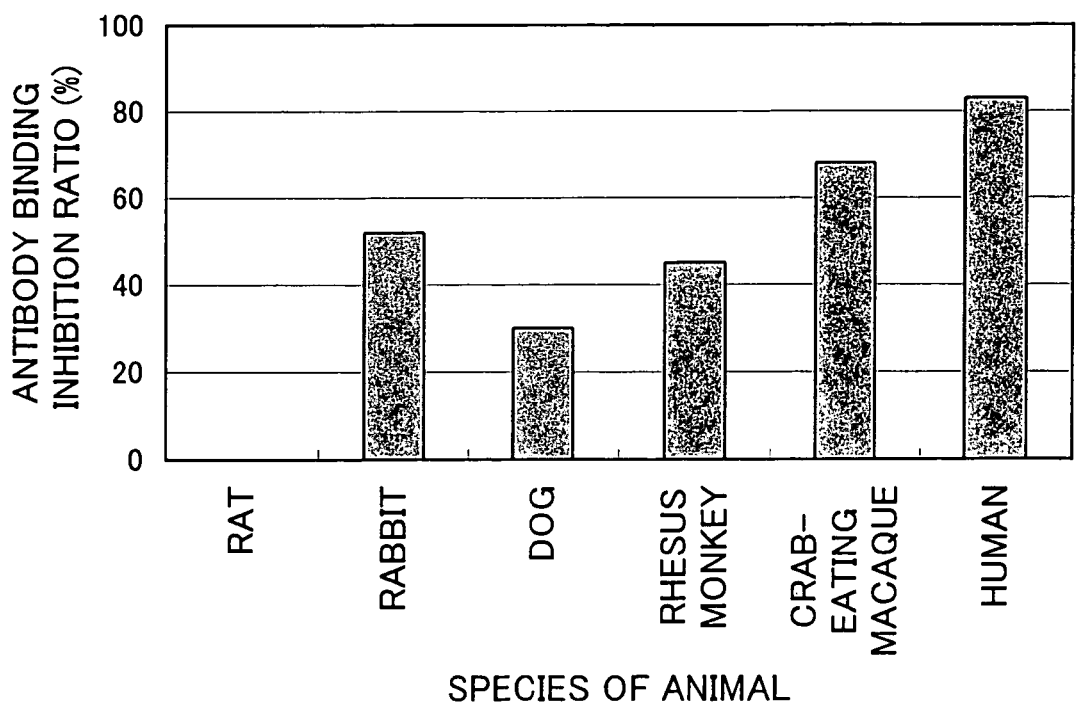
FIG. 2 is a graph illustrating cross reactivity of F1024-1-3 antibody with soluble type CD14 of dog, rhesus monkey, crab-eating monkey, rabbit or human.

Sera of dog (beagle), monkey (crab-eating macaque, rhesus monkey), rabbit (New Zealand white), human (positive control), and rat (negative control) diluted with PBS were each mixed with 1 μg/mL peroxidase-labeled F1024-1-3 antibody and the mixtures were each added to the wells of the plate from which the blocking solution had been removed. The plate was incubated at 37° C. for 1 hour and washed with a washing solution 5 times. Thereafter, a tetramethylbenzidine color developing solution containing 0.02% hydrogen peroxide was added to the wells and after 10 minutes of reaction, the reaction was terminated with 0.5 M sulfuric acid. The absorbance of the plate was measured at a wavelength of 450 nm. The results obtained with 4-fold diluted sera are shown in FIG. 2.

As a result, inhibition ratios of binding of F1024-1-3 antibody to human CD14 were 52% for rabbit, 30% for dog, 44% for rhesus monkey, 57% for crab-eating macaque, and 83% for human, so that it was found that F1024-1-3 antibody shows cross reactivity with CD14s of rabbit, dog, and monkey.

Next, binding of F1024-1-3 antibody to rabbit CD14 was studied by using a flow cytometric method.

From an ear artery of a male rabbit (New Zealand white, Kitayama Labes) weighing 2.2 kg, 1 mL of rabbit whole blood was collected by using a syringe wetted with heparin. To 100 μL of this was added 10 mL of a Tris/$NH_4Cl$ solution to cause hemolysis and the remaining cell fractions were recovered by centrifugation. The collected cells were blocked with 5% bovine serum/0.1% EDTA/$PBS^-$ and centrifuged again to recover cells.

Then, the cells were suspended in 1 mL of 5% bovine serum/0.1% EDTA/$PBS^-$ and F1024-1-3 antibody, F1024-1-3 antibody preincubated with 275 ng of human CD14(1-356), and rat IgG were added each in a final concentration of 1 μg/mL, the mixtures were allowed to react at 4° C. for 1 hour. Each cell suspension was washed 3 times with 0.25% bovine serum/PBS and suspended again in 1000-fold diluted FITC-labeled anti-rat antibody (DAKO) and allowed to react at 4° C. for 30 minutes. Again, the cells were washed, FACS analysis was performed by using FACS Calibur (BD Co.), and the intensity of fluorescence was measured.

Figure 3:
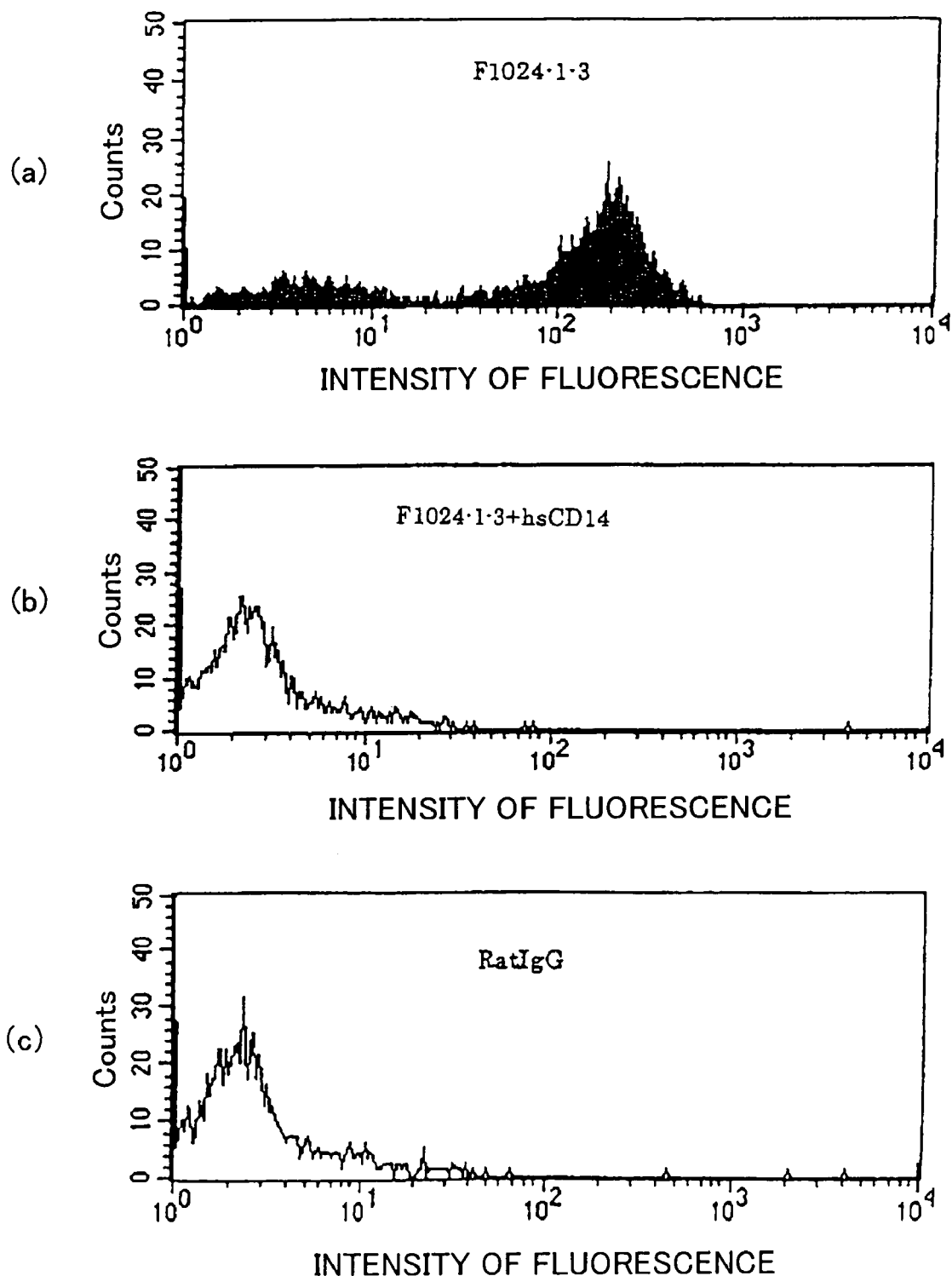
FIG. 3 comprised of graphs (a) to (c), illustrating results of study on binding of F1024-1-3 antibody to rabbit CD14 by means of a fluorocytometry method.

As shown in FIG. 3, rabbit monocytes were stained with F1024-1-3 antibody and this staining was inhibited by pretreatment with human CD14. Further, no staining occurred with control antibody (rat IgG). Therefore, it was confirmed that F1024-1-3 antibody binds to rabbit CD14 on monocytes.

Example 4

IL-6 Production Inhibiting Activity of F1024-1-3 Antibody.

Human vascular endothelial cells HUVEC (Sanko Pure Chemicals Co., Ltd.) were peeled with $PBS^-$ containing 0.05% trypsin and 0.53 mM EDTA and then suspended in RPMI1640 medium (Asahi Techno Glass Co., Ltd.) containing 2% serum prepared by removing soluble type CD14 from serum from a healthy person with an anti-CD14 antibody (hereinafter, referred to as 2% CD14w/oHS/RPMI) and inoculated in wells of a 96-well plate in a density of $5 \times 10^4$ cells/well (50 μL/well), followed by cultivation for 24 hours under the conditions of 37° C. and 5% $CO_2$.

10 μL of RPMI 1640 medium containing 14% of the human serum from which soluble type CD14 had been removed, 10 μL of 120 ng/mL LPS (*E. coli* 055:B5, Difco Co.), 10 μL of 3.6 μg/mL serum-derived soluble type CD14 and 40 μL of 900 ng/mL F1024-1-3 antibody or 3C10 antibody were added to the cells. The resulting mixture was cultivated for 20 hours and then IL-6 in the supernatant was measured by using human IL-6 EIA kit (PE Biosystems Co.).

Measurement of IL-6 was performed according to the protocol attached to the human IL-6 EIA kit. That is, 100 μL of supernatant was transferred to an IL-6 antibody-immobilized plate and incubated at 37° C. for 60 minutes. Thereafter, the reaction mixture was removed and the plate was washed 4 times with 400 μL/well Wash Buffer 2 and then 100 μL/well of anti-human IL-6 antibody was added to the plate, which was incubated at 37° C. for 30 minutes. The reaction mixture was removed and the plate was washed 4 times with 400 μL/well Wash Buffer 2 and then 100 μL/well of a solution of peroxidase-labeled streptoavidine was added to the plate, which was incubated at 37° C. for 30 minutes.

After washing, 100 μL/well of a color developing substrate (TMB) was added and the mixture was reacted at room temperature for 15 minutes and then the reaction was stopped by addition of 100 μL/well of a stop solution. The absorbance at a wavelength of 450 nm was measured and the production amount of IL-6 in the sample was calculated. Note that rat IgG and 3C10 antibody used as control antibodies were purified preparations.

Figure 4:
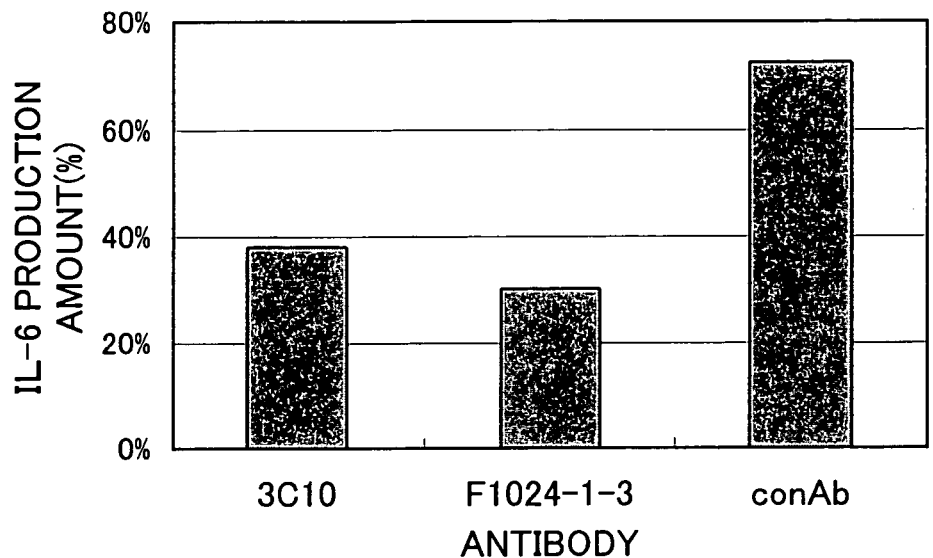
FIG. 4 is a graph illustrating the effect of F1024-1-3 antibody to suppress IL-6 production in endothelial cells through LPS/CD14. The bar "conAb" indicates a rat IgG as control.

The results obtained are shown in FIG. 4. The production amount of IL-6 when no antibody was added was taken as 100%. IL-6 production inhibiting activity was observed in F1024-1-3 antibody and 3C10 antibody. At 0.3 μg/mL, F1024-1-3 antibody inhibited the production by 60% or more. The inhibition of 3C10 antibody is weaker than F1024-1-3 antibody. This indicates that F1024-1-3 antibody is superior to 3C10 antibody in the effect of inhibiting inflammatory cytokine production in endothelial cells.

Also, it was found that the substance selected by the screening in Example 1 actually suppresses cytokines in the cells.

Example 5

[Measurement of Inhibition of IL-6 Production After Formation of LPS/CD14 Complex by F1024-1-3 Antibody]

In the same manner as in Example 4, human vascular endothelial cells HUVEC (Sanko Pure Chemicals Co., Ltd.) were suspended and inoculated in wells of a 96-well plate in a density of $5 \times 10^4$ cells/well (50 μL/well), followed by cultivation under the conditions of 37° C. and 5% $CO_2$ for 24 hours. 10 μL of RPMI1640 medium containing 14% of the human serum from which soluble type CD14 had been removed, 10 μL of 120 ng/mL LPS (*E. coli* 055:B5, Difco Co.), and 10 μL of 3.6 μg/mL serum-derived soluble type CD14 were mixed together and incubated at 37° C. for 1 hour to form LPS/CD14 complex. Thereafter, 40 μL of 900 ng/mL F1024-1-3 antibody or 3C10 antibody was added to the LPS/CD14 mixture and the mixture thus obtained was added to the cells. After further 20 hours' cultivation, the IL-6 in the culture supernatant was measured by using human IL-6 EIA kit (PE Biosystems Co.).

Measurement of IL-6 was performed according to the protocol attached to the human IL-6 EIA kit. Note that rat IgG and 3C10 antibody used as control antibodies were purified preparations.

Figure 5:
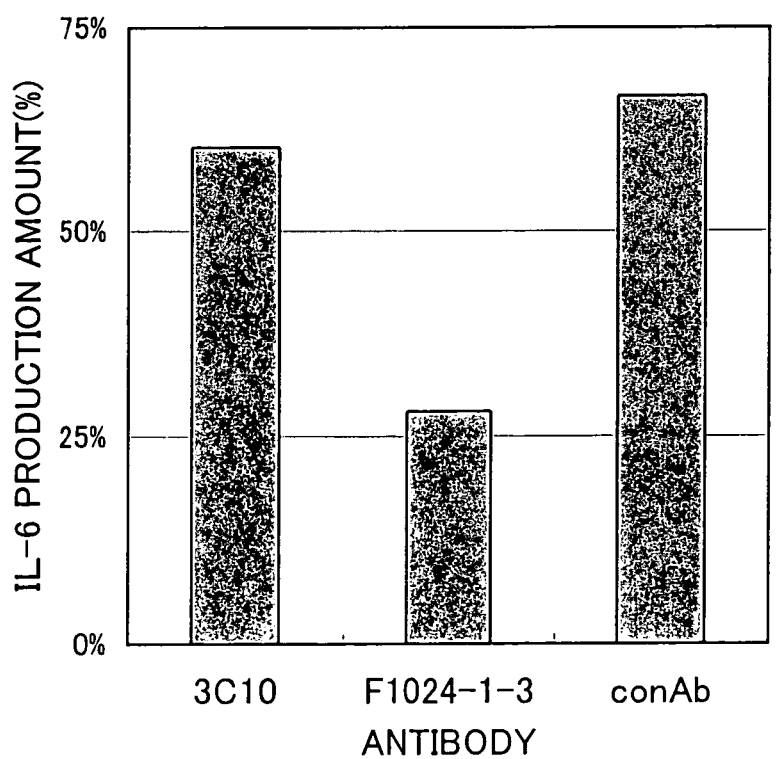
FIG. 5 is a chart illustrating the effect of F1024-1-3 antibody to suppress IL-6 production in endothelial cells after the formation of LPS/CD14 complex.

The results obtained are shown in FIG. 5. The production amount of IL-6 when no antibody was added was taken as 100%. IL-6 production inhibiting activity was observed in F1024-1-3 antibody while in the case of 3C10 antibody this activity was at the same level as the control antibody and after formation of LPS/CD14 complex no effect of inhibiting IL-6 production was observed. These indicate that F1024-1-3 antibody has the effect of inhibiting inflammatory cytokine production even after formation of LPS/CD14 complex in endothelial cells; therefore, it meets expectation that it has the effect of improving the symptoms of even those patients in whom LPS has already invaded, i.e., those patients who have been judged to suffer from sepsis.

Example 6

[Test of Binding of F1024-1-3 Antibody to LPS/CD14 Complex]

The influence of anti-CD14 antibody on the binding between CD14 and LPS on a cell membrane was analyzed by a flow cytometry method.

Human monocyte cell line THP-1 was cultured with 40 ng/mL of 1α, 25-dihydroxyvitamin D3 (Funakoshi Co., Ltd.) for 48 hours to induce differentiation and then incubated in a medium (RPMI1640 containing 10% FBS) containing or not containing 10 µg/mL of anti-CD14 antibody (3C10 or F1024-1-3 antibody) at 37° C. for 30 minutes. Thereafter, FITC-labeled LPS (Sigma Co.) was added in a final concentration of 1 ng/mL, followed by further incubation at 37° C. for 15 minutes. Immediately thereafter, the equal volume of ice-cooled RPMI1640 medium was added and the intensity of fluorescence was measured by using FACS Calibur (BD Co.).

Figure 6:
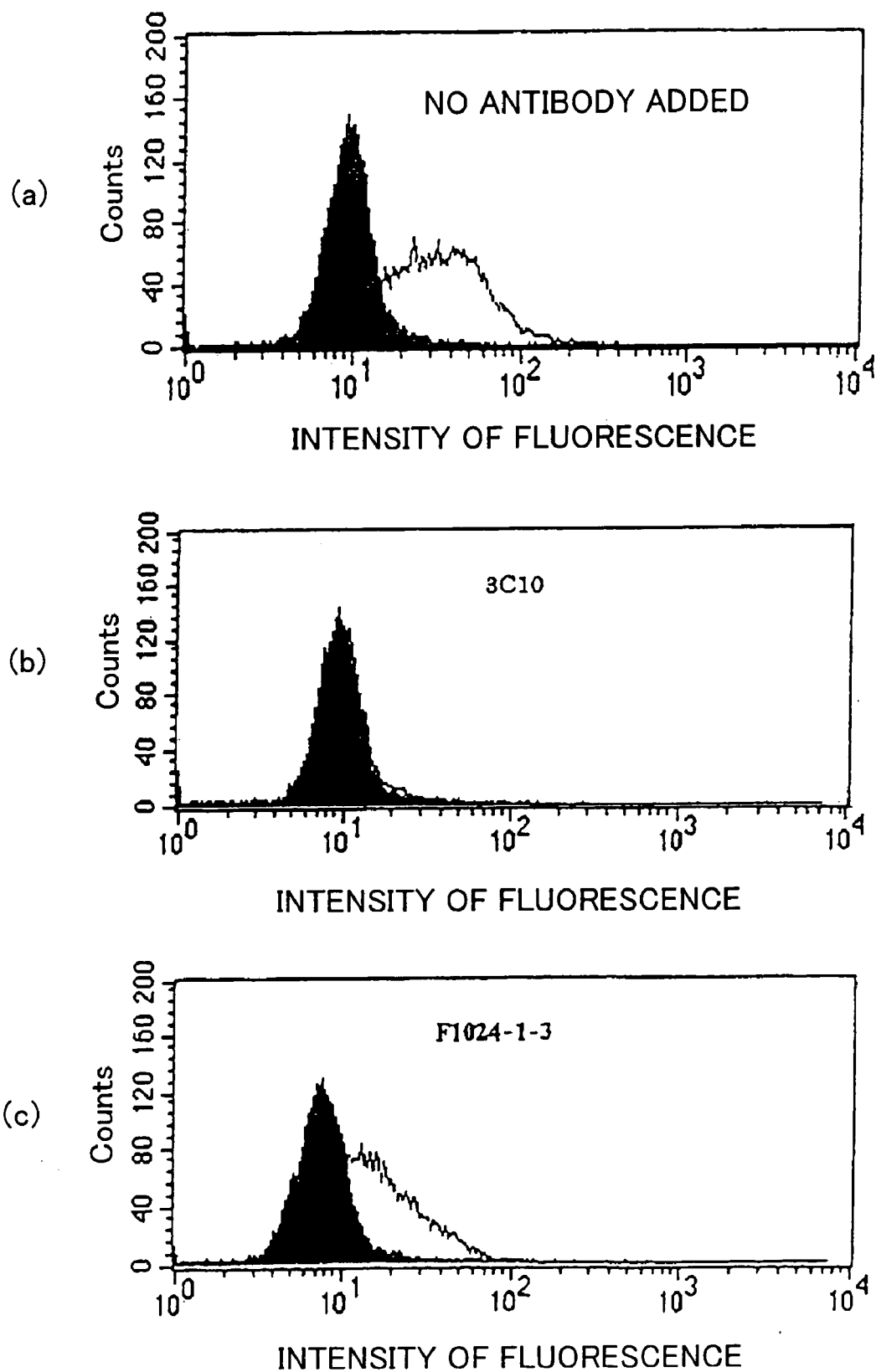
FIG. 6 comprised of graphs (a) to (c), illustrating the result of the test concerning the binding of FITC-LPS to CD14 expressing cells that F1024-1-3 antibody does not inhibit the binding.

The results obtained are shown in FIG. 6. As shown in FIG. 6, specific fluorescence observed as a result of the binding of LPS to CD14 was completely suppressed by 3C10 antibody. In contrast, F1024-1-3 suppressed it only partly, which indicates that F1024-1-3 antibody does not suppress the binding of LPS to CD14.

Example 7

IL-6 Production Inhibitory Activity Induced by Gram-Positive Bacterial Cell Component Human kidney-derived cell line U-373MG (ATCC) was scraped with PBS⁻ containing 0.05% Trypsin and 0.53 mM EDTA, then suspended in RPMI1640 medium (Asahi Techno Glass Co., Ltd.), and inoculated in wells of a 96-well plate in a density of $3\times10^4$ cells/well (100 mL/well), followed by culture under the conditions of 37° C. and 5% $CO_2$ for 24 hours. Then, 70 µL of RPMI1640 medium, 10 µL of 1 µg/mL (w/v) Staphylococcus aureus cell suspension (Sigma Co.), 10 µL of 5 µg/mL sCD14(1-356) and 10 µL of F1024-1-3 antibody were added to each well. After additional 20 hours of culture, IL-6 in the supernatant of culture was measured by using human IL-6 EIA kit (IL-6 Eli-pair: GIBCO BRL Co.). As a control, sCD14(1-356) was added instead of CD14 mutant polypeptide or F1024-1-3 antibody.

Measurement of IL-6 was performed according to the protocol attached to the human IL-6 EIA kit. That is, 50 µL of the culture supernatant diluted with 1% (w/v) BSA/PBS (−) 4 folds was transferred to an IL-6 antibody immobilized plate and 50 µL of biotinated anti-human IL-6 antibody was added thereto. After 60 minutes of incubation at 37° C., the reaction mixture was discarded and the wells were washed 3 times with 400 µL/well 0.05% (v/v) Tween-20/PBS(−). 100 µL/well of a peroxidase-labeled streptoavidin solution was added to wells and further incubated at 37° C. for 20 minutes. After washing, 100 µL/well of a color developing substrate (TMB) was added and allowed to react at room temperature for 15 minutes. Then 100 µL/well of a stop solution (1 M HCl) was added to terminate the reaction. The absorbance at a wavelength of 450 nm was measured and the amount of produced IL-6 in the sample was calculated.

F1024-1-3 antibody had IL-6 production inhibitory activity of 55.2%.

The results indicate that F1024-1-3 suppress cytokine production induced by gram-positive bacteria cell component.

Example 8

Effectiveness of F1024-1-3 Antibody in an LPS-Loaded Rabbit Sepsis Model.

For the purpose of confirming effectiveness of F10241-3 antibody in a sepsis model, an LPS-loaded rabbit sepsis model was prepared and effectiveness of F1024-1-3 antibody therein was studied by two kinds of protocols of pre-administration and post-administration of antibody.

[Pre-Administration Effect of F1024-1-3 Antibody]

(1) Administration Prior to LPS

The LPS-loaded rabbit sepsis model was prepared by administering 5 µg/kg of LPS (Salmonella minnesota Re595, Sigma Co.) to a New Zealand white rabbit (2.1 to 2.4 kg, Kitayama Labes) through ear vein at the time 0 and 5 and 24 hours later in conformance with the method of Schimke et al. (Proc. Natl. Acad. Sci. USA, 95:13875, 1998). The protocol for pre-administration group was to administer 2.5 mg/kg of F1024-1-3 antibody through the ear vein 1 hour before and 4 and 23 hours later. To the control group was administered a physiological saline instead of the antibody.

First, the rabbits were grouped by body weight and 5 rabbits were selected for each group. Preliminary blood collection was performed 1 hour before. Then, 1, 3, 5, 7, 23, 25, 28 and 48 hours later, collected the blood and body weight, number of leukocytes, serum GPT value, serum creatinine value, and serum TNFα value were measured. Note that the number of leukocytes was counted by using Sysmex F-280 (To a Medical Electronics) and serum GPT value and serum creatinine value were measured by using DriChem5000 (FUJI FILM).

Further, TNFα was obtained in conformance with the method of David et al. (Journal of Immunological Methods, 68:167, 1984). That is, L929 cells (ATCC) were scraped with 0.25% trypsin/PBS⁻, resuspended to $5.5\times10^5$ cells/mL, and inoculated in wells of a plate in a density of $5.5\times10^4$ cells/well. After culturing overnight under the conditions of 37° C. and 5% $CO_2$, the supernatant was discarded, 100 µL of a TNF standard preparation (human TNF, Mochida) or diluted analyte was added, subsequently actinomycin D (Sigma) was added to a final concentration of 5 µg/mL, and the cells were cultured under the conditions of 37° C. and 5% $CO_2$ for 20 hours.

The amount of TNF was determined as follows. That is, after removing 100 µL of the supernatant of culture in each well of the plate, adding 10 µL of a WST-1 solution (Dojin Chemical), incubating the mixture at 37° C. for 40 to 90 minutes, and then measuring the absorbance at 450 nm. The amount of TNF in serum produced was shown as a relative value of absorbance. Further, The effectiveness of F1024-1-3 antibody was judged by survival rate after 48 hours.

Summary is shown in Table 1. As a result, the group to which F1024-1-3 antibody was administered had a survival rate after 48 hours of 100% (5/5) while the group to which the physiological saline was administered had a survival rate of 40% (2/5), which indicates that the survival rate is significantly improved by administration of F1024-1-3 antibody. In addition, as for the value of each parameter after 28 hours, the F1024-1-3 antibody-administered group showed values closer to the pre-values than the saline-administered group.

Figure 7:
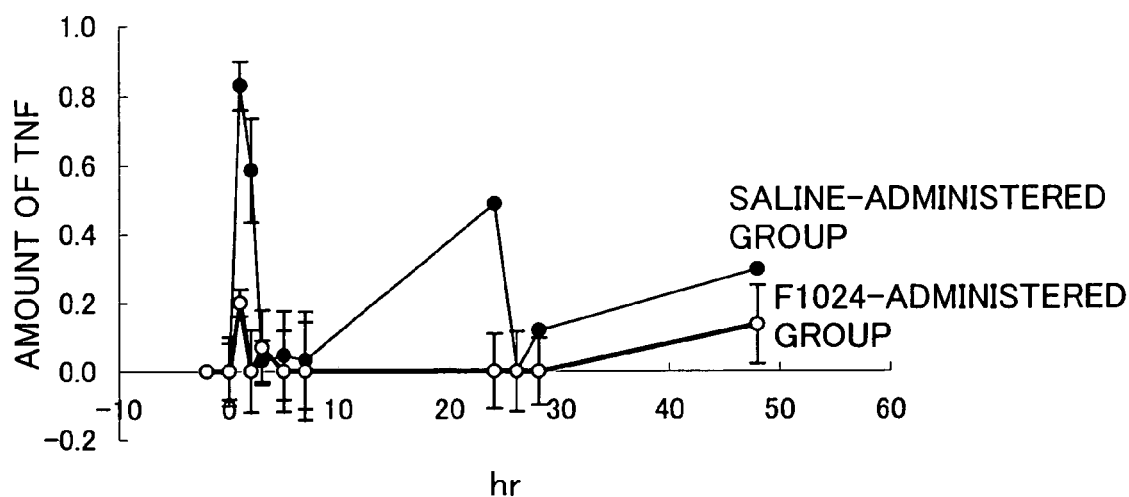
FIG. 7 is a diagram illustrating suppression of production of TNF by pre-administration of F1024-13 antibody in an LPS-loaded rabbit sepsis model.

Furthermore, it has become evident that as shown in FIG. 7, administration of F1024-1-3 antibody suppressed the production of TNF in serum and F1024-1-3 antibody suppressed production of inflammatory cytokines in vivo like in vitro.

Table 1 shows improvement in mortality and improvements in various parameters by pre-administration of F1024-1-3 antibody in an LPS-loaded rabbit sepsis model.

TABLE 1

|  | Pre-value (n = 10) | F1024-1-3 antibody-administered group | Saline-administered group |
|---|---|---|---|
| Survival rate after 48 hours (%) | — | 100% | 40% |
| Parameter after 28 hours | | | |
| Number of leucocytes ($10^3$/mm$^3$) | 6.6 +/− 0.7 | 8.2 +/− 2.7 | 2.1 |
| GPT (U/L) | 27 +/− 8 | 82 +/− 42 | 231 |
| Creatinine (mg/dL) | 0.8 +/− 0.04 | 0.78 +/− 0.04 | 1.4 |
| Body weight after 48 hours (kg) | 2.4 +/− 0.04 | 2.35 +/− 0.02 | 2.07 |

Further, for the purpose of confirming the effect of F1024-1-3 antibody on gram-positive bacteria, LTA/PepG was administered instead of LPS to study the effect of F1024-1-3 antibody to improve leukocytopenia. That is, F1024-1-3 antibody (2.5 mg/kg) or a physiological saline was administered to New Zealand white (2.1 to 2.4 kg, Kitayama Labes), and 1 hour after the administration, LTA (Sigma) and PepG (Fluka) in 160 µg/mL were administered through ear vein.

Figure 8:
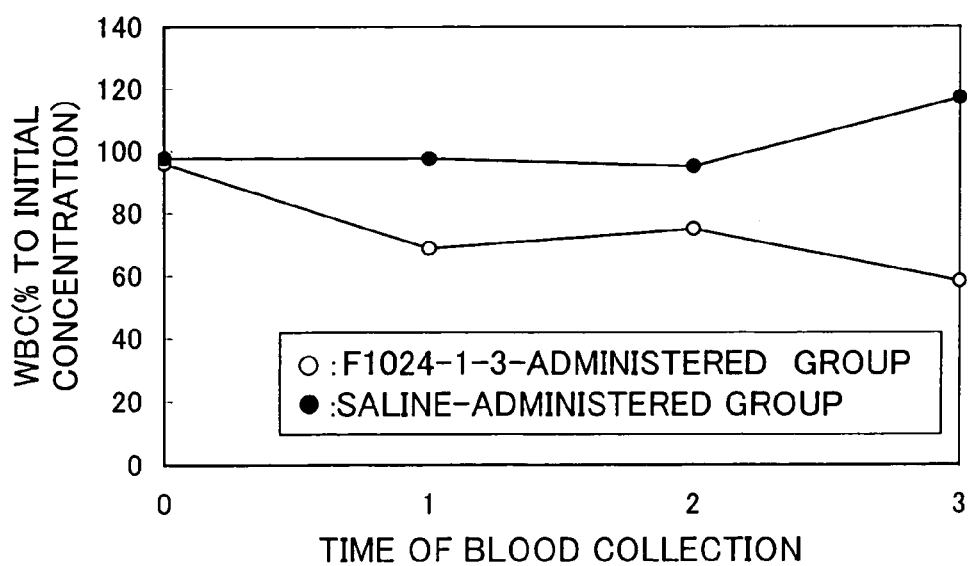
FIG. 8 is a diagram illustrating improvement of leukocytopenia by pre-administration of F1024-1-3 antibody in an LTA/PepG-administered rabbit sepsis model.

The time immediately before the administration of LTA/PepG was defined as 0 hour and every hour thereafter blood was collected to count the number of leukocytes therein. As a result, as shown in FIG. 8, a decrease in the number of leukocytes was observed in the saline-administered group while no decrease in the number of leukocyte was observed in the F1024-1-3 antibody-administered group. This confirms that F1024-1-3 antibody is effective to leukocytopenia due to LTA/PepG and its effectiveness to sepsis caused by gram-positive bacteria was confirmed.

(2) [Post-Administration Effect of F1024-1-3 Antibody]

According to the method in (1) above, an LPS-loaded rabbit sepsis model was prepared. The protocol for post-administration group was as follows. That is, 2.5 mg/kg of F1024-1-3 antibody was administered through the ear vein 4 and 23 hours later. To the control group was administered a physiological saline instead of the antibody.

First, preliminary blood extraction from rabbits grouped in the same manner as above was performed on selected 5 animals per group 1 hour before. Then, LPS was administered according to the protocol and 1, 3, 5, 7, 24, 26, 28 and 48 hours later, blood extraction was conducted and body weight, number of leukocytes, serum GPT value, and serum creatinine value were measured in the same manner as above.

Figure 9:
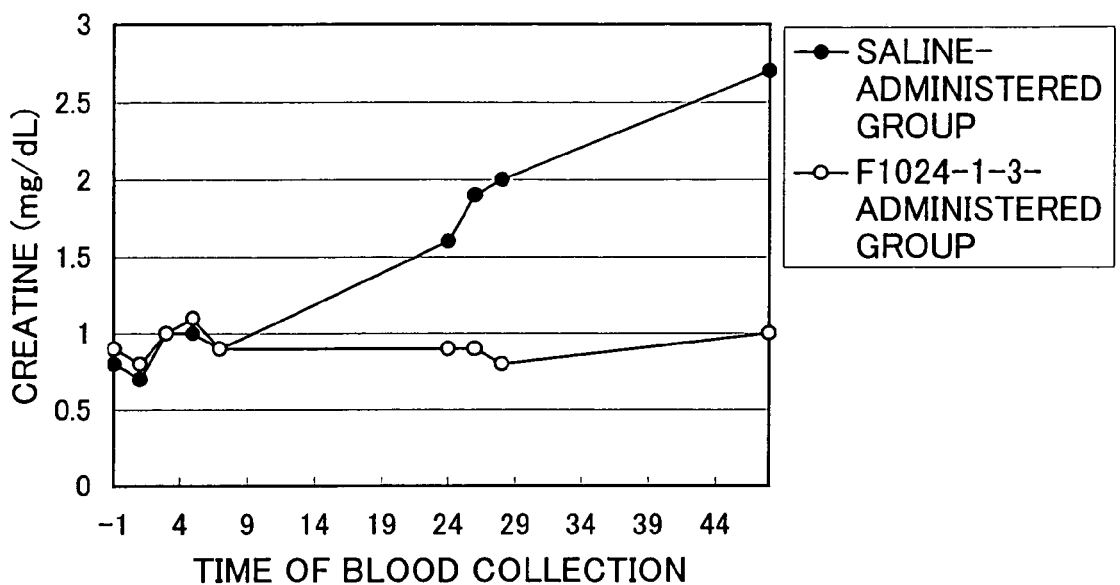
FIG. 9 is a diagram illustrating improvements of values of ALT and creatinine by post-administration of F1024-1-3 antibody in an LPS-loaded rabbit sepsis model. White circles indicate an antibody-administered group and black circles indicate saline-administered group.

A summary is shown in Table 2. As a result, the group to which F1024-1-3 antibody was administered had a survival rate after 48 hours of 100% (5/5) while the group to which the physiological saline was administered had a survival rate of 80% (4/5), which indicates that no significant difference in survival rate was observed between these groups. However, as for various parameters after 28 hours, the F1024-1-3-administered group had values close to normal values. On the other hand, the saline-administered group had extraordinary values indicative of damages of cells. Further, as shown in FIG. 9, the level of creatinine in serum did not fluctuate greatly during observation of the progress, so that it was confirmed that F1024-1-3 antibody had an effect of suppressing damages of tissue caused by LPS loading.

Table 2 shows improvement of various parameters by post-administration of F1024-1-3 antibody in an LPS-loaded rabbit sepsis model.

TABLE 2

|  | Pre-value (n = 10) | F1024-1-3 antibody-administered group | Saline-administered group |
|---|---|---|---|
| Survival rate after 48 hours (%) | — | 100% | 80% |
| Parameter after 28 hours | | | |
| Number of leucocytes ($10^3$/mm$^3$) | 6.6 +/− 0.4 | 5.3 +/− 0.7 | 1.6 +/− 0.3 |
| GPT (U/L) | 27 +/− 8 | 41 +/− 22 | 22 +/− 13 |
| Creatinine (mg/dL) | 0.8 +/− 0.04 | 0.82 +/− 0.09 | 2.04 +/− 1.07 |
| Body weight after 48 hours (kg) | 2.13 +/− 0.08 | 1.98 +/− 0.1 | 1.92 +/− 0.06 |

Example 9

Analysis of Inhibition Mechanism by Using a Molecular Interactions Analyzer (1) [Preparation of Monoclonal Antibody Which is Specific to CD14 Protein Having a High Molecular Weight of 49 kDa]

[1] Preparation of a Peptide Specific to a CD14 Protein Having a High Molecular Weight of 49 kDa The sequence consisting of amino acids at positions 316 to 328 described in SEQ ID NO:1 was selected as a CD14-specific peptide having a high molecular weight of 49 kDa for use in immunization (hereinafter referred to as peptide 13).

Note that cystein was inserted at the C-terminal in order to bind the selected peptide to a carrier protein through an SH group at the C-terminal. The synthesis of peptide was performed by using ABI432A peptide synthesizer (Applied). The peptide was cut out from the resin by a conventional method and the peptide was purified by using C18 reverse phase HPLC (CAPCELL-Pak, Shiseido).

[2] Preparation of a Peptide Carrier Antigen by Using the Synthetic Peptide

The peptide prepared in [1] was dissolved in distilled water to 10 mg/mL, and the solution was mixed with maleimidated keyhole limpet hemocyanin (KLH, PIERCE) in equal proportions. After 2 hours of reaction at room temperature, the reaction mixture was desalted through NAP-10 column (Pharmacia) to obtain peptide 13 carrier antigen (hereinafter, referred to as peptide 13-KLH). As for the concentration of the protein, the value obtained by dividing the volume of KLH used by the volume of the solution was used.

[3] Preparation of Monoclinal Antibody Which is Specific to CD14 Protein Having a High Molecular Weight of 49 kDa Cell fusion was performed in the same manner as in Example 1(1) by using 100 µg of peptide 13-KLH as an immunogen. Hybridomas were selected in HAT medium (GIBCO) and after 1 week, screening of hybridomas producing antibodies that react with a recombinant human CD14 protein was performed.

First, the purified recombinant human CD14 protein was diluted with 0.01 M carbonate buffer solution (pH 9.5) to 1 µg/mL, and 50 µL aliquot was added to each well of Immuno-plate (Maxisorb, NUNC). After 1 hour of reaction at 37° C., the wells were washed 5 times with deionized water and 100 µL of PBS containing 0.5% BSA was added to each well to effect blocking. Then, the supernatants sampled from the cultures of the selected hybridomas were added in wells, respectively, and reacted at 37° C. for 1 hour. Then, the wells were washed 3 times with physiological saline containing 0.05% Tween 20. Peroxidase-labeled anti-rat immunoglobulins antibody (DAKO) diluted 1,000 folds with PBS containing 10% rabbit serum was added to each well in an amount of 50 µL. After 1 hour's reaction at 37° C., the wells were similarly washed 5 times and tetramethylbenzidine solution containing 0.01% hydrogen peroxide was added to each well. After 10 minutes of reaction at room temperature, the reaction was stopped by a 0.5 M sulfuric acid solution and the absorbance was measured at 450 nm by using a plate spectrophotometer (NJ-2100, Japan Intermed). As a result, the well containing the hybridoma that reacted with CD14 protein having a high molecular weight (F1025-4-1) was selected and cloning was performed by a limiting dilution method.

The selected hybridoma was cultured in 10% FCS/RPMI1640 medium (GIBCO) and then cultured in Hybridoma-SFM medium (GIBCO) to produce an antibody, which was purified by using Prosep-G column (Bioprocessing). The subtype of the purified F1025-4-1 antibody revealed to be rat IgG1/K.

[4] Preparation of HRP-Labeled Antibody

To 0.5 mg of a peroxidase (Toyobo) solution in distilled water was added a solution of 100 mM periodic acid in distilled water and the mixture was allowed to react at 25° C. for 20 minutes. After completion of the reaction, 1.5% of ethylene glycol was added and after 10 minutes of reaction at 25° C., the reaction mixture was dialyzed against a 1 mM acetate buffer solution (pH 4.4). The purified F1025-4-1 antibody was dialyzed against a 10 mM carbonate buffer solution (pH 9.5) and 0.5 mg of peroxidase activated by addition of 0.5 mg of 1 M carbonate buffer solution (pH 9.5) was mixed with each antibody in equal proportions and the mixture was allowed to react at 25° C. for 2 hours. 4 mg/mL sodium borohydride was added to the reaction mixture and 2 hours of reaction was performed at 4° C. The reaction mixture was dialyzed against PBS to obtain a peroxidase-labeled antibody. The amount of liquid was measured and the concentration of antibody was calculated from the amount of antibody used.

(2) [Analysis of Mechanism of Inhibition by F1024-1-3 Antibody]

[1] Expression of Recombinant TLR4

COS-1 cells (ATCC: CRL1150) were inoculated in a density of $3 \times 10^5$ cells/75 cm$^2$ of flask and cultured for 24 hours under the conditions of 37° C. and 5% $CO_2$. On the day next, the plasmid pcDNAT4 described in Example 2(1) was mixed with the cells in proportions of 6.25 µg DNA: 25 µL FuGENE6 according to the protocol described in FuGENE6 (Roche) and the mixture was added to a flask containing 15 mL of 1% FBS/DMEM (Sigma, high glucose) and cultured under the conditions of 37° C. and 5% $CO_2$ for 48 hours. COS-1 cells manipulated in the same manner as above except that no plasmid was contained were used as negative control. Supernatants of cultures of COS-1 cells expressing TLR4 molecules on the cell membrane thereof (hereinafter, referred to as TLR4-COS) and COS-1 cells expressing no TLR4 molecule on the cell membrane thereof were discarded and the cells were washed twice with PBS$^-$ (Sigma). Then, 5 mL of a 1% EDTA/PBS$^-$ solution was added thereto and lightly stirred. Thereafter, the cells were scraped off from the culture flask by using cell scraper (COSTAR) and recovered in a 50 mL centrifuge tube. The flask was further washed with 5 mL of PBS$^-$ and added in a 50-mL centrifuge tube, which was centrifuged at 1,000 rpm for 10 minutes to settle the cells, and then the supernatant was discarded. Further, the cells were washed twice with PBS$^-$. Then, the washed cells were filtered through a 40-µm mesh cell strainer (FALCON) and the number of cells was counted. The cells were centrifuged once again and diluted with PBS$^-$ to $5 \times 10^5$ cells/mL and stored at 4° C.

[2] Preparation of Anti-FITC Antibody-Immobilized Chip

In order to immobilize anti-FITC monoclonal antibody (OEM concept Co.) to cells on a chip for use in the analysis of BIACORE3000 (BIACORE Co.), the cells were activated with a NHS/EDC solution (BIACORE Co.) for 7 minutes according to the manual provided by BIACORE Co. and then an antibody diluted with a pH 6.0 acetate buffer solution to 50 µg/mL was added to the cells by a manual injection method to immobilize the antibody, followed by blocking with ethanolamine. As the reference, non-treated cells were used.

[3] Preparation of FITC-LPS/CD14 Complex

FITC-LPS (Sigma, Serotype0111:B4) diluted with PBS$^-$ pH 7.4) to 6 µg/mL and 300 µg/mL of recombinant sCD14 (1-356) prepared above were mixed in the proportion of 1:1 and the mixture was allowed to stand at 37° C. for 30 minutes to form a complex. The formation of a complex was confirmed by an ELISA system using an anti-FITC antibody-immobilized plate and the peroxidase-labeled anti-CD14 antibody (F10254-1) prepared in (1) above. That is, the anti-FITC antibody was immobilized to the plate in a concentration of 10 µg/mL and blocked with 0.5% bovine serum albumin/PBS$^-$. Then, the prepared FITC-LPS/CD14 complex, FITC-LPS, and sCD14 were added to antibody-immobilized wells and allowed to react at 37° C. for 1 hour. After washing each well, the peroxidase-labeled anti-CD14 antibody diluted to 1 µg/mL was added to each well, followed by reaction. After washing, the product was reacted with a TMB color developing substrate solution (BioFix, Funakoshi), and at a stage where an appropriate color developing was obtained, the reaction was stopped with sulfuric acid and the absorbance was measured at 450 nm. As a result, FITC-LPS and sCD14 alone resulted no increase in absorbance while only when FITC-LPS/CD14 complex was present, the absorbance increased, which confirmed formation of a complex.

[4] Analysis of Inhibition Mechanism

Figure 10:
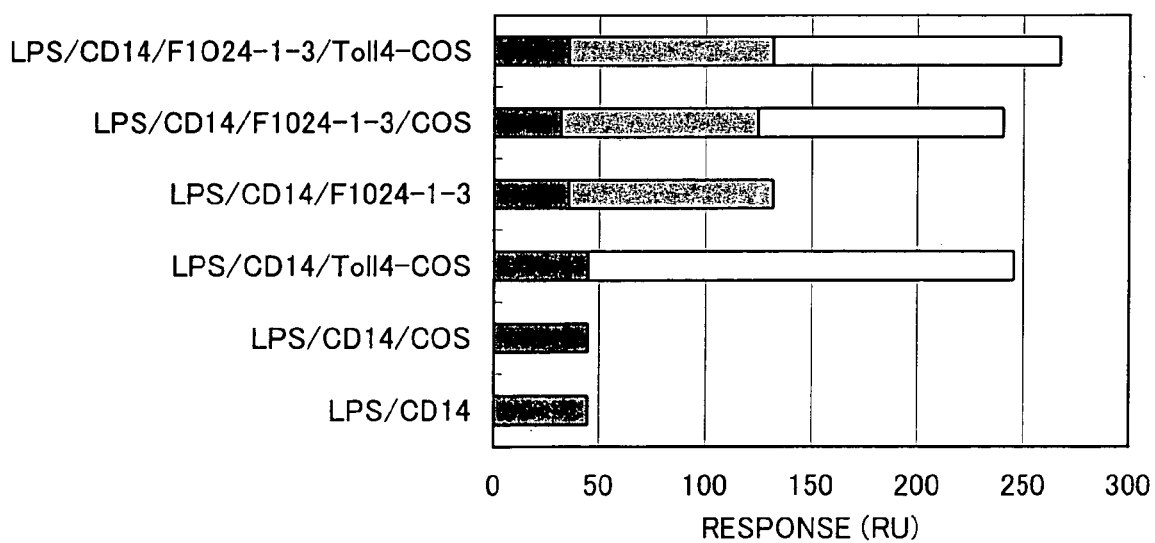
FIG. 10 is a diagram illustrating the binding amount when forming LPS/CD14/TLR4-COS complex by using BIACORE 3000 and the inhibition of F1024-1-3 antibody when TLR4-COS binding to LPS/CD14. Response is an index by BIACORE Co., with a graph of 1,000 RU indicating a binding amount of 1.2 ng.

The prepared FITC-LPS/CD14 complex was immobilized on the chip and then F1024-1-3 antibody diluted with HBS-EP buffer solution to 130 µg/mL was injected to bind the antibody to the immobilized CD14. Then, TLR4-COS cells and COS cells as control were injected and binding amounts of TLR4-COS cells and COS cells were measured. The results obtained are shown in FIG. 10, in which the heights of the bar charts indicate binding amounts of complexes onto the cells on the tip. That is, an increase in response was observed by immobilizing of LPS/CD14 complex to the cells on the tip. Next, since no response was observed in COS cells, no binding was confirmed. On the other hand, in TOLL4-COS cells, an increase in response (200 RU) was observed and hence binding was confirmed. When LPS/CD14 was reacted with an antibody, an increase in response was similarly observed and binding was confirmed. Further, when COS cells and TOLL4-COS cells were allowed to react, increases in response were observed in both cases (136 RU in TOLL4-COS cells and 115 RU in COS cells). Since the increase in response in COS cells was attributable to nonspecific binding between the cell and antibody, the inhibition rate was 90%. This indicates that binding of F1024-1-3 antibody to CD14 inhibited the binding between TLR4 and CD14, so that it has become evident that the suppression mechanism of F1024-1-3 antibody involves inhibition of binding of TLR4 to CD14. Inhibition rate was calculated by [(Response of TLR4-COS(TOLL4-COS) cells without F1024-1-3 antibody)−{(Response of TOLL4-COS cells when F1024-1-3 antibody is bound)−(Response of COS cells when F1024-1-3 antibody is bound)}]/(Response of TOLL4-COS cells without F1024-1-3 antibody)×100 (%)

Example 10

Figure 11:
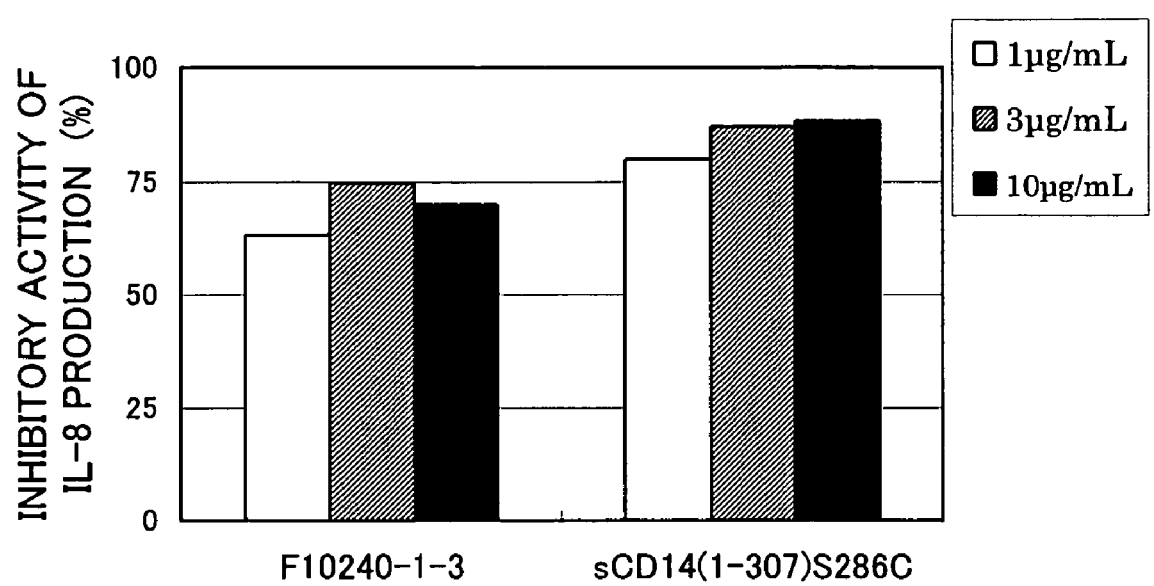
FIG. 11 is a graph illustrating the inhibition effect of F1024-1-3 and sCD14(1-307)S286C to induced the production of IL-8 in HEKT4-14.

Tests on Inhibition of Cytokine Production in Human TLR4 Expression Transformant Cell Line HEKT4-14 obtained in Example 2(1) was inoculated in wells of a 24-well plate in a density of $0.8 \times 10^5$ cells/well and was stimulated with LPS/sCD14 in the presence or absence of F1024-1-3 or sCD14(1-307)S286C obtained by Example 11 which will be described herein below in the same manner as in Example 2(2). After 20 hours, the supernatant of culture was recovered and the amount of produced IL-8 was confirmed by EIA. As a result, both F1024-1-3 and sCD14(1-307)S286C showed suppressive activity, in does-dependent manner (FIG. 11).

Example 11

Analysis of the Recognition Region of F1024-1-3 Antibody.

In order to clarify the region that F1024-1-3 antibody recognizes, experiments on inhibition by peptide, experiments on binding by CD14 C-terminal deletion mutant, and experiments on binding by CD14 amino acid substitution mutant were conducted.

(1) [Preparation of CD14 Peptide]

Based on the amino acid sequence of CD14 described in SEQ ID NO:1, four peptides of peptide A (SEQ ID NO:12), peptide B (SEQ ID NO:13), peptide C (SEQ ID NO:14), peptide D (SEQ ID NO:15) and peptide E (SEQ ID NO:16) as control were synthesized. That is, peptides were synthesized by using a peptide synthesizer (432A, AppliedBiosystems) according to the method of using it, deprotected and cut out according to conventional methods, and purified by HPLC by using a C18 column (CAPCELL-PAK, Shiseido). The purified fractions were recovered, freeze-dried and weighed and dissolved in distilled water to 10 mg/mL.

(2) [Preparation of CD14 Deletion Mutant with Deletion of Amino Acids of Human CD14 (Human Soluble Type CD14 Deletion Mutant)]

[1] [Construction of full-length sCD14 expression plasmid (pM1656)

First, plasmid pM1650 that expresses mCD14 in mammalian cells was constructed. An about 1.4 kb DNA fragment containing human CD14 cDNA was cleaved from plasmid pUCH14P-4 described in WO98/39438 with Xba I and HindIII and inserted into the Xba I/HindIII site of pcDNA 3.1(−) (Invitrogen Co.), which is a mammalian cell expression vector. Thereafter, *E. coli* Competent Cells (JM109 cells, TaKaRa Co.) were transformed therewith according to the attached protocol and the resulting colonies were confirmed by PCR to obtain target mCD14-expressing plasmid (pM1650).

Next, in order to have human CD14 expressed as a soluble type protein, a recombinant-expressing plasmid pM1656 with substitution of Asn at position 326 and Gly at position 328 from the N-terminal (cf. SEQ ID NO:1), which are sites necessary for GPI anchoring, by Gln and Val, respectively. That is, by using sense primer 3 (SEQ ID NO:17) and antisense primer 3 (SEQ ID NO:18) and also using the above-mentioned pM1650 as a template, PCR reaction was performed by repeating 30 times the cycle consisting of 94° C. for 30 seconds, 55° C. for 30 seconds, and 72° C. for 1 minute with TaKaRa Ex Taq (TaKaRa Co.). The amplified DNA fragment was subjected to double digestion with XhoI and ApaL I, and inserted into the XhoI/ApaL I site of pM1650. After the transformation of JM109 cells, the resulting colonies were confirmed by PCR to obtain the target sCD14-expressing plasmid (pM1656).

[2][Construction of Human Soluble Type CD14 C-Terminal Deletion Modified Polypeptide-Expressing Plasmids (pM1658 to pM1662 and pM1674 to pM1676)]

Plasmids pM1658, pM1674, pM1675, pM1676, pM1659, PM1660, PM1662 and PM1661 that express recombinants with deletion of amino acid residue at positions 49, 56, 61, 66, 71, 110, 173, and 204, respectively, from the C-terminal of CD14 (hereinafter, referred to as sCD14(1-307), sCD14(1-300), sCD14(1-295), sCD14(1-290), sCD14(1-285), sCD14(1246), sCD14(1-183), and s-CD14(1-152), respectively) in mammalian cells were constructed by the following method.

First, by using sense primer 3 and antisense primers 4, 5, 6, 7, 8, 9, 10 and 11 (SEQ ID NOs:19, 20, 21, 22, 23, 24, 25 and 26, respectively), and also using plasmid pM1656 prepared in (1) above as a template, PCR reaction was performed with Pyrobest DNA Polymerase (TaKaRa Co.) by repeating 30 times the cycle consisting of 98° C. for 10 seconds, 55° C. for 30 seconds, and 72° C. for 1 minute.

Then, the amplified DNA fragment was subjected to double digestion with XhoI and HindIII, and the products were separated and purified by 1% agarose gel electrophoresis. Also, pM1656 was digested with XhoI and HindIII and purified in the same manner as above, and the obtained an about 5.8 kb DNA fragment and the above-mentioned PCR fragment were ligated. After the transformation of JM109 cells, the resulting colonies were confirmed by PCR to obtain the target CD14 mutant polypeptide-expressing plasmids (pM1658, pM1674, pM1675, pM1676, pM1659, pM1660, pM1662 and pM1661).

[3] [Expression in COS-1 Cells]

Plasmids pM1656, pM1658 to pM1662 and pM1674 to pM1676 prepared in (1) and (2) were transfected into COS-1 cells by the following method to have sCD14(1-356), sCD14(1-307), sCD14(1-300), sCD14(1-295), sCD14(1-290), sCD14(1-285), sCD14(1-246), sCD14(1-183) and-sCD14(1-152) expressed therein. That is, 50 μL of FuGENE6 (Roche Diagnostics Co.) was mixed with 12.5 μg of each of the above-mentioned plasmid DNAs according to the attached protocol, and the mixtures were each added to COS-1 cells semi-confluently grown in 150 cm² flask. After culturing the cells under the conditions of 5% $CO_2$ and 37° C. for 72 hours, the supernatants were recovered to obtain the target CD14 mutant polypeptides.

The expression amount of CD14 mutant polypeptides was measured by EIA with anti-human CD14 antibody. That is, anti-CD14 antibody MEM-18 (MONSANT Co.) diluted 200 folds with 10 mM $NaHCO_3$ buffer solution at pH 8.3 was added to a well plate (Maxisorp, Nunc Co.) in an amount of 50 μL/well and allowed to stand at 4° C. for 24 hours. Thereafter, the plate was washed with deionized water and blocked with PBS⁻ containing 0.5% BSA (by standing at room temperature for 60 minutes).

Then, the solutions in the wells were removed, 50 μL/well of culture supernatant of the transfected COS-1 was added to the wells and the plate was incubated at 25° C. for 60 minutes. After washing the plate 3 times with PBS⁻ containing 0.1% Tween 20, 1.0 μg/mL of HRP-conjugated 3C10 antibody was added to the wells in an amount of 50 μL/well and the plate was incubated at 25° C. for 60 minutes. After washing the plate 5 times with PBS⁻ containing 0.1% Tween 20, a color developing substrate (TMB) was added to the wells in an amount of 100 μL/well and reacted at room temperature for 30 minutes, followed by addition of a stop solution (1N hydrochloric acid) in an amount of 100 μL/well to terminate the reaction.

The absorbance at a wavelength of 450 nm was measured and the production amount of CD14 mutant polypeptide in a sample was calculated.

[4] [Preparation of sCD14(1-307) Deletion Mutant with Deletion of Amino Acids]

Similarly, plasmids that cause mammal cells to express various types of human soluble type CD14 deletion mutants with deletion of part of amino acids from the amino acid sequence of sCD14(1-307), namely deletion mutants Δ7-11, Δ57-64, Δ180-234, Δ235-282 and Δ180-282 (hereinafter, deleted portion is additionally indicated by Δ), were constructed as described in above [1] and [2]. In this case, the following primers were used. As to Δ7-11, the primer set of sense primer 4 (SEQ ID NO:27) and anti-sense primer 12 (SEQ ID NO:28), and the primer set of sense primer 5 (SEQ ID NO:29) and anti-sense primer 12 (SEQ ID NO:30) were used. As to Δ57-64, the primer set of sense primer 4 and anti-sense primer 14 (SEQ ID NO:31), and the primer set of sense primer 6 (SEQ ID NO:32) and anti-sense primer 13 were used. As to Δ180-234, the primer set of sense primer 4 and anti-sense primer 15 (SEQ ID NO:33), and the primer set of sense primer 7 (SEQ ID NO:34) and antisense primer 13 were used. As to Δ235-282, the primer set of sense primer 4 and anti-sense primer 16 (SEQ ID NO:35), and the primer set of sense primer 8 (SEQ ID NO:36) and anti-sense primer 13 were used. As to Δ180-282, the primer set of sense primer 4 and anti-sense primer 17 (SEQ ID NO:37), and the primer set of sense primer 9 (SEQ ID NO:38) and anti-sense primer 13 were used. The thus obtained plasmids were transfected into COS-1 cells according to the method as described [3] and human soluble CD14 deletion mutants were obtained.

The expression amount of CD14 deletion mutants was measured by EIA using an anti-human CD14 antibody. That is, anti-CD14 antibody MEM-18 (MONOSAN Co.) diluted 200 folds with 10 mM $NaHCO_3$ buffer solution at pH 8.3 was added to a 96-well plate (Maxisorp, Nunc Co.) in an amount of 50 μL/well and left to stand at 4° C. all day long. Thereafter, the plate was washed with pure water and blocked with PBS⁻ containing 0.5% BSA (by standing at room temperature for 60 minutes).

Then, the solution in the wells was removed, 50 μL/well of the supernatant of culture of the transfected COS-1 was added to the wells and the plate was incubated at 25° C. for 60 minutes. Thereafter, the plate was washed 3 times with PBS⁻ containing 0.1% of Tween 20, 1.0 μg/mL of HRP-conjugated 3C10 antibody was added to the wells in an amount of 50 μL/well and the plate was incubated at 25° C. for 60 minutes. After washing the plate 5 times with PBS⁻ containing 0.1% of Tween 20, a color developing substrate (TMB) was added to the wells in an amount of 50 μL/well and reacted at room temperature for 30 minutes, followed by addition of a stop solution (1N sulfuric acid) in an amount of 50 μL/well to terminate the reaction.

The absorbance at a wavelength of 450 nm was measured and the production amount of CD14 deletion mutant polypeptide in the sample was calculated.

Then, to confirm if the human soluble type CD14 deletion mutant with C-terminal deletion has the expected length, the molecular weight of the CD14 deletion mutant was determined by Western blotting with anti-human CD14 antibodies (3C10 and MEM-18). That is, 30 ng/lane each of CD14 deletion mutants was electrophoresed on SDS-polyacrylamide gradient gel (5-20%, ATTO Co.), the protein was transferred onto PVDF membrane (Japan Millipore Co.) and blocking reaction was performed with 30 mL of PBS containing 0.5% skimmed milk at room temperature for 1 hour, and 10 μg/mL of 3C10 and 100-fold diluted MEM-18 were added, followed by reaction at room temperature for 1 hour. Thereafter, reaction was performed with HRP-conjugated anti-mouse Ig antibody at room temperature for 30 minutes, and detection was performed with an ECL kit (Amersham Pharmacia Biotech Co.). As a result, bands were detected at sizes estimated by calculation for respective CD14 deletion mutant polypeptides.

[5] [Preparation of Human CD14 Amino Acid Substitution Mutants]

In this description, human sCD14(1-307) amino acid substitution mutant polypeptide obtained by substituting the amino acid at the 283rd position from the N-terminal of sCD14(1-307), Leu, by Ala is described as "sCD14(1-307) L283A" and other human sCD14(1-307) amino acid substitution tailored mutant polypeptides are described in a similar manner.

In order to prepare human sCD14(1-307) amino acid substitution modified polypeptides having introduced therein 1 or 2 amino acid mutations at various sites of human CD14(1-307), plasmids that express the polypeptides in mammalian cells were prepared by the following method.

Plasmid pM1673 that expresses sCD14(1-307)K279A was prepared as follows. That is, by using sense primer 4 and antisense primer 18 (SEQ ID NO:39) or by using sense primer 10 (SEQ ID NO:40) and antisense primer 13, and also using the plasmid pM1658 prepared in the above [2] as a template, PCR reaction was performed by repeating 30 times the cycle consisting of 98° C. for 10 seconds, 55° C. for 30 seconds, and 72° C. for 1 minute with Pyrobest DNA Polymerase (TaKaRa Co.).

As for the antisense primer 18 and sense primer 10, the sequence GCT (AGC in the case of antisense primer) encoding Ala was used in place of the sequence encoding Lys. DNA fragments amplified by the PCR were separated and recovered by 1% agarose gel electrophoresis and the terminals of the DNA fragments were blunt-ended with Klenow Fragment (TaKaRa Co.).

Then, by using a mixture of these fragments as a template and also using sense primer 5 and antisense primer 6, PCR reaction was performed again under the same conditions as described above. The DNA fragments amplified by the second PCR were subjected to double digestion with XhoI and HindIII and the product was ligated to an about 5.8 kb DNA fragment obtained by digestion of pM1656 with XhoI and HindIII. After the transformation of JM109 cells, the resulting colonies were confirmed by PCR to obtain the target CD14 mutant polypeptide-expressing plasmid (pM1673).

Similarly, plasmids (pM1663, pM1677, pM1664, pM1678, pM1665, pM1666, pM1667, pM1669, pM1670, pM1671 or pM1672) expressing sCD14(1-307)V282A, sCD14(1-307)L283A, sCD14(1307)D284A, sCD14(1-307) L285A, sCD14(1-307)S286A, sCD14(1307)C287A, sCD14 (1-307)R289A, sCD14(1-307)P294A, sCD14(1307)P296A, sCD14(1-307)P294/296A or sCD14(1-307)P300A obtained by substituting Val at position 282, Leu at position 283, Asp at position 284, Leu at position 285, Ser at position 286, Cys at position 287, Arg at position 289, Pro at position 294, Pro at position 296, Pro's at positions 294 and 296, or Pro at position 300 from the N-terminal each by Ala were prepared in the same manner as pM1673 by using antisense primers 19, 20, 21, 22, 23, 24, 25, 26, 27, 28 and 29 (SEQ ID NOs: 41, 42, 43, 44, 45, 46, 47, 48, 49, 50 and 51) and sense primers 11, 12, 13, 14, 15, 16, 17, 18, 19, 20 and 21 (SEQ ID NOs: 52, 53, 54, 55, 56, 57, 58, 59, 60, 61 and 62) with changing the codon sequence of the amino acid to which substitution was to be introduced to the codon sequence GCT or GCG encoding Ala (the sequence AGC or CGC in the case of antisense primers).

In addition, plasmid that expresses sCD14(1-307)R289D (pM1668) was similarly constructed. In this case, in order to substitute Arg by Asp, sense primer 22 (SEQ ID NO:63) and antisense primer 30 (SEQ ID NO:64) with the codon sequence (AGA) encoding Arg being changed to the codon sequence GAT (ATC in the case of antisense primer) encoding Asp were used.

Furthermore, plasmids that express mutants with Ser at position 286 thereof being substituted by Cys, Gly, Thr or Leu, respectively, were prepared. The same construction method as that for constructing sCD14(1-307)S286A expressing plasmid was used except that sense primer 23 (SEQ ID NO:65) and antisense primer 31 (SEQ ID NO:66) were used in the case of Cys substitution. Construction of other plasmids was performed by using sense primer 24 (SEQ ID NO:67) and antisense primer 32 (SEQ ID NO:68) in the case of Gly substitution, sense primer 25 (SEQ ID NO:69) and antisense primer 33 (SEQ ID NO:70) in the case of Thr substitution, and sense primer 26 (SEQ ID NO:71) and antisense primer 35 (SEQ ID NO:72) in the case of Leu substitution. The thus obtained plasmids were transfected into COS-1 cells according to the method as described [3] and human soluble CD14 amino acid substitution mutants were obtained.

The supernatant containing the obtained CD14 mutants was purified as necessary. That is, the supernatant was applied to an affinity column for purification (HiTrap column, (Amersham Pharmacia Biotech Co.)), to which anti-human CD14 antibody (3C10) was bound, for selective adsorption and then the column was eluted with pH gradient. The obtained eluted fractions were immediately neutralized with 1 M HEPES buffer at pH 8.0 to make their pH neutral. Each fraction was assayed by an EIA method using HRP-conjugated 3C10 and fractions containing CD14 mutant polypeptides were selected.

(4) [Experiments on Inhibition by Peptides]

1 μg/mL of purified sCD14(1-356) was diluted with carbonate buffer (pH 9.5) and immobilized to a plate (Maxisorp, Nunc) at 37° C. for 1 hour. Then, the plate was washed and blocked with 0.5% of BSA/PBS. The blocking solution was removed and each peptide prepared in (1) above diluted with PBS to 10 μg/mL was added to the plate. Subsequently, F1024-1-3 antibody labeled with peroxidase by the method of Nakane et al. (J. Histochem. Cytochem., 22:1084, 1974) was added in an amount of 1 μg/mL and reaction was performed at 37° C. for 1 hour.

The plate was washed 5 times with 0.9% of NaCl/0.5% of Tween 20 and color was developed with an $H_2O_2$/TMB solution. Thereafter, the reaction was stopped with a 0.5 M sulfuric acid, and the amount of bound F1024-1-3 antibody was measured.

As a result, as shown in FIG. 12, peptides A and B inhibited F1024-1-3 antibody though weakly, while peptides C and D and irrelevant peptide E used as a control did not inhibit the antibody. This suggests that the region F1024-1-3 antibody recognizes exists within the range from amino acid 283 to amino acid 318.

(5) [Experiments on Binding Antibody to CD14 Deletion Mutants]

3C10 antibody or 100-fold diluted MEM-18 antibody was immobilized to a plate (Maxisorp, Nunc) in an amount of 10 μg/mL and blocked with 0.5% of BSA/PBS. Then, the blocking solution was removed, each CD14 deletion mutant whose concentration had been measured was added to the plate, and the reaction was performed at room temperature for 1 hour. After washing, the peroxidase-labeled F1024-13 antibody or peroxidase-labeled 3C10 antibody was diluted with 10% of RS/0.1% of Tween-20/PBS in a concentration of 1 μg/mL and added to plate to react in the same manner as above at room temperature for 1 hour and half. After washing, color was developed with an $H_2O_2$/TMB solution, then the reaction was stopped with 0.5 M sulfuric acid, and the absorbance of the reaction mixture at a wavelength of 450 nm was measured by using NJ-2100 (Japan Intermed) plate absorbance meter.

Since it has been made clear that 3C10 and MEM-18 antibodies used for immobilization have respective binding sites at amino acids at positions 7 to 11 and amino acids at positions 57 to 64, out of the CD14 deletion mutants used here, CD14(Δ7-11) does not bind to 3C10 while CD14(Δ57-64) does not bind to MEM-18 but binds to other CD14 deletion mutants. Therefore, by analyzing results of 3 types of sandwich ELISA systems, 3C10/F1024-1-3 system, MEM-18/F1024-1-3 system, MEM-18/3C10 system, the binding activity of each antibody can be analyzed.

Analysis of the obtained results indicates that as shown in FIG. 13, F1024-1-3 antibody exhibits binding activity within a range of sCD14(1-356) to sCD14(1-307) and also binds to CD14(Δ7-11) with deletion of the binding site for 3C10 and CD14(Δ57-64) with deletion of the binding site for MEM-18 and further exhibits binding activity to CD14 (Δ180-282) with deletion of amino acids at positions 180 to 282 of sCD14(1-307). From this, it follows F1024-1-3 antibody is different from 3C10, MEM-18 antibodies and has a binding region closer to the C-terminal side of CD14 than amino acid 285 is. Note that the binding activity to sCD14(1-307) was indicated by (+) since it was weaker than the binding activities to other CD14 deletion mutants.

(6) [Experiments on Binding by CD14 Amino Acid Substitution Mutants]

The binding activity of CD14 amino acid substitution mutants was measured by using measurement systems similar to those described above. As a result, as shown in FIG. 14, the binding activity of F1024-1-3 antibody was lost by substituting amino acid 294, Pro, by Ala while such a phenomenon was not observed in the case of 3C10 and MEM-18 antibodies. F1024-1-3 antibody's loss of binding activity by point mutation at amino acid 294 of CD14, Proline is attributable to the change in three-dimensional structure of CD14. Therefore, it is evident that F1024-1-3 antibody recognizes a three-dimensional structure that can be generated when the amino acid 294 is Pro.

(7) [Experiments on Binding by Peptide Mapping]

For the purpose of more specifically analyzing epitopes that F1024-1-3 antibody recognizes, 46 kinds of 10-amino acid residue peptides having an amino acid sequence shifted by 2 amino acids toward the C-terminal based on the amino acid sequence between amino acids at positions 246 to 345 of CD14 described in SEQ ID NO:1 by using custom SPOTs (GENOSYS) were synthesized on a membrane. Then, based on the protocol, the membrane was blocked and reacted with F1024-1-3 antibody as a primary antibody, and after washing, reacted with β-galactosidase-labeled anti-rat IgG F(ab')$_2$ antibody (American Qualex Antibodies) as a secondary antibody. After washing, a color developing solution was added and emergence of blue spots was observed. As a result, no spot attributable to F1024-1-3 was detected and determination of epitope of the antibody by peptide mapping was unsuccessful. This suggests that F1024-1-3 antibody does not recognize linear peptide epitopes composed of 10 amino acids but recognizes epitopes caused by three-dimensional structure.

From these, it has been made clear that the binding region of F1024-1-3 antibody recognize binding region existing between amino acids at positions 285 to 315 of CD14 described in SEQ ID NO:1 and recognizes the three-dimensional structure that can be generated by the amino acid 294 when it is Pro. That is, it has been made clear that the antibody recognizes the epitope existing between amino acids at positions 285 to 315 of the three-dimensional structure that can be generated by the amino acid 294 of CD14 when it is Pro.

Example 12

Analysis of the Region of Epitope for Anti-CD14 Antibody.

The region of recognition site on CD14 of an anti-CD14 antibody that is needed in order that the anti-CD14 antibody has the same function as F1024-1-3 antibody was analyzed attending to the periphery of the epitope of F1024-1-3 antibody as analyzed in Example 11.

Profile search for human CD14 was performed on BLOCKS database, which is a database prepared by arranging data in a multiple alignment so that motives are aligned, calculating similarity scores again including these of residues therearound, and extracting only those regions having no insertion or deletion and having a high degree of conservation. Further, analysis was made by various types of secondary structure prediction methods (Lev, GOR IV, PREDATOR).

As a result, based on the profile search of BLOCKS database, a region having similarity to the binding region of IL-1 (Accession No. BL005253C) to its receptor was identified as 39 amino acid residues at the positions 269 to 307.

The amino acid residues (their residue numbers in brackets) presumed to have high degree of conservation include Q(271), V(272), P(273), L(276), K(279), L(283), L(285), S(286), C(287), P(294), E(298), L(299), P(300), E(301), N(304), L(305) and T(306).

Furthermore, the sequence from the position 287 toward the C-terminal of this region did not have so high homology to LRR (PDB-ID:1A4Y:A).

Various types of secondary structure prediction methods (Lev, GORIV, PREDATOR) indicated that no coincident prediction results as to both α-helix structure and β-sheet structure can be obtained, that it is generally difficult to assume a helix structure or a sheet structure when proline exists in large amounts, and that amino acid 304, asparagine, coincides with the sugar chain binding motif in the motif database and is a sugar chain bindable site. From this it has revealed that this region is exposed on the surface of the protein.

As seen from these analyses, the region is capable of forming a loop under physiological conditions and is a site capable of interaction with other proteins.

That is, it was found from the epitope for F1024-1-3 antibody of Example 11 and the above-mentioned analyses that the range of epitope for anti-CD14 antibody that can inhibit the binding between human CD14 and TLR is equal to the region from the position 269 to the position 315 of human CD14.

Example 13

Sequence Determination of Rat F1024-1-3 Antibody Variable Region

Gene sequences of variable regions of heavy chain and light chain of rat F1024-1-3 antibody was analyzed by the following method and an amino sequence of a complementarity-determining regions (CDR) was determined.

(1) Analysis of Amino Acid Sequence of Purified F1024-1-3 Antibody

At first, the F1024-1-3 antibody purified by the method described in Example 2 was pyridylethylated (hereinafter abbreviated as PE) and was then purified by RP-HPLC. The PE-light chain was directly subjected to an amino acid sequence analysis with Procise 494cLC (Applied Biosystems Inc.). A peptide sequence of the amino terminal of the heavy chain could not be determined because the amino terminal had been blocked. Therefore, after decomposing the PE-heavy chain with CNBr, the fragments of polypeptide were separated and purified with RP-HPLC and were then subjected to an amino acid sequence analysis with a peptide sequencer Procise494cLC (Applied Biosystems Inc.). Likewise, the PE-light chain was also subjected to the amino acid sequence analysis of peptide fragments. The obtained sequences were compared with the sequences of heavy and light chains of a rat IgG sequence described in EMBL database to determine the positions of polypeptide fragments on the sequence. The sequence of the amino terminal of the heavy chain could not be determined, so that the sequence of the amino terminal was determined by estimation on the basis of reports such as Cohen, H (C. R. Acad. Sci, Vie 317(4), 293-298, 1994), William J. (Protein Engineering 9(7), 623-628, 1996), and Lutz Riechmann (Nature 332, 323-327, 1988)

(2) cDNA Synthesis, PCR, and Sequencing of F1024-1-3 Antibody

Primers of SEQ ID NO: 73 to 82 were synthesized according to the amino acid sequence data determined in (1). Also, as a light-chain primer, primers of SEQ ID NO: 83 and 84 derived from 5'UTR and 3'UTR regions were synthesized. The base sequences of the primers and the corresponding positions of the amino acid sequences in FIG. 15 (described later) are listed in Table 3.

TABLE 3

| SEQ ID NO. | Amino acid position corresponding to FIG. 15 | | Sequence (5'-3') |
|---|---|---|---|
| 73 | Light chain sense | (1-8) | GAYATHGTNATGACNCARWSNCC |
| 74 | Light chain sense | (9-14) | ACNWSNATHWSNATHWS |
| 75 | Light chain antisense | (179-174) | NARNSWNARNGTNSWNS |
| 76 | Light chain antisense | (188-181) | RTTRTGNCKYTCRTAYTCRTCYTT |
| 77 | Heavy chain sense | (34-41) | ATGAAYTGGGTNIIICARGCNCC |
| 78 | Heavy chain sense | (34-41) | ATGAAYTGGGTNIIICARCCNGC |
| 79 | Heavy chain antisense | (147-139) | YTTNACNARRCANCCNARNGTNAGG |
| 80 | Heavy chain antisense | (149-141) | RTANCCYTTNACNARRCANCCNARNG |
| 81 | Heavy chain sense | (2-9) | GTNAARYTNYTNGARWSNGGNGG |
| 82 | Heavy chain sense | (7-14) | WSNGGNGGNGGNYTNGTNCARCC |
| 83 | 5'UTR sense | | GCAAGCTTGATCCAGACAGGACACAGGCCAGAACAT |
| 84 | 3'UTR antisense | | CACGAATTCTGCAGTGGTGCAGCATCAGC |

Mixed bases followed the international notation.
(Y;A,C,G,H;A,C,T,N;A,C,G,TR;A,G,W;A,T,S;C,G,K;G,T,I;Inosine)

At first, one frozen ample of F1024-1-3 antibody-producing hybridoma F1024-1-3 was defrosted and was then cultured in a PRMI1640 medium containing 10% FCS. Subsequently, cultured cells were collected and was then washed in PBS⁻ (pH 7.4), followed by subjecting to cDNA analysis as described below in accordance with Y. Kagawa et al., Mutagenesis, 14(2), 199-205 (1999). First of all, total RNA was extracted with ISOGENE (Nippon Gene). Then, cDNA was synthesized using an oligo dT primer according to the manual of Superscript Pre-amplification System for First Strand cDNA Synthesis (Invitrogen). The obtained cDNA was used as a template, and PCR was performed using a sense primer and an antisense primer. The PCR was performed under the conditions of 35 times the cycle of 94° C. for 60 seconds, 55° C. for 30 seconds, and 72° C. for 120 seconds using ExTaq polymerase (Takara), and GeneAmp PCR system 2400 (Perkin Elmer) was used. After confirming bands on a gel, the PCR product was cut out and purified, followed by sequencing with ABI373A DNA sequencer (Applied Biosystems Inc.) according to the manual of ABI Dye Deoxy Cycle Sequencing Kit (Applied Biosystems Inc.). The obtained amino acid sequences of the heavy chain and the light chain were shown in FIG. 15, and the amino acid sequences of CDRs were shown in FIG. 16 (SEQ ID NO: 3 to 8). In addition, the obtained base sequences of the heavy chain and the light chain were shown in FIG. 17, and those of the CDRs were shown in FIG. 18.

Example 14

Preparation of F1024-1-3 Rat-Human Chimeric Antibody

A V region having an antigen binding activity is derived from an F1024-1-3 antibody, i.e., derived from a rat antibody. Therefore, an antibody having little antigenicity to human can be obtained by preparing an antibody (chimeric antibody) with a C region being derived from human. Many chimeric antibodies have been developed since the report of Morrison et al. in 1984 (Proc. Natl. Acad. Sci. USA. 81: 6851, 1984).

(1) Cloning of Antibody Gene

F1024-1-3 antibody producing cell strain F1024-1-3 is cultured, and cells are prepared. After washing the obtained cells with PBS⁻ (Sigma), total RNA is isolated and purified using Isogene (Nippon Gene). Then, cDNA is synthesized using oligo-dT primer and SuperScript II System (Invitrogen). Sense primers are synthesized on the basis of the amino acid sequences of amino terminals of the heavy chain and the light chain. In addition, a heavy chain antisense primer is prepared on the basis of the sequence of framework 4, while a light chain antisense primer is prepared on the basis of Vκ sequence. After PCR, a DNA fragment is incorporated in a TA cloning vector (Invitrogen), followed by analyzing the sequence thereof.

(2) Construction of Vector that Expresses Rat-Human Heavy Chain and Light Chain

At first, a base sequence encoding the N terminal side of CH1 region in human immunoglobulin G1 is synthesized as a sense primer, and an antisense primer synthesizes a region containing a sequence of a 3'-nontranslating region of human immunoglobulin G1. Using the sense primer and the antisense primer, the CH region of human immunoglobulin is amplified by a PCR reaction with HumanSpleen 5'-Stretch cDNA Library (manufactured by Clontech Co., Ltd.). In addition, the heavy-chain sense primer is prepared such that it contains a base sequence encoding the heavy chain region of Example I-1 and a sequence encoding a EcoRI site into an amino acid sequence that encodes the N terminal side of the CH1 region in human immunoglobulin G1. The antisense primer is prepared such that it contains a base sequence encoding an amino acid sequence positioned at the C terminal side of a CH3 region in human immunoglobulin G1 and a BamHI site. These primers of chimera are combined to incorporate the human immunoglobulin CH region such that the orientation thereof is coincident with the rat VH region. The obtained PCR product is digested with a restriction enzyme. The DNA fragment is incorporated into an expression vector pcDNA 3.1 (Invitrogen) to prepare a rat-human heavy chain expression plasmid. Likewise, an expression plasmid that contains a chimeric antibody gene having the human CL region and the light chain region derived from rat is constructed.

(3) Preparation of chimeric antibody For preparing a transformant, each expression plasmid is linearized by cutting with a restriction enzyme. Then, the gene is introduced into SP2/O-ag14 (ATCC CRL1581) using a gene pulsar (BIO-RAD) or the like. Cells that produce the desired antibodies are selected on the basis of the presence or absence of rat-human chimeric antibodies produced in the supernatant after incubation. Specifically, about 20 µg of linearized DNA fragment is electroporated in $1 \times 10^7$ cells at 360 V with a capacitance of 25 µFD. Next, cells are inoculated in a 96-well plate. After culturing them for 2 days, D-MEM (sigma) that contains 10% FCS, 1×HT (Invitrogen), and 0.2 mg/ml G-418 is added and is then incubated for more 2 weeks for selecting cells in which plasmid fragments are incorporated. When the cells become confluent, the cells are cultured in a serum free medium (Hybridoma-SFM, Invitrotec) and the supernatant of the culture is purified with a protein A column (Prosep-A, Millipore) to obtain a purified chimeric antibody.

The CD14/TLR binding inhibitory activity of the resulting chimeric antibody is confirmed by the method of Example 2.

Example 15

Preparation (1) of Humanized F1024-1-3 Antibody (1) For retaining a high affinity of computer-modeling humanized antibody of the humanized F1024-1-3 antibody variable region, selection of framework residues is performed in conformance with a generic method of Queen et al. (Proc. Natl. Acad. Sci. USA 86: 10029, 1989). For a human sequence, a sequence having a high framework homology to a rat F1024-1-3 antibody is selected on the basis of kappa light chain and heavy chain database of Kabat et al. (Sequences of Proteins of Immunological Interest, 5$^{th}$ ed., U.S. Department of Health and Human Services, 1991). Furthermore, the modification of an amino acid in a most suitable framework is performed by computer analysis. Specifically, a molecular model of F1024-1-3 antibody variable region is constructed using the computer program ENCAD (Levitt, J. Mol. Boil. 168, 595 (1983)). The CDR sequence of F1024-1-3 antibody is inserted in FR in a human Eu antibody molecular model obtained by the antibody database (Stephens et al., Immunology 85 (4), 668-674 (1995)). In a FR region that shows a significant contact of CDR and FR, which is different from the original human antibody model on the computer model, a substitution with an amino acid derived from a rat antibody is performed on a position to be expected that the contact between CDR and FR is improved through the amino acid substitution. In addition, in the database of human antibodies, an amino acid residue in FR, which rarely appears at that position, is substituted with a human consensus amino acid in that position. As the quality of the amino acid substitution is confirmed by actual activity, several kinds of antibodies having different types of amino acid substitutes are prepared.

(2) Construction of Humanized F1024-1-3 Antibody

Based on the sequence selected in (1), a gene that encodes an amino acid sequence containing a signal peptide, a splicing signal, and a restriction site (e.g., XbaI) is constructed. The constructed gene is prepared such that several kinds of synthetic nucleotides (almost 80 base length) are overlapped. That is, a double-stranded fragment is obtained by performing annealing to a pair of oligonucleotide and elongating with the Klenow fragment of DNA polymerase. After denaturing the fragment to obtain a single strand, annealing is performed in a similar manner and elongation is performed using the Klenow fragment of DNA polymerase to obtain a double-stranded fragment that encodes the whole length of the gene. The obtained fragment is amplified by PCR with Taq polymerase, and after purification, it is cut by a restriction enzyme (e.g., XbaI) and is then purified. The purified fragment is inserted into a XbaI site of a plasmid pVg1 (Co et al., J. Immunol. 148: 1149 (1992)) having a XbaI-BamHI fragment and a constant region gene containing from a CH1 exon to CH3 exon of a human $\gamma_1$ gene. Using a similar operation, it is also possible to insert it into a plasmid having a constant region gene of $\gamma_4$. In addition, when the number of amino acids to be substituted is small, it is possible to introduce it into an expression plasmid by preparing with induction of site-directed mutagenesis. A light chain variable region sequence may be constructed by the same way as described above. In this case, one containing a human C κ region is used as a pVk vector.

For preparing a transformant that produces antibodies, the heavy chain and light chain plasmids are linearized by being cut with an restriction enzyme (BamHI and FspI in the case of a pVk plasmid), followed by introducing this into mouse myeloma cells Sp2/0-Ag14 (ATCC CRL1581) using a gene pulsar (BIORAD). Specifically, about 20 µg of a linearized DNA fragment is electroporated in $1 \times 10^7$ cells at 360 V with a capacitance of 25 µFD. Next, cells are inoculated in a 96-well plate. After incubating them for 2 days, D-MEM (sigma) that contains 10% FCS, 1×HT (Invitrogen), and 0.25 mg/ml xanthine, and 1 µg/ml mycophenolic acid is added and is then cultured for more 2 weeks to select cells in which plasmid fragments have been incorporated. An objective humanized F1024-1-3 antibody-producing strain is selected from antibodies that appear in the supernatant after the culture. That is, antibodies in the supernatant bound to solid-phase CD14 antigens. The binding antibodies are detected by a peroxidase-labeled anti-human IgG1 or IgG4 antibody. The selected strain is cultured in a medium containing 10% FCS until it becomes confluent, and then the medium is exchanged with a serum-free medium (Hybridoma SFM, Invitrogen). The supernatant of the culture is collected and is bound to a protein A (Prosep-A, Millipore), followed by eluting with 0.1 M glycine hydrochloride (pH 3.0). The purified antibody is dialyzed with PBS⁻ (Sigma), and the concentration of antibody is calculated by absorbance at 280 nm (1 mg/ml of human antibody shows an absorbance of 1.3).

(3) Evaluation of Humanized Antibody

For confirming whether the humanized antibody has the same activity as that of the rat antibody, comparisons are made with respect to the CD14/TLR binding inhibitory activity and the affinity of binding. The CD14/TLR binding inhibitory activity is performed in accordance with the description of Example 2 and is compared with that of the F1024-1-3 antibody. The affinity measurement is performed using the BIACORE System (BIACORE Co., Ltd.). That is, the purified CD14 is fixed on a CM5 tip (BIACORE Co., Ltd.) using the BIACORE 3000 in accordance with a manual. Next, the diluent series of the antibody is prepared by being diluted with a HBS-EP buffer (BIACORE Co., Ltd.), and each sample is injected and analyzed. The antigen-antibody combination is dissociated by a 100-mM hydrochloric acid solution, followed by injecting a subsequent sample. The obtained data is analyzed using a program of BIACORE (BIA Evaluation, BIACORE) and the affinity (Kd) is calculated.

Example 16

Preparation (2) of Humanized F1024-1-3 Antibody (1) Preparation of Humanized Antibody Gene For allowing the inserted CDR sequence to retain a suitable domain structure having an activity in the humanized antibody, an original FR region sequence is also inserted. An amino acid involved in retaining the CDR domain structure is analyzed from the properties of the amino acid in FR (hydrophobicity, hydrophilicity, acidity, basicity, molecular size, and so on), and from modeling using a computer. That is, such a modeling is performed using a software QUANTA/CHARMm or Modeler (Molecular Simulations) actuated on a silicon graphic. The three-dimensional structure of an antibody having a high homology to the VH and VL regions of the F1024-1-3 antibody is retrieved from human antibody sequences registered in Brookhaven Protein Data Bank (PDB), and depending thereon the three-dimensional structure of the F1024-1-3 antibody is then estimated. An amino acid group (first group) in the FR region which is hydrogen-bonded to CDRs of heavy chain and light chain on the estimated three-dimensional structure is selected and furthermore an amino acid group (second group) in the FR region which is hydrogen-bonded thereto is selected. Likewise, an amino acid group (first group) in the FR region which is estimated to be bonded to CDR with an energy bond such as electrostatic interaction or Van der Waals force and further, an amino acid group (second group) in the FR region which is estimated to be bonded thereto are selected. The amino groups in the FR region selected as described above are inserted in the human antibody sequence together with the CDR amino acid. However, such an amino acid is not inserted when a sequence is produced, which is not found in the amino acids of a variable region of the human antibody sequence obtained from the classification of Kabat et al. (Sequences of proteins of Immunological Interest, $5^{th}$ ed., U.S. Department of Health and Human Services, 1991), NCBI (National Center for Biotechnology Information), and so on. Depending on the information obtained as described above, the sequences to be inserted to human antibody sequences VH and VL are determined to construct a gene to be used for preparing a humanized antibody.

The constructed gene is prepared by a method in which an Amersham's kit (Oligonucleotide-directed in vitro mutagenesis system version 2) and a PCR method are combined together, a method in which several kinds of long-chain synthetic nucleotides are combined and amplified, and a method in which VH or VL gene of chimeric antibody is amplified using several kinds of primers as templates and the total length gene fragment is obtained using these amplified gene fragments as templates. The resulting amplified gene fragment is introduced into a restriction enzyme site of a plasmid pVg1 or a plasmid pVk containing Vk described in Example 15 to prepare an expression plasmid. The prepared plasmid is introduced into a cell by the method described in Example 15 to obtain a transformant, and similarly a purified antibody is prepared. In addition, the estimation of the antibody is performed similarly.

Example 17

Preparation of CDR Peptide

Each peptide is synthesized using a peptide synthesizer (433A, Applied Biosystems) on the basis of the CDR sequence defined in Example 13. After being cut out by a suitable method, the synthesized peptide is purified by HPLC to obtain a freeze-dried product. The CD14/TLR binding inhibitory activity of the obtained peptide is confirmed by the method of Example 2.

Example 18

Establishment of Cell Strain that Highly Expresses Modified CD14 Polypeptide (1) [Construction of Plasmid that Expresses Modified CD14 Polypeptide]

A plasmid for expressing sCD14(1-307)S286C obtained in Example 11 was double-digested with XbaI and HindIII to cut out a DNA fragment encoding sCD14 (1-307) S286C. Meanwhile, an ampicillin resistance gene, a human EF promoter, and an expression vector (pM1103) encoding a folate dehydrogenase gene (PHFR) on the upper stream of SV40 late polyA and SV40 early polyA were double-digested with XbaI and NotI on the lower stream of EF promoter and the upper stream of late poly A. A previously obtained DNA fragment that encodes sCD14(1-307)S286C was inserted in the XhoI/NotI site of the pM1103, and competent cell JM109 (TaKaRa Co., Ltd.) was used to carry out transformation in accordance with a suitable method to obtain a plasmid (pM1675) by which human sCD14(1-307) S286C was expressed in a mammal cell.

(2) Establishment of CHO Transformant for Producing Modified CD14 Polypeptide

For establishing the CHO transformant for producing modified CD14 polypeptide, the expression plasmid pM1675 prepared in (1) was transfected to the DHFR-defected Chinese hamster uterine tumor line CHO DxB11 by the method described below. That is, 50 μL of FuGENE 6 (Roche Diagnostics, Co., Ltd.) and 12.5 μg of pM1675 were mixed together in accordance with the attached protocol, followed by the addition of CHO DxB11 cells semi-confluently grown in a 150 cm² Roux flask. On the following day, the cells were collected with a trypsin/EDTA treatment and were then inoculated in a 10 cm² dish with a MEM α-medium free from nucleic acid containing 10% inactivated dialyzing FBS and 2 mM L-glutamine at a density of $2 \times 10^4$ cells per dish. Subsequently, the medium was exchanged every 3 to 4 days with a MEM α-medium free from nucleic acid containing 10% inactivated dialyzing FBS and 2 mM L-glutamine. As a result of the selective culture for 18 days, 24 clones growing in the nucleic acid defective medium were obtained. Next, for 24 strains of the obtained clones, the amount of modified CD14 polypeptide produced in the supernatant of the culture was measured by the same method as that of Example 11. Consequently, 9 clones with a production amount of more than 2 µg/mL were obtained. Among them, the TfS286C-99 strain showed a highest production amount of 5.7 µg/mL.

(3) Establishment of Modified CD14 Polypeptide-High-Production Transformant

For establishing a modified CD14 polypeptide-high-production transformant, the selective culture was performed by the following method. Among the clones established in (2), the clone (TfS286C-99) having the highest production amount was inoculated at a density of 3000 cells in a 10 cm² dish with a MEM α-medium free from nucleic acid containing a 150 nM (final concentration) methotrexate (MTX), 10% inactivated dialyzing FBS, and 2 mM L-glutamine. After three days, the medium was exchanged with a MEM α-modification nucleic acid defective medium containing a 150 nM (final concentration) MTX, 10% inactivated dialyzing FBS, and 2 mM L-glutamine. Then, the selective culture was performed for 5 days. Consequently, 15 clones growing in the medium containing 150 nM of MTX were obtained. For the 15 strains of the obtained clones, the production amount of modified CD14 polypeptide was investigated. The concentration of modified CD14 polypeptide in the culture supernatant of each of the 15 kinds of clones was measured by the same method as that of Example 11. Consequently, clones TfS286C-99-150-3, TfS286C-99-150-8, and TfS286C-99-150-9 with their respective production amounts of 147 µg/mL, 144 µg/mL, and 154 µg/mL were obtained.

CD14/TLR biding inhibitory activity of sCD14(1-307)S286C obtained from each clone was confirmed by the method of Example 2.

INDUSTRIAL APPLICABILITY

According to the present invention, an anti-CD14 antibody, which is an antibody that inhibits a human CD14 mediated cell activation and which is capable of even controlling the signal transduction into cells even though CD14/LPS has already been formed, is provided. Also, a monoclonal antibody, a humanized antibody, and a chimeric antibody, each of which has a specific amino acid sequence as CDR, are provided. In addition, an antibody that inhibits the binding to TLR is provided.

Furthermore, a method for preparing an antibody with a specific region by specifying a recognizing region required for allowing the anti-human CD14 antibody to do these actions in the CD14, a medical composition for sepsis containing a substance that inhibits the binding between CD14 and TLR as an active ingredient.

What is claimed is:

1. A monoclonal antibody produced by the hybridoma F1024-1-3 deposited at the International Patent Organism Depository under Accession No. FERM BP-7511.

2. An isolated anti-CD14 monoclonal antibody comprising complementarity determining regions (CDRs) consisting of SEQ ID NOS:3-8.

3. An isolated anti-CD14 humanized antibody or chimeric antibody comprising complementarity determining regions (CDRs) consisting of SEQ ID NOS:3-8.

4. A pharmaceutical composition for treatment of sepsis comprising an antibody according to claim 1 as an active component.

5. A hybridoma, wherein said hybridoma is F1024-1-3 deposited at the International Patent Organism Depository under Accession No. FERM BP-7511.

6. A pharmaceutical composition for treatment of sepsis comprising the monoclonal antibody according to claim 2 as an active component.

7. An isolated anti-CD14 monoclonal antibody comprising a light chain variable region and a heavy chain variable region, wherein said light chain variable region comprises CDRs consisting of SEQ ID NOS:3-5, and wherein said heavy chain variable region comprises CDRs consisting of SEQ ID NOS:6-8.

8. An isolated anti-CD14 humanized antibody or chimeric antibody comprising a light chain variable region and a heavy chain variable region, wherein said light chain variable region comprises CDRs consisting of SEQ ID NOS:3-5, and wherein said heavy chain variable region comprises CDRs consisting of SEQ ID NOS:6-8.

9. An isolated anti-CD14 monoclonal antibody comprising CDRs consisting of SEQ ID NOS:3-8, wherein said antibody inhibits the binding of TLR2 or TLR4 to CD14.

10. An isolated anti-CD14 humanized antibody or chimeric antibody comprising CDRs consisting of SEQ ID NOS:3-8, wherein said antibody inhibits the binding of TLR2 or TLR4 to CD14.

11. An isolated anti-CD14 monoclonal antibody comprising each of the CDRs of antibody F1024-1-3 produced by the hybridoma F1024-1-3 deposited at the International Patent Organism Depository under Accession No. FERM BP-7511.

12. An isolated anti-CD14 humanized antibody or chimeric antibody comprising each of the CDRs of antibody F1024-1-3 produced by the hybridoma F1024-1-3 deposited at the International Patent Organism Depository under Accession No. FERM BP-7511.

13. The monoclonal antibody of claim 11, wherein said antibody inhibits binding of TLR2 or TLR4 to CD14.

14. The humanized antibody or chimeric antibody of claim 12, wherein said antibody inhibits binding of TLR2 or TLR4 to CD14.

15. A pharmaceutical composition for treatment of sepsis comprising the monoclonal antibody according to claim 11 as an active component.

* * * * *

SEQUENCE LISTING

```
<160> NUMBER OF SEQ ID NOS: 84

<210> SEQ ID NO 1
<211> LENGTH: 356
<212> TYPE: PRT
<213> ORGANISM: human

<400> SEQUENCE: 1

Thr Thr Pro Glu Pro Cys Glu Leu Asp Asp Glu Asp Phe Arg Cys Val
 1               5                  10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
        50                  55                  60

Asp Thr Val Lys Ala Leu Arg Val Arg Arg Leu Thr Val Gly Ala Ala
    65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
               100                 105                 110

Met Pro Pro Leu Pro Leu Glu Ala Thr Gly Leu Ala Leu Ser Ser Leu
           115                 120                 125

Arg Leu Arg Asn Val Ser Trp Ala Thr Gly Arg Ser Trp Leu Ala Glu
       130                 135                 140

Leu Gln Gln Trp Leu Lys Pro Gly Leu Lys Val Leu Ser Ile Ala Gln
   145                 150                 155                 160

Ala His Ser Pro Ala Phe Ser Cys Glu Gln Val Arg Ala Phe Pro Ala
               165                 170                 175

Leu Thr Ser Leu Asp Leu Ser Asp Asn Pro Gly Leu Gly Glu Arg Gly
```

-continued

```
               180                 185                 190
Leu Met Ala Ala Leu Cys Pro His Lys Phe Pro Ala Ile Gln Asn Leu
            195                 200                 205
Ala Leu Arg Asn Thr Gly Ile Glu Thr Pro Thr Gly Val Cys Ala Ala
    210                 215                 220
Leu Ala Ala Gly Val Gln Pro His Ser Leu Asp Leu Ser His Asn
225                 230                 235                 240
Ser Leu Arg Ala Thr Val Asn Pro Ser Ala Pro Arg Cys Met Trp Ser
                245                 250                 255
Ser Ala Leu Asn Ser Leu Asn Leu Ser Phe Ala Gly Leu Glu Gln Val
            260                 265                 270
Pro Lys Gly Leu Pro Ala Lys Leu Arg Val Leu Asp Leu Ser Cys Asn
        275                 280                 285
Arg Leu Asn Arg Ala Pro Gln Pro Asp Glu Leu Pro Glu Val Asp Asn
    290                 295                 300
Leu Thr Leu Asp Gly Asn Pro Phe Leu Val Pro Gly Thr Ala Leu Pro
305                 310                 315                 320
His Glu Gly Ser Met Asn Ser Gly Val Val Pro Ala Cys Ala Arg Ser
                325                 330                 335
Thr Leu Ser Val Gly Val Ser Gly Thr Leu Val Leu Leu Gln Gly Ala
            340                 345                 350
Arg Gly Phe Ala
        355
```

<210> SEQ ID NO 2
<211> LENGTH: 47
<212> TYPE: PRT
<213> ORGANISM: human

<400> SEQUENCE: 2

```
Leu Glu Gln Val Pro Lys Gly Leu Pro Ala Lys Leu Arg Val Leu Asp
1               5                   10                  15
Leu Ser Cys Asn Arg Leu Asn Arg Ala Pro Gln Pro Asp Glu Leu Pro
            20                  25                  30
Glu Val Asp Asn Leu Thr Leu Asp Gly Asn Pro Phe Leu Val Pro
        35                  40                  45
```

<210> SEQ ID NO 3
<211> LENGTH: 10
<212> TYPE: PRT
<213> ORGANISM: Artificial Sequence
<220> FEATURE:
<223> OTHER INFORMATION: LV-CDR1 sequence described in Fig. 16

<400> SEQUENCE: 3

```
Gln Asn Val Gly Ser Asn Val Asp Trp Tyr
1               5                   10
```

<210> SEQ ID NO 4
<211> LENGTH: 6
<212> TYPE: PRT
<213> ORGANISM: Artificial Sequence
<220> FEATURE:
<223> OTHER INFORMATION: LV-CDR2 sequence described in Fig. 16

<400> SEQUENCE: 4

```
Lys Ala Ser Asn Arg Tyr
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: LV-CDR3 sequence described in Fig. 16

<400> SEQUENCE: 5

Met Gln Ser Asn Thr Asn Pro Pro Trp
1               5

<210> SEQ ID NO 6
<211> LENGTH: 5
<212> TYPE: PRT
<213> ORGANISM: Artificial Sequence
<220> FEATURE:
<223> OTHER INFORMATION: HV-CDR1 sequence described in Fig. 16

<400> SEQUENCE: 6

Asp Tyr Ala Met Asn
1               5

<210> SEQ ID NO 7
<211> LENGTH: 15
<212> TYPE: PRT
<213> ORGANISM: Artificial Sequence
<220> FEATURE:
<223> OTHER INFORMATION: HV-CDR2 sequence described in Fig. 16

<400> SEQUENCE: 7

Trp Ile Asn Thr Gln Thr Gly Lys Pro Thr Tyr Ala Asp Asp Phe
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: HV-CDR3 sequence described in Fig. 16

<400> SEQUENCE: 8

Thr Tyr Phe Cys Thr Arg Ser Thr Phe Tyr Tyr Ser Ser Tyr Ile Tyr
1               5                   10                  15

Gly Trp

<210> SEQ ID NO 9
<211> LENGTH: 855
<212> TYPE: DNA
<213> ORGANISM: Artificial Sequence
<220> FEATURE:
<223> OTHER INFORMATION: Nucleotide sequence of the DNA encoding for
      the polypeptide of the present       invention
<220> FEATURE:
<221> NAME/KEY: CDS
<222> LOCATION: (1)..(855)

<400> SEQUENCE: 9 acc acg cca gaa cct tgt gag ctg gac gat gaa gat ttc cgc tgc gtc      48
Thr Thr Pro Glu Pro Cys Glu Leu Asp Asp Glu Asp Phe Arg Cys Val
1               5                   10                  15 tgc aac ttc tcc gaa cct cag ccc gac tgg tcc gaa gcc ttc cag tgt      96
Cys Asn Phe Ser Glu Pro Gln Pro Asp Trp Ser Glu Ala Phe Gln Cys
                20                  25                  30 gtg tct gca gta gag gtg gag atc cat gcc ggc ggt ctc aac cta gag     144
Val Ser Ala Val Glu Val Glu Ile His Ala Gly Gly Leu Asn Leu Glu
            35                  40                  45
```

| | | |
|---|---|---|
| ccg ttt cta aag cgc gtc gat gcg gac gcc gac ccg cgg cag tat gct<br>Pro Phe Leu Lys Arg Val Asp Ala Asp Ala Asp Pro Arg Gln Tyr Ala<br>50                         55                        60 | 192 |
| gac acg gtc aag gct ctc cgc gtg cgg cgg ctc aca gtg gga gcc gca<br>Asp Thr Val Lys Ala Leu Arg Val Arg Arg Leu Thr Val Gly Ala Ala<br>65                 70                      75                      80 | 240 |
| cag gtt cct gct cag cta ctg gta ggc gcc ctg cgt gtg cta gcg tac<br>Gln Val Pro Ala Gln Leu Leu Val Gly Ala Leu Arg Val Leu Ala Tyr<br>                   85                      90                      95 | 288 |
| tcc cgc ctc aag gaa ctg acg ctc gag gac cta aag ata acc ggc acc<br>Ser Arg Leu Lys Glu Leu Thr Leu Glu Asp Leu Lys Ile Thr Gly Thr<br>                100                    105                    110 | 336 |
| atg cct ccg ctg cct ctg gaa gcc aca gga ctt gca ctt tcc agc ttg<br>Met Pro Pro Leu Pro Leu Glu Ala Thr Gly Leu Ala Leu Ser Ser Leu<br>                115                    120                    125 | 384 |
| cgc cta cgc aac gtg tcg tgg gcg aca ggg cgt tct tgg ctc gcc gag<br>Arg Leu Arg Asn Val Ser Trp Ala Thr Gly Arg Ser Trp Leu Ala Glu<br>130                       135                    140 | 432 |
| ctg cag cag tgg ctc aag cca ggc ctc aag gta ctg agc att gcc caa<br>Leu Gln Gln Trp Leu Lys Pro Gly Leu Lys Val Leu Ser Ile Ala Gln<br>145                 150                    155                    160 | 480 |
| gca cac tcg cct gcc ttt tcc tgc gaa cag gtt cgc gcc ttc ccg gcc<br>Ala His Ser Pro Ala Phe Ser Cys Glu Gln Val Arg Ala Phe Pro Ala<br>                165                    170                    175 | 528 |
| ctt acc agc cta gac ctg tct gac aat cct gga ctg ggc gaa cgc gga<br>Leu Thr Ser Leu Asp Leu Ser Asp Asn Pro Gly Leu Gly Glu Arg Gly<br>                180                    185                    190 | 576 |
| ctg atg gcg gct ctc tgt ccc cac aag ttc ccg gcc atc cag aat cta<br>Leu Met Ala Ala Leu Cys Pro His Lys Phe Pro Ala Ile Gln Asn Leu<br>                195                    200                    205 | 624 |
| gcg ctg cgc aac aca gga atg gag acg ccc aca ggc gtg tgc gcc gca<br>Ala Leu Arg Asn Thr Gly Met Glu Thr Pro Thr Gly Val Cys Ala Ala<br>210                       215                    220 | 672 |
| ctg gcg gcg gca ggt gtg cag ccc cac agc cta gac ctc agc cac aac<br>Leu Ala Ala Ala Gly Val Gln Pro His Ser Leu Asp Leu Ser His Asn<br>225                 230                    235                    240 | 720 |
| tcg ctg cgc gcc acc gta aac cct agc gct ccg aga tgc atg tgg tcc<br>Ser Leu Arg Ala Thr Val Asn Pro Ser Ala Pro Arg Cys Met Trp Ser<br>                245                    250                    255 | 768 |
| agc gcc ctg aac tcc ctc aat ctg tcg ttc gct ggg ctg gaa cag gtg<br>Ser Ala Leu Asn Ser Leu Asn Leu Ser Phe Ala Gly Leu Glu Gln Val<br>                260                    265                    270 | 816 |
| cct aaa gga ctg cca gcc aag ctc aga gtg ctc gat ctc<br>Pro Lys Gly Leu Pro Ala Lys Leu Arg Val Leu Asp Leu<br>275                     280                    285 | 855 |

<210> SEQ ID NO 10
<211> LENGTH: 921
<212> TYPE: DNA
<213> ORGANISM: Artificial Sequence
<220> FEATURE:
<223> OTHER INFORMATION: Nucleotide sequence of the DNA encoding for
     the polypeptide of the present       invention
<220> FEATURE:
<221> NAME/KEY: CDS
<222> LOCATION: (1)..(921)

<400> SEQUENCE: 10

| | | |
|---|---|---|
| acc acg cca gaa cct tgt gag ctg gac gat gaa gat ttc cgc tgc gtc<br>Thr Thr Pro Glu Pro Cys Glu Leu Asp Asp Glu Asp Phe Arg Cys Val<br>1                   5                    10                    15 | 48 |
| tgc aac ttc tcc gaa cct cag ccc gac tgg tcc gaa gcc ttc cag tgt | 96 |

|   |   |   |   |   |   |   |   |   |   |   |   |   |   |   |   |   |
|---|---|---|---|---|---|---|---|---|---|---|---|---|---|---|---|---|
| Cys | Asn | Phe | Ser | Glu | Pro | Gln | Pro | Asp | Trp | Ser | Glu | Ala | Phe | Gln | Cys | |
|  |  | 20 |  |  |  | 25 |  |  |  | 30 |  |  |  |  |  |

```
gtg tct gca gta gag gtg gag atc cat gcc ggc ggt ctc aac cta gag     144
Val Ser Ala Val Glu Val Glu Ile His Ala Gly Gly Leu Asn Leu Glu
        35              40              45 ccg ttt cta aag cgc gtc gat gcg gac gcc gac ccg cgg cag tat gct     192
Pro Phe Leu Lys Arg Val Asp Ala Asp Ala Asp Pro Arg Gln Tyr Ala
    50              55              60 gac acg gtc aag gct ctc cgc gtg cgg cgg ctc aca gtg gga gcc gca     240
Asp Thr Val Lys Ala Leu Arg Val Arg Arg Leu Thr Val Gly Ala Ala
65              70              75              80 cag gtt cct gct cag cta ctg gta ggc gcc ctg cgt gtg cta gcg tac     288
Gln Val Pro Ala Gln Leu Leu Val Gly Ala Leu Arg Val Leu Ala Tyr
                85              90              95 tcc cgc ctc aag gaa ctg acg ctc gag gac cta aag ata acc ggc acc     336
Ser Arg Leu Lys Glu Leu Thr Leu Glu Asp Leu Lys Ile Thr Gly Thr
            100             105             110 atg cct ccg ctg cct ctg gaa gcc aca gga ctt gca ctt tcc agc ttg     384
Met Pro Pro Leu Pro Leu Glu Ala Thr Gly Leu Ala Leu Ser Ser Leu
        115             120             125 cgc cta cgc aac gtg tcg tgg gcg aca ggg cgt tct tgg ctc gcc gag     432
Arg Leu Arg Asn Val Ser Trp Ala Thr Gly Arg Ser Trp Leu Ala Glu
    130             135             140 ctg cag cag tgg ctc aag cca ggc ctc aag gta ctg agc att gcc caa     480
Leu Gln Gln Trp Leu Lys Pro Gly Leu Lys Val Leu Ser Ile Ala Gln
145             150             155             160 gca cac tcg cct gcc ttt tcc tgc gaa cag gtt cgc gcc ttc ccg gcc     528
Ala His Ser Pro Ala Phe Ser Cys Glu Gln Val Arg Ala Phe Pro Ala
                165             170             175 ctt acc agc cta gac ctg tct gac aat cct gga ctg ggc gaa cgc gga     576
Leu Thr Ser Leu Asp Leu Ser Asp Asn Pro Gly Leu Gly Glu Arg Gly
            180             185             190 ctg atg gcg gct ctc tgt ccc cac aag ttc ccg gcc atc cag aat cta     624
Leu Met Ala Ala Leu Cys Pro His Lys Phe Pro Ala Ile Gln Asn Leu
        195             200             205 gcg ctg cgc aac aca gga atg gag acg ccc aca ggc gtg tgc gcc gca     672
Ala Leu Arg Asn Thr Gly Met Glu Thr Pro Thr Gly Val Cys Ala Ala
    210             215             220 ctg gcg gcg gca ggt gtg cag ccc cac agc cta gac ctc agc cac aac     720
Leu Ala Ala Ala Gly Val Gln Pro His Ser Leu Asp Leu Ser His Asn
225             230             235             240 tcg ctg cgc gcc acc gta aac cct agc gct ccg aga tgc atg tgg tcc     768
Ser Leu Arg Ala Thr Val Asn Pro Ser Ala Pro Arg Cys Met Trp Ser
                245             250             255 agc gcc ctg aac tcc ctc aat ctg tcg ttc gct ggg ctg gaa cag gtg     816
Ser Ala Leu Asn Ser Leu Asn Leu Ser Phe Ala Gly Leu Glu Gln Val
            260             265             270 cct aaa gga ctg cca gcc aag ctc aga gtg ctc gat ctc gct tgc aac     864
Pro Lys Gly Leu Pro Ala Lys Leu Arg Val Leu Asp Leu Ala Cys Asn
        275             280             285 aga ctg aac agg gcg ccg cag cct gac gag ctg ccc gag gtg gat aac     912
Arg Leu Asn Arg Ala Pro Gln Pro Asp Glu Leu Pro Glu Val Asp Asn
    290             295             300 ctg aca ctg                                                         921
Leu Thr Leu
```

<210> SEQ ID NO 11
<211> LENGTH: 921
<212> TYPE: DNA
<213> ORGANISM: Artificial Sequence
<220> FEATURE:
<223> OTHER INFORMATION: Nucleotide sequence of the DNA encoding for
     the polypeptide of the present     invention
<220> FEATURE:
<221> NAME/KEY: CDS
<222> LOCATION: (1)..(921)

<400> SEQUENCE: 11

| | | | | | | | | | | | | | | | | |
|---|---|---|---|---|---|---|---|---|---|---|---|---|---|---|---|---|
| acc | acg | cca | gaa | cct | tgt | gag | ctg | gac | gat | gaa | gat | ttc | cgc | tgc | gtc | 48 |
| Thr | Thr | Pro | Glu | Pro | Cys | Glu | Leu | Asp | Asp | Glu | Asp | Phe | Arg | Cys | Val | |
| 1 | | | | 5 | | | | | 10 | | | | | 15 | | |

| tgc | aac | ttc | tcc | gaa | cct | cag | ccc | gac | tgg | tcc | gaa | gcc | ttc | cag | tgt | 96 |
|---|---|---|---|---|---|---|---|---|---|---|---|---|---|---|---|---|
| Cys | Asn | Phe | Ser | Glu | Pro | Gln | Pro | Asp | Trp | Ser | Glu | Ala | Phe | Gln | Cys | |
| | | | 20 | | | | | 25 | | | | | 30 | | | |

| gtg | tct | gca | gta | gag | gtg | gag | atc | cat | gcc | ggc | ggt | ctc | aac | cta | gag | 144 |
|---|---|---|---|---|---|---|---|---|---|---|---|---|---|---|---|---|
| Val | Ser | Ala | Val | Glu | Val | Glu | Ile | His | Ala | Gly | Gly | Leu | Asn | Leu | Glu | |
| | | 35 | | | | | 40 | | | | | 45 | | | | |

| ccg | ttt | cta | aag | cgc | gtc | gat | gcg | gac | gcc | gac | ccg | cgg | cag | tat | gct | 192 |
|---|---|---|---|---|---|---|---|---|---|---|---|---|---|---|---|---|
| Pro | Phe | Leu | Lys | Arg | Val | Asp | Ala | Asp | Ala | Asp | Pro | Arg | Gln | Tyr | Ala | |
| | 50 | | | | | 55 | | | | | 60 | | | | | |

| gac | acg | gtc | aag | gct | ctc | cgc | gtg | cgg | cgg | ctc | aca | gtg | gga | gcc | gca | 240 |
|---|---|---|---|---|---|---|---|---|---|---|---|---|---|---|---|---|
| Asp | Thr | Val | Lys | Ala | Leu | Arg | Val | Arg | Arg | Leu | Thr | Val | Gly | Ala | Ala | |
| 65 | | | | 70 | | | | | 75 | | | | | 80 | | |

| cag | gtt | cct | gct | cag | cta | ctg | gta | ggc | gcc | ctg | cgt | gtg | cta | gcg | tac | 288 |
|---|---|---|---|---|---|---|---|---|---|---|---|---|---|---|---|---|
| Gln | Val | Pro | Ala | Gln | Leu | Leu | Val | Gly | Ala | Leu | Arg | Val | Leu | Ala | Tyr | |
| | | | 85 | | | | | 90 | | | | | 95 | | | |

| tcc | cgc | ctc | aag | gaa | ctg | acg | ctc | gag | gac | cta | aag | ata | acc | ggc | acc | 336 |
|---|---|---|---|---|---|---|---|---|---|---|---|---|---|---|---|---|
| Ser | Arg | Leu | Lys | Glu | Leu | Thr | Leu | Glu | Asp | Leu | Lys | Ile | Thr | Gly | Thr | |
| | | 100 | | | | | 105 | | | | | 110 | | | | |

| atg | cct | ccg | ctg | cct | ctg | gaa | gcc | aca | gga | ctt | gca | ctt | tcc | agc | ttg | 384 |
|---|---|---|---|---|---|---|---|---|---|---|---|---|---|---|---|---|
| Met | Pro | Pro | Leu | Pro | Leu | Glu | Ala | Thr | Gly | Leu | Ala | Leu | Ser | Ser | Leu | |
| | 115 | | | | | 120 | | | | | 125 | | | | | |

| cgc | cta | cgc | aac | gtg | tcg | tgg | gcg | aca | ggg | cgt | tct | tgg | ctc | gcc | gag | 432 |
|---|---|---|---|---|---|---|---|---|---|---|---|---|---|---|---|---|
| Arg | Leu | Arg | Asn | Val | Ser | Trp | Ala | Thr | Gly | Arg | Ser | Trp | Leu | Ala | Glu | |
| 130 | | | | 135 | | | | | 140 | | | | | | | |

| ctg | cag | cag | tgg | ctc | aag | cca | ggc | ctc | aag | gta | ctg | agc | att | gcc | caa | 480 |
|---|---|---|---|---|---|---|---|---|---|---|---|---|---|---|---|---|
| Leu | Gln | Gln | Trp | Leu | Lys | Pro | Gly | Leu | Lys | Val | Leu | Ser | Ile | Ala | Gln | |
| 145 | | | | 150 | | | | | 155 | | | | | 160 | | |

| gca | cac | tcg | cct | gcc | ttt | tcc | tgc | gaa | cag | gtt | cgc | gcc | ttc | ccg | gcc | 528 |
|---|---|---|---|---|---|---|---|---|---|---|---|---|---|---|---|---|
| Ala | His | Ser | Pro | Ala | Phe | Ser | Cys | Glu | Gln | Val | Arg | Ala | Phe | Pro | Ala | |
| | | | 165 | | | | | 170 | | | | | 175 | | | |

| ctt | acc | agc | cta | gac | ctg | tct | gac | aat | cct | gga | ctg | ggc | gaa | cgc | gga | 576 |
|---|---|---|---|---|---|---|---|---|---|---|---|---|---|---|---|---|
| Leu | Thr | Ser | Leu | Asp | Leu | Ser | Asp | Asn | Pro | Gly | Leu | Gly | Glu | Arg | Gly | |
| | | 180 | | | | | 185 | | | | | 190 | | | | |

| ctg | atg | gcg | gct | ctc | tgt | ccc | cac | aag | ttc | ccg | gcc | atc | cag | aat | cta | 624 |
|---|---|---|---|---|---|---|---|---|---|---|---|---|---|---|---|---|
| Leu | Met | Ala | Ala | Leu | Cys | Pro | His | Lys | Phe | Pro | Ala | Ile | Gln | Asn | Leu | |
| | 195 | | | | | 200 | | | | | 205 | | | | | |

| gcg | ctg | cgc | aac | aca | gga | atg | gag | acg | ccc | aca | ggc | gtg | tgc | gcc | gca | 672 |
|---|---|---|---|---|---|---|---|---|---|---|---|---|---|---|---|---|
| Ala | Leu | Arg | Asn | Thr | Gly | Met | Glu | Thr | Pro | Thr | Gly | Val | Cys | Ala | Ala | |
| 210 | | | | 215 | | | | | 220 | | | | | | | |

| ctg | gcg | gcg | gca | ggt | gtg | cag | ccc | cac | agc | cta | gac | ctc | agc | cac | aac | 720 |
|---|---|---|---|---|---|---|---|---|---|---|---|---|---|---|---|---|
| Leu | Ala | Ala | Ala | Gly | Val | Gln | Pro | His | Ser | Leu | Asp | Leu | Ser | His | Asn | |
| 225 | | | | 230 | | | | | 235 | | | | | 240 | | |

| tcg | ctg | cgc | gcc | acc | gta | aac | cct | agc | gct | ccg | aga | tgc | atg | tgg | tcc | 768 |
|---|---|---|---|---|---|---|---|---|---|---|---|---|---|---|---|---|
| Ser | Leu | Arg | Ala | Thr | Val | Asn | Pro | Ser | Ala | Pro | Arg | Cys | Met | Trp | Ser | |
| | | | 245 | | | | | 250 | | | | | 255 | | | |

| agc | gcc | ctg | aac | tcc | ctc | aat | ctg | tcg | ttc | gct | ggg | ctg | gaa | cag | gtg | 816 |
|---|---|---|---|---|---|---|---|---|---|---|---|---|---|---|---|---|
| Ser | Ala | Leu | Asn | Ser | Leu | Asn | Leu | Ser | Phe | Ala | Gly | Leu | Glu | Gln | Val | |
| | | 260 | | | | | 265 | | | | | 270 | | | | |

| cct | aaa | gga | ctg | cca | gcc | aag | ctc | aga | gtg | ctc | gat | ctc | tgt | tgc | aac | 864 |
|---|---|---|---|---|---|---|---|---|---|---|---|---|---|---|---|---|
| Pro | Lys | Gly | Leu | Pro | Ala | Lys | Leu | Arg | Val | Leu | Asp | Leu | Cys | Cys | Asn | |

|  | | | | | | | | | | | 275 | | | 280 | | | 285 | | | |
| --- | --- | --- | --- | --- | --- | --- | --- | --- | --- | --- | --- | --- | --- | --- | --- | --- | --- | --- | --- | --- |

```
aga ctg aac agg gcg ccg cag cct gac gag ctg ccc gag gtg gat aac       912
Arg Leu Asn Arg Ala Pro Gln Pro Asp Glu Leu Pro Glu Val Asp Asn
    290                 295                 300 ctg aca ctg                                                            921
Leu Thr Leu
305
```

```
<210> SEQ ID NO 12
<211> LENGTH: 24
<212> TYPE: PRT
<213> ORGANISM: human

<400> SEQUENCE: 12

Leu Asp Leu Ser Cys Asn Arg Leu Asn Arg Ala Pro Gln Pro Asp Glu
1               5                   10                  15

Leu Pro Glu Val Asp Asn Leu Thr
            20

<210> SEQ ID NO 13
<211> LENGTH: 18
<212> TYPE: PRT
<213> ORGANISM: human

<400> SEQUENCE: 13

Glu Val Asp Asn Leu Thr Leu Asp Gly Asn Pro Phe Leu Val Pro Gly
1               5                   10                  15

Thr Ala

<210> SEQ ID NO 14
<211> LENGTH: 12
<212> TYPE: PRT
<213> ORGANISM: human

<400> SEQUENCE: 14

Thr Ala Leu Pro His Glu Gly Ser Met Asn Ser Gly
1               5                   10

<210> SEQ ID NO 15
<211> LENGTH: 15
<212> TYPE: PRT
<213> ORGANISM: human

<400> SEQUENCE: 15

Pro Ala Cys Ala Arg Ser Thr Leu Ser Val Gly Val Ser Gly Thr
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Peptide E

<400> SEQUENCE: 16

Gln Gly Pro Cys Arg Ala Phe Ile Lys Leu Trp Ala Phe Asp Cys
1               5                   10                  15

<210> SEQ ID NO 17
<211> LENGTH: 20
<212> TYPE: DNA
<213> ORGANISM: Artificial Sequence
<220> FEATURE:
<223> OTHER INFORMATION: sense primer 3
```

<400> SEQUENCE: 17
cacgccagaa ccttgtgagc                                                    20

<210> SEQ ID NO 18
<211> LENGTH: 38
<212> TYPE: DNA
<213> ORGANISM: Artificial Sequence
<220> FEATURE:
<223> OTHER INFORMATION: antisense primer 3

<400> SEQUENCE: 18
gtcagtgcac aggctgggac cacaacggat tgcattga                                38

<210> SEQ ID NO 19
<211> LENGTH: 30
<212> TYPE: DNA
<213> ORGANISM: Artificial Sequence
<220> FEATURE:
<223> OTHER INFORMATION: antisense primer 4

<400> SEQUENCE: 19
cccaagcttc tattacagtg tcaggttatc                                         30

<210> SEQ ID NO 20
<211> LENGTH: 30
<212> TYPE: DNA
<213> ORGANISM: Artificial Sequence
<220> FEATURE:
<223> OTHER INFORMATION: antisense primer 5

<400> SEQUENCE: 20
cccaagcttc tattagggca gctcgtcagg                                         30

<210> SEQ ID NO 21
<211> LENGTH: 30
<212> TYPE: DNA
<213> ORGANISM: Artificial Sequence
<220> FEATURE:
<223> OTHER INFORMATION: antisense primer 6

<400> SEQUENCE: 21
cccaagcttc tattactgcg gcgccctgtt                                         30

<210> SEQ ID NO 22
<211> LENGTH: 30
<212> TYPE: DNA
<213> ORGANISM: Artificial Sequence
<220> FEATURE:
<223> OTHER INFORMATION: antisense primer 7

<400> SEQUENCE: 22
cccaagcttc tattacagtc tgttgcagct                                         30

<210> SEQ ID NO 23
<211> LENGTH: 30
<212> TYPE: DNA
<213> ORGANISM: Artificial Sequence
<220> FEATURE:
<223> OTHER INFORMATION: antisense primer 8

<400> SEQUENCE: 23
cccaagcttc tattagagat cgagcactct                                         30

<210> SEQ ID NO 24

```
<211> LENGTH: 30
<212> TYPE: DNA
<213> ORGANISM: Artificial Sequence
<220> FEATURE:
<223> OTHER INFORMATION: antisense primer 9

<400> SEQUENCE: 24
cccaagcttc tattatacgg tggcgcgcag                                           30

<210> SEQ ID NO 25
<211> LENGTH: 30
<212> TYPE: DNA
<213> ORGANISM: Artificial Sequence
<220> FEATURE:
<223> OTHER INFORMATION: antisense primer 10

<400> SEQUENCE: 25
cccaagcttc tattaagaca ggtctaggct                                           30

<210> SEQ ID NO 26
<211> LENGTH: 30
<212> TYPE: DNA
<213> ORGANISM: Artificial Sequence
<220> FEATURE:
<223> OTHER INFORMATION: antisense primer 11

<400> SEQUENCE: 26
cccaagcttc tattagcctg gcttgagcca                                           30

<210> SEQ ID NO 27
<211> LENGTH: 20
<212> TYPE: DNA
<213> ORGANISM: Artificial Sequence
<220> FEATURE:
<223> OTHER INFORMATION: sense primer 4

<400> SEQUENCE: 27
ctctggctaa ctagagaacc                                                     20

<210> SEQ ID NO 28
<211> LENGTH: 21
<212> TYPE: DNA
<213> ORGANISM: Artificial Sequence
<220> FEATURE:
<223> OTHER INFORMATION: antisense primer 12

<400> SEQUENCE: 28
gcggaaatca caaggttctg g                                                   21

<210> SEQ ID NO 29
<211> LENGTH: 21
<212> TYPE: DNA
<213> ORGANISM: Artificial Sequence
<220> FEATURE:
<223> OTHER INFORMATION: sense primer 5

<400> SEQUENCE: 29
gaaccttgtg atttccgctg c                                                   21

<210> SEQ ID NO 30
<211> LENGTH: 20
<212> TYPE: DNA
<213> ORGANISM: Artificial Sequence
<220> FEATURE:
<223> OTHER INFORMATION: antisense primer 13

<400> SEQUENCE: 30
```

-continued ttattaggaa aggacagtgg                    20

<210> SEQ ID NO 31
<211> LENGTH: 30
<212> TYPE: DNA
<213> ORGANISM: Artificial Sequence
<220> FEATURE:
<223> OTHER INFORMATION: antisense primer 14

<400> SEQUENCE: 31
agccttgacc gtgtccgcat cgacgcgctt          30

<210> SEQ ID NO 32
<211> LENGTH: 30
<212> TYPE: DNA
<213> ORGANISM: Artificial Sequence
<220> FEATURE:
<223> OTHER INFORMATION: sense primer 6

<400> SEQUENCE: 32
aagcgcgtcg atgcggacac ggtcaaggct          30

<210> SEQ ID NO 33
<211> LENGTH: 39
<212> TYPE: DNA
<213> ORGANISM: Artificial Sequence
<220> FEATURE:
<223> OTHER INFORMATION: antisense primer 15

<400> SEQUENCE: 33
gttgtgagac aggtctaggc tggtaagggc cgggaaggc    39

<210> SEQ ID NO 34
<211> LENGTH: 39
<212> TYPE: DNA
<213> ORGANISM: Artificial Sequence
<220> FEATURE:
<223> OTHER INFORMATION: sense primer 7

<400> SEQUENCE: 34
gcccttacca gcctagacct gtctcacaac tcgctgcgc    39

<210> SEQ ID NO 35
<211> LENGTH: 39
<212> TYPE: DNA
<213> ORGANISM: Artificial Sequence
<220> FEATURE:
<223> OTHER INFORMATION: antisense primer 16

<400> SEQUENCE: 35
cagtctgttg caagacaggt ctaggctgtg gggctgcac    39

<210> SEQ ID NO 36
<211> LENGTH: 39
<212> TYPE: DNA
<213> ORGANISM: Artificial Sequence
<220> FEATURE:
<223> OTHER INFORMATION: sense primer 8

<400> SEQUENCE: 36
cacagcctag acctgtcttg caacagactg aacagggcg    39

<210> SEQ ID NO 37
<211> LENGTH: 39
<212> TYPE: DNA

```
<213> ORGANISM: Artificial Sequence
<220> FEATURE:
<223> OTHER INFORMATION: antisense primer 17

<400> SEQUENCE: 37
cagtctgttg caagacaggt ctaggctggt aagggccgg                              39

<210> SEQ ID NO 38
<211> LENGTH: 39
<212> TYPE: DNA
<213> ORGANISM: Artificial Sequence
<220> FEATURE:
<223> OTHER INFORMATION: sense primer 9

<400> SEQUENCE: 38
accagcctag acctgtcttg caacagactg aacagggcg                              39

<210> SEQ ID NO 39
<211> LENGTH: 23
<212> TYPE: DNA
<213> ORGANISM: Artificial Sequence
<220> FEATURE:
<223> OTHER INFORMATION: antisense primer 18

<400> SEQUENCE: 39
actctgagag cggctggcag tcc                                               23

<210> SEQ ID NO 40
<211> LENGTH: 23
<212> TYPE: DNA
<213> ORGANISM: Artificial Sequence
<220> FEATURE:
<223> OTHER INFORMATION: sense primer 10

<400> SEQUENCE: 40
tgccagccgc tctcagagtg ctc                                               23

<210> SEQ ID NO 41
<211> LENGTH: 23
<212> TYPE: DNA
<213> ORGANISM: Artificial Sequence
<220> FEATURE:
<223> OTHER INFORMATION: antisense primer 19

<400> SEQUENCE: 41
agatcgagag ctctgagctt ggc                                               23

<210> SEQ ID NO 42
<211> LENGTH: 20
<212> TYPE: DNA
<213> ORGANISM: Artificial Sequence
<220> FEATURE:
<223> OTHER INFORMATION: antisense primer 20

<400> SEQUENCE: 42
gagatcagcc actctgagct                                                   20

<210> SEQ ID NO 43
<211> LENGTH: 20
<212> TYPE: DNA
<213> ORGANISM: Artificial Sequence
<220> FEATURE:
<223> OTHER INFORMATION: antisense primer 21

<400> SEQUENCE: 43
gctgagagcg agcactctga                                                   20
```

<210> SEQ ID NO 44
<211> LENGTH: 20
<212> TYPE: DNA
<213> ORGANISM: Artificial Sequence
<220> FEATURE:
<223> OTHER INFORMATION: antisense primer 22

<400> SEQUENCE: 44
gcagctagca tcgagcactc                                           20

<210> SEQ ID NO 45
<211> LENGTH: 20
<212> TYPE: DNA
<213> ORGANISM: Artificial Sequence
<220> FEATURE:
<223> OTHER INFORMATION: antisense primer 23

<400> SEQUENCE: 45
gttgcaagcg agatcgagca                                           20

<210> SEQ ID NO 46
<211> LENGTH: 20
<212> TYPE: DNA
<213> ORGANISM: Artificial Sequence
<220> FEATURE:
<223> OTHER INFORMATION: antisense primer 24

<400> SEQUENCE: 46
tctgttagcg ctgagatcga                                           20

<210> SEQ ID NO 47
<211> LENGTH: 20
<212> TYPE: DNA
<213> ORGANISM: Artificial Sequence
<220> FEATURE:
<223> OTHER INFORMATION: antisense primer 25

<400> SEQUENCE: 47
gttcagagcg ttgcagctga                                           20

<210> SEQ ID NO 48
<211> LENGTH: 21
<212> TYPE: DNA
<213> ORGANISM: Artificial Sequence
<220> FEATURE:
<223> OTHER INFORMATION: antisense primer 26

<400> SEQUENCE: 48
tcaggctgcg ccgccctgtt c                                         21

<210> SEQ ID NO 49
<211> LENGTH: 21
<212> TYPE: DNA
<213> ORGANISM: Artificial Sequence
<220> FEATURE:
<223> OTHER INFORMATION: antisense primer 27

<400> SEQUENCE: 49
agctcgtcag cctgcggcgc c                                         21

<210> SEQ ID NO 50
<211> LENGTH: 21
<212> TYPE: DNA
<213> ORGANISM: Artificial Sequence
<220> FEATURE:

<223> OTHER INFORMATION: antisense primer 28

<400> SEQUENCE: 50
tcgtcagcct gcgccgccct g                                    21

<210> SEQ ID NO 51
<211> LENGTH: 21
<212> TYPE: DNA
<213> ORGANISM: Artificial Sequence
<220> FEATURE:
<223> OTHER INFORMATION: antisense primer 29

<400> SEQUENCE: 51
tccacctcgg ccagctcgtc a                                    21

<210> SEQ ID NO 52
<211> LENGTH: 23
<212> TYPE: DNA
<213> ORGANISM: Artificial Sequence
<220> FEATURE:
<223> OTHER INFORMATION: sense primer 11

<400> SEQUENCE: 52
agctcagagc tctcgatctc agc                                  23

<210> SEQ ID NO 53
<211> LENGTH: 20
<212> TYPE: DNA
<213> ORGANISM: Artificial Sequence
<220> FEATURE:
<223> OTHER INFORMATION: sense primer 12

<400> SEQUENCE: 53
agagtggctg atctcagctg                                      20

<210> SEQ ID NO 54
<211> LENGTH: 20
<212> TYPE: DNA
<213> ORGANISM: Artificial Sequence
<220> FEATURE:
<223> OTHER INFORMATION: sense primer 13

<400> SEQUENCE: 54
gtgctcgctc tcagctgcaa                                      20

<210> SEQ ID NO 55
<211> LENGTH: 20
<212> TYPE: DNA
<213> ORGANISM: Artificial Sequence
<220> FEATURE:
<223> OTHER INFORMATION: sense primer 14

<400> SEQUENCE: 55
ctcgatgcta gctgcaacag                                      20

<210> SEQ ID NO 56
<211> LENGTH: 20
<212> TYPE: DNA
<213> ORGANISM: Artificial Sequence
<220> FEATURE:
<223> OTHER INFORMATION: sense primer 15

<400> SEQUENCE: 56
gatctcgctt gcaacagact                                      20

```
<210> SEQ ID NO 57
<211> LENGTH: 20
<212> TYPE: DNA
<213> ORGANISM: Artificial Sequence
<220> FEATURE:
<223> OTHER INFORMATION: sense primer 16

<400> SEQUENCE: 57
ctcagcgcta acagactgaa                                              20

<210> SEQ ID NO 58
<211> LENGTH: 20
<212> TYPE: DNA
<213> ORGANISM: Artificial Sequence
<220> FEATURE:
<223> OTHER INFORMATION: sense primer 17

<400> SEQUENCE: 58
tgcaacgctc tgaacagggc                                              20

<210> SEQ ID NO 59
<211> LENGTH: 21
<212> TYPE: DNA
<213> ORGANISM: Artificial Sequence
<220> FEATURE:
<223> OTHER INFORMATION: sense primer 18

<400> SEQUENCE: 59
gaacagggcg gcgcagcctg a                                            21

<210> SEQ ID NO 60
<211> LENGTH: 21
<212> TYPE: DNA
<213> ORGANISM: Artificial Sequence
<220> FEATURE:
<223> OTHER INFORMATION: sense primer 19

<400> SEQUENCE: 60
ggcgccgcag gctgacgagc t                                            21

<210> SEQ ID NO 61
<211> LENGTH: 21
<212> TYPE: DNA
<213> ORGANISM: Artificial Sequence
<220> FEATURE:
<223> OTHER INFORMATION: sense primer 20

<400> SEQUENCE: 61
cagggcggcg caggctgacg a                                            21

<210> SEQ ID NO 62
<211> LENGTH: 21
<212> TYPE: DNA
<213> ORGANISM: Artificial Sequence
<220> FEATURE:
<223> OTHER INFORMATION: sense primer 21

<400> SEQUENCE: 62
tgacgagctg gccgaggtgg a                                            21

<210> SEQ ID NO 63
<211> LENGTH: 20
<212> TYPE: DNA
<213> ORGANISM: Artificial Sequence
<220> FEATURE:
<223> OTHER INFORMATION: sense primer 22
```

-continued

```
<400> SEQUENCE: 63
tgcaacgatc tgaacagggc                                                   20

<210> SEQ ID NO 64
<211> LENGTH: 20
<212> TYPE: DNA
<213> ORGANISM: Artificial Sequence
<220> FEATURE:
<223> OTHER INFORMATION: antisense primer 30

<400> SEQUENCE: 64
gttcagatcg ttgcagctga                                                   20

<210> SEQ ID NO 65
<211> LENGTH: 20
<212> TYPE: DNA
<213> ORGANISM: Artificial Sequence
<220> FEATURE:
<223> OTHER INFORMATION: sense primer 23

<400> SEQUENCE: 65
ctcgatctct gttgcaacag                                                   20

<210> SEQ ID NO 66
<211> LENGTH: 20
<212> TYPE: DNA
<213> ORGANISM: Artificial Sequence
<220> FEATURE:
<223> OTHER INFORMATION: antisense primer 31

<400> SEQUENCE: 66
tctgttgcaa cagagatcga                                                   20

<210> SEQ ID NO 67
<211> LENGTH: 20
<212> TYPE: DNA
<213> ORGANISM: Artificial Sequence
<220> FEATURE:
<223> OTHER INFORMATION: sense primer 24

<400> SEQUENCE: 67
ctcgatctcg gttgcaacag                                                   20

<210> SEQ ID NO 68
<211> LENGTH: 20
<212> TYPE: DNA
<213> ORGANISM: Artificial Sequence
<220> FEATURE:
<223> OTHER INFORMATION: antisense primer 32

<400> SEQUENCE: 68
tctgttgcaa ccgagatcga                                                   20

<210> SEQ ID NO 69
<211> LENGTH: 20
<212> TYPE: DNA
<213> ORGANISM: Artificial Sequence
<220> FEATURE:
<223> OTHER INFORMATION: sense primer 25

<400> SEQUENCE: 69
ctcgatctca cttgcaacag                                                   20

<210> SEQ ID NO 70
<211> LENGTH: 20
```

```
<212> TYPE: DNA
<213> ORGANISM: Artificial Sequence
<220> FEATURE:
<223> OTHER INFORMATION: antisense primer 33

<400> SEQUENCE: 70
tctgttgcaa gtgagatcga                                                    20

<210> SEQ ID NO 71
<211> LENGTH: 20
<212> TYPE: DNA
<213> ORGANISM: Artificial Sequence
<220> FEATURE:
<223> OTHER INFORMATION: sense primer 26

<400> SEQUENCE: 71
ctcgatctcc tttgcaacag                                                    20

<210> SEQ ID NO 72
<211> LENGTH: 20
<212> TYPE: DNA
<213> ORGANISM: Artificial Sequence
<220> FEATURE:
<223> OTHER INFORMATION: antisense primer 34

<400> SEQUENCE: 72
tctgttgcaa aggagatcga                                                    20

<210> SEQ ID NO 73
<211> LENGTH: 23
<212> TYPE: PRT
<213> ORGANISM: Artificial Sequence
<220> FEATURE:
<223> OTHER INFORMATION: sense primer 27

<400> SEQUENCE: 73

Gly Ala Tyr Ala Thr His Gly Thr Asn Ala Thr Gly Ala Cys Asn Cys
 1               5                  10                  15

Ala Arg Trp Ser Asn Cys Cys
             20

<210> SEQ ID NO 74
<211> LENGTH: 17
<212> TYPE: PRT
<213> ORGANISM: Artificial Sequence
<220> FEATURE:
<223> OTHER INFORMATION: sense primer 28

<400> SEQUENCE: 74

Ala Cys Asn Trp Ser Asn Ala Thr His Trp Ser Asn Ala Thr His Trp
1               5                  10                  15

Ser

<210> SEQ ID NO 75
<211> LENGTH: 17
<212> TYPE: PRT
<213> ORGANISM: Artificial Sequence
<220> FEATURE:
<223> OTHER INFORMATION: antisense primer 35

<400> SEQUENCE: 75

Asn Ala Arg Asn Ser Trp Asn Ala Arg Asn Gly Thr Asn Ser Trp Asn
1               5                  10                  15

Ser
```

```
<210> SEQ ID NO 76
<211> LENGTH: 24
<212> TYPE: PRT
<213> ORGANISM: Artificial Sequence
<220> FEATURE:
<223> OTHER INFORMATION: antisense primer 36

<400> SEQUENCE: 76
```

Arg Thr Thr Arg Thr Gly Asn Cys Lys Tyr Thr Cys Arg Thr Ala Tyr
1               5                   10                  15

Thr Cys Arg Thr Cys Tyr Thr Thr
            20

```
<210> SEQ ID NO 77
<211> LENGTH: 23
<212> TYPE: PRT
<213> ORGANISM: Artificial Sequence
<220> FEATURE:
<223> OTHER INFORMATION: sense primer 29

<400> SEQUENCE: 77
```

Ala Thr Gly Ala Ala Tyr Thr Gly Gly Gly Thr Asn Ile Ile Ile Cys
1               5                   10                  15

Ala Arg Gly Cys Asn Cys Cys
            20

```
<210> SEQ ID NO 78
<211> LENGTH: 23
<212> TYPE: PRT
<213> ORGANISM: Artificial Sequence
<220> FEATURE:
<223> OTHER INFORMATION: sense primer 30

<400> SEQUENCE: 78
```

Ala Thr Gly Ala Ala Tyr Thr Gly Gly Gly Thr Asn Ile Ile Ile Cys
1               5                   10                  15

Ala Arg Cys Cys Asn Gly Cys
            20

```
<210> SEQ ID NO 79
<211> LENGTH: 25
<212> TYPE: PRT
<213> ORGANISM: Artificial Sequence
<220> FEATURE:
<223> OTHER INFORMATION: antisense primer 37

<400> SEQUENCE: 79
```

Tyr Thr Thr Asn Ala Cys Asn Ala Arg Arg Cys Ala Asn Cys Cys Asn
1               5                   10                  15

Ala Arg Asn Gly Thr Asn Ala Gly Gly
            20                  25

```
<210> SEQ ID NO 80
<211> LENGTH: 26
<212> TYPE: PRT
<213> ORGANISM: Artificial Sequence
<220> FEATURE:
<223> OTHER INFORMATION: antisense primer 38

<400> SEQUENCE: 80
```

Arg Thr Ala Asn Cys Cys Asn Thr Thr Asn Ala Cys Asn Ala Arg Arg
1               5                   10                  15

Cys Ala Asn Cys Cys Asn Ala Arg Asn Gly
            20                  25

```
<210> SEQ ID NO 81
<211> LENGTH: 26
<212> TYPE: PRT
<213> ORGANISM: Artificial Sequence
<220> FEATURE:
<223> OTHER INFORMATION: sense primer 31

<400> SEQUENCE: 81

Gly Thr Asn Ala Ala Arg Tyr Thr Asn Tyr Thr Asn Tyr Thr Asn Gly
1               5                   10                  15

Ala Arg Trp Ser Asn Gly Gly Asn Gly Gly
            20                  25

<210> SEQ ID NO 82
<211> LENGTH: 23
<212> TYPE: PRT
<213> ORGANISM: Artificial Sequence
<220> FEATURE:
<223> OTHER INFORMATION: sense primer 32

<400> SEQUENCE: 82

Trp Ser Asn Gly Gly Asn Gly Gly Asn Gly Gly Asn Tyr Thr Asn Gly
1               5                   10                  15

Thr Asn Cys Ala Arg Cys Cys
            20

<210> SEQ ID NO 83
<211> LENGTH: 36
<212> TYPE: DNA
<213> ORGANISM: Artificial Sequence
<220> FEATURE:
<223> OTHER INFORMATION: 5' UTR sense strand

<400> SEQUENCE: 83
gcaagcttga tccagacagg acacaggcca gaacat                              36

<210> SEQ ID NO 84
<211> LENGTH: 29
<212> TYPE: DNA
<213> ORGANISM: Artificial Sequence
<220> FEATURE:
<223> OTHER INFORMATION: 3' UTR antisense strand

<400> SEQUENCE: 84
cacgaattct gcagtggtgc agcatcagc                                      29
```